(12) United States Patent
Ma et al.

(10) Patent No.: US 10,968,495 B2
(45) Date of Patent: Apr. 6, 2021

(54) LACTOBACILLUS REUTERI AND USE THEREOF

(71) Applicant: INFINITOS (CHINA) COMPANY LTD., Guangdong (CN)

(72) Inventors: Fangli Ma, Guangdong (CN); Wei Chen, Guangdong (CN); Gang Wang, Guangdong (CN); Guangsu Zhu, Guangdong (CN); Yuanyuan Wang, Guangdong (CN); Lingyun Xiao, Guangdong (CN); Minghua Hu, Guangdong (CN); Hao Zhang, Guangdong (CN); Jianxin Zhao, Guangdong (CN); Chung Wah Ma, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 153 days.

(21) Appl. No.: 16/109,747

(22) Filed: Aug. 23, 2018

(65) Prior Publication Data

US 2019/0112675 A1    Apr. 18, 2019

(30) Foreign Application Priority Data

Oct. 17, 2017    (CN) .......................... 201710963119.2

(51) Int. Cl.
*C12R 1/225*   (2006.01)
*C12N 1/20*   (2006.01)
(Continued)

(52) U.S. Cl.
CPC ............ *C12R 1/225* (2013.01); *A23C 9/1234* (2013.01); *A23C 11/106* (2013.01); *A23C 13/16* (2013.01);
(Continued)

(58) Field of Classification Search
CPC . C12R 1/225; A23L 11/09; A61P 3/00; A23C 14/16
See application file for complete search history.

(56) References Cited

FOREIGN PATENT DOCUMENTS

| CN | 104413334 A | 3/2015 |
|---|---|---|
| CN | 104561227 A | 4/2015 |

(Continued)

OTHER PUBLICATIONS

Simon et al (Intake of Lactobacillus reuteri Improves Incretin and Insulin Secretion in Glucose-Tolerant Humans: A Proof of Concept , American diabetes Association, Oct. 2015 (Year: 2015).*

(Continued)

*Primary Examiner* — Louise W Humphrey
*Assistant Examiner* — Anjali Ajit Hirani
(74) *Attorney, Agent, or Firm* — Yue (Robert) Xu; Apex Attorneys at Law, LLP

(57) ABSTRACT

Provided is a strain CCFM8631 of *Lactobacillus reuteri* and use thereof. The strain CCFM8631 of *Lactobacillus reuteri* can significantly increase neurotransmitter 5-hydroxytryptamine level in peripheral blood, recover the hormone levels, for example testosterone and so on in peripheral blood of rat, normalize abnormal abundances of *Blautia* genus and *Turicibacter* genus, *Oscillospira* genus and *Bifidobacterium* genus in intestinal flora of rat affected by high-fat high-starch diet, show good tolerance to simulated gastrointestinal fluid and quickly colonize in intestinal, significantly improve pathological damages of tissues such as liver, duodenum and so on, and increase triglyceride and total cholesterol levels in serum and oral glucose tolerance of rat with metabolic syndrome caused by high-fat high-starch diet. The strain CCFM8631 of *Lactobacillus reuteri* can be used for preventing, relieving or treating metabolic disorder, such as metabolic syndrome, irritable bowel syndrome and (Continued)

mental diseases related to metabolic syndrome such as anxiety, depression and so on.

4 Claims, 5 Drawing Sheets

(51) Int. Cl.
    *A61P 3/00*     (2006.01)
    *A61P 1/00*     (2006.01)
    *A23L 33/135*     (2016.01)
    *A23C 9/123*     (2006.01)
    *A23C 13/16*     (2006.01)
    *A23C 19/032*     (2006.01)
    *A23C 11/10*     (2021.01)
    *A23L 11/00*     (2021.01)
    *A23L 19/00*     (2016.01)
    *A61K 35/747*     (2015.01)
    *A23C 19/06*     (2006.01)
    *A61K 35/00*     (2006.01)

(52) U.S. Cl.
    CPC ........ *A23C 19/0323* (2013.01); *A23C 19/062* (2013.01); *A23L 11/09* (2016.08); *A23L 19/00* (2016.08); *A23L 33/135* (2016.08); *A61K 35/747* (2013.01); *A61P 1/00* (2018.01); *A61P 3/00* (2018.01); *C12N 1/20* (2013.01); *A23V 2002/00* (2013.01); *A23Y 2220/71* (2013.01); *A61K 2035/115* (2013.01)

(56) References Cited

FOREIGN PATENT DOCUMENTS

| | | |
|---|---|---|
| CN | 104771416 A | 7/2015 |
| CN | 104887716 A | 9/2015 |
| CN | 105030950 A | 11/2015 |
| CN | 105853467 A | 8/2016 |

OTHER PUBLICATIONS

Mu et al (frontiers in Microbiology, Role of Lactobacillus reuteri in Human Health and Diseases, Apr. 19, 2018) (Year: 2018).*
Carabotti et al ( Annals of Gastroenterology The gut-brain axis: interactions between enteric microbiota, central and enteric nervous systems, Jun. 2015). (Year: 2015).*
First Office Action dated Jul. 3, 2019 for Chinese patent application No. 201710963119.2, 7 pages.
Wang Lu et al., Microbial euphoria, Shanghai Science and Technology,Dec. 31, 2015.
Cui Xin-yao et al., The approach to structure and function of gut microbiota in patients with depressive syndrome, Chinese Journal of Microccology, vol. 27 No. 10, Oct. 31, 2015.
Zhu Guang-su et al., Safety assessment of two probiotic strains with the function of metabolic syndrome alleviation isolated from human gut, Food and Fermentation Industries, 44(8) :57-64, Oct. 17, 2018.

* cited by examiner

LACTOBACILLUS REUTERI AND USE THEREOF

CROSS REFERENCE TO RELATED APPLICATIONS

This application claims the priority of Chinese Patent Application No. 201710963119.2, filed on Oct. 17, 2017, and the disclosures of which are hereby incorporated by reference.

FIELD

The present disclosure relates to the field of microbe technology, specifically to a *Lactobacillus reuteri* and use thereof, especially to a *Lactobacillus reuteri* that is capable of modulating intestinal flora, modulating brain-gut axis and significantly alleviating metabolic syndrome, and use thereof.

BACKGROUND

Recent years, with the developing economy, life-styles of people in many countries have changed obviously. With the amount of physical activity has decreased, obesity rate has increased significantly, and prevalence rates of diabetes and metabolic syndrome have increased by a large margin. An epidemiology survey shows that 20% to 30% of the adults across the globe are suffering from metabolic syndrome. In 2013, a multicenter, multistage stratified, large-scale sampling survey carried out by Chinese Diabetes Society of Chinese Medical Association showed that among people over 20 years old in large and medium-sized cities, towns and countryside of China, prevalence rates of metabolic syndrome in men and women were 16.7% and 11.7%, respectively, and the total prevalence rate was 13.7%. Furthermore, the rate was continuously increasing. Analyses show that age, blood pressure, diabetes family history, obesity, hyperlipidemia, male, low income and little exercise are main related risk factors for metabolic syndrome. The survey also found that the rates of the overweight and the obesity among people have increased by a large margin, and prevalence rate of metabolic syndrome of male is significant higher than that of female at the same age among middle-aged crowd.

Metabolic syndrome is a clinical syndrome, which has simultaneous symptoms of central obesity, fasting blood glucose rising, high blood pressure, decrease of high-density lipoprotein cholesterol and increase of triacylglycerol, in which numerous hazardous factors basing on the abnormal pathological changes of carbohydrate metabolism, lipid metabolism and protein metabolism aggregates, and which promotes development of diabetes (type II) and cardiovascular diseases such as atherosclerosis and so on. Due to metabolic syndrome is a pathological condition in which numerous metabolic abnormalities aggregates, its occurrence is relates to insulin resistance, becoming a hot spot in the research field of cardiovascular diseases and diabetes, and raising many controversies at home and abroad. In addition, metabolic syndrome accompanies with disorder of intestinal microecosystem. Disorder of intestinal microecosystem may further lead to disorder of intestinal functions, nerve center functions and peripheral nerve functions, for example, intestinal inflammation, inflammatory bowel disease (IBD) and irritable bowel syndrome (IBS), abnormality of neurotransmitter 5-hydroxytryptamine level and level of some hormone and so on. Many researches have shown that abundances of intestinal microbes of some genus have intimate connection with intestinal diseases, for example, the abundance of *Blautia* genus will rise in intestinal flora of IBS patient, and the abundance of *Oscillospira* genus is closely related to the body mass index. At the same time, researches also show that mental diseases such as depression, anxiety and so on have intimate connection with metabolic syndrome, intestinal flora disorder, and low 5-hydroxytryptamine level in human body. Improving 5-hydroxytryptamine level in peripheral blood helps increasing neurotransmitter level of central nervous system, so that relieving symptoms of anxiety, depression and so on.

At present, all the drug treatments of metabolic syndrome aim to decrease all kinds of risk factors, and these drugs include: anti-obesity drugs for weight loss; dimethylbiguanide and thiazolidinediones for reducing insulin resistance; sulfonylurea and rosiglitazone for controlling blood glucose; fibrate and statin for improving disorder of lipid metabolism; captopril, amlodipine and so on for controlling the blood pressure; drugs for treating intestinal diseases such as IBD, IBS and so on, including glucocorticoid, immunosuppressant, psychotropic drugs and so on; drugs for mental diseases such as anxiety, depression and so on, including selective serotonin reuptake inhibitors such as paroxetine, noradrenaline, and specific 5-hydroxytryptamine antidepressant drugs such as mirtazapine and so on. All of the medicines above have certain therapeutic effects, but as the conditions getting worse, the amounts of medicine used increase, the interactions between the medicines as well as the toxic and side effects of medicines become significant, leading to adverse reaction of digestive tract and showing liver and renal toxicity in some degree. In consideration of problems of the medicines, early intervention in metabolic syndrome, intestinal disease and mental disease can effectively decrease onset risk of cardiovascular and cerebrovascular diseases, diabetes, inflammatory bowel diseases, depression and so on.

Probiotics are edible microbes that are beneficial to human health, which have potential functions of alleviating abnormal metabolism of blood glucose and blood lipid, and modulating intestinal flora proportion and brain-gut axis. Thus, there is important social and economy value to research and develop probiotic products that can effectively intervene the occurrence and development of metabolic syndrome, intestinal diseases and mental diseases.

At present, there is no patent about using probiotics to increase 5-hydroxytryptamine level so as to regulate brain-gut axis and relieve anxiety and depression. There is also no patent about modulating the abnormal abundance of *Oscillospira* genus to relieve metabolic diseases. Although there is related patent application (CN107083339A) that discloses adding *Blautia* bacteria to protect piglets from diarrhea, there is no patent about modulating the abnormal abundance of *Blautia* genus bacteria in intestinal tract so as to alleviate intestinal disease by the uptake of edible microbes (list of bacterium that can be permitted to be used in food, infant food, health products by National Health Commission of the People's Republic of China, 2014). In addition, there are some patents or patent application relating to compositions and preparation method thereof for preventing and curing metabolic syndrome. For example, CN104906263A discloses a composition consisting of tea polyphenol, procyanidin and POTENTILLAE DISCOLORIS HERBA extract, which is used to treat metabolic syndrome. CN105796674A discloses a traditional Chinese medicine composition comprising PLANTAGINIS SEMEN, COPTIDIS RHIZOMA and so on, which is capable of preventing and curing metabolic syndrome. In addition, a few patents relate to probiotics-containing compositions that are used to improve metabolic syndrome, and the methods for preparing the same. For example, CN105816623A discloses a probiotic-fermented traditional Chinese medicine composition being used to cure and improve metabolic syndrome, which is made from traditional Chinese medicine such as PANACIS QUINQUEFOLII RADIX, DIOSCOREAE RHIZOMA, MOUTAN CORTEX, PORIA by extracting and fermenting the extract with probiotics. All the above patents and patent applications are using traditional Chinese medicine components or a mixture of bacteria and traditional Chinese medicine to alleviate metabolic syndrome, in which the bacteria and the functions of the bacteria are not clear. CN105567586A discloses a *Lactobacillus plantarum* NCU116 with antidiabetic function, which achieves antidiabetic effects through modulating body blood glucose, blood lipid, hormone level and body metabolism. The *Lactobacillus plantarum* is screened and selected from bacteria in kimchi instead of human sources. No evidence shows that *Lactobacillus plantarum* can colonize in human intestinal tract and take effects. So far, there is no a human-sourced individual probiotic (such as *Lactobacillus reuteri*) that can colonize in human intestinal tract to relieve the metabolic syndrome, or to alleviate symptoms such as hyperglycemia, hyperlipidemia, intestinal flora imbalance, intestinal inflammation and so on, and related mental diseases.

SUMMARY

In view of above, an object of the present disclosure is to solve the problems in the prior art by providing a probiotics. The probiotics can colonize in intestinal tract of human body, improve 5-hydroxytryptamine level in peripheral blood, regulate brain-gut axis and recovering testosterone level in serum back to normal level, normalize abnormal abundances of *Blautia* genus, *Turicibacter* genus, *Oscillospira* genus and *Bifidobacterium* genus in intestinal flora, improve metabolic syndrome, relieve hyperglycemia, hyperlipidemia and inflammation of liver and duodenum, liver fibrosis and other symptoms.

The present disclosure provides a strain CCFM8631 of *Lactobacillus reuteri*, which is deposited at China General Microbiological Culture Collection Center (CGMCC, Address: Beijing Institute of Microbiology, Chinese Academy of Sciences, No. 1, Beichen West Road, Chaoyang District, Beijing, China) on Jul. 7, 2017, with an accession number CGMCC 14394.

In one embodiment, the present disclosure studies effect of strain CCFM8631 of *Lactobacillus reuteri* on intestinal flora imbalance caused by high-carbohydrate and high-fat diet. The results show that the uptake of strain CCFM8631 of *Lactobacillus reuteri* significantly recovers relative abundances of *Bifidobacterium* genus and *Turicibacter* genus in disordered intestinal microbes of rat feces, and also regulates the abundances of *Oscillospira* genus and *Blautia* genus in rat feces back to normal level. The intervention effect is obviously better than that of *Lactobacillus rhamnosus* LGG.

In one embodiment, the present disclosure studies protection effects of strain CCFM8631 of *Lactobacillus reuteri* on tissue damages of liver, duodenum and so on in rat with metabolic syndrome. The results show that administration of strain CCFM8631 of *Lactobacillus reuteri* by intragastric gavage significantly improves symptoms caused by high-fat high-starch diet, such as hepatocyte microvesicular steatosis, interstitial inflammatory cell infiltration, early fibrosis of liver tissue, duodenum villi broadening, interstitial edema, increasing of inflammatory cells and so on in rats, and the intervention effect is obviously better than that of *Lactobacillus rhamnosus* LGG.

In one embodiment, the present disclosure studies effect of strain CCFM8631 of *Lactobacillus reuteri* on (fasting) blood glucose level of rat with metabolic syndrome. The results show that administration of strain CCFM8631 of *Lactobacillus reuteri* by intragastric gavage obviously decreases the fasting blood glucose level of the model rat close to the blank control group. The ability of strain CCFM8631 of *Lactobacillus reuteri* on decreasing fasting blood glucose level of rat is better than that of rosiglitazone and *Lactobacillus rhamnosus* LGG by intragastric gavage administration.

In one embodiment, the present disclosure studies effect of strain CCFM8631 of *Lactobacillus reuteri* on oral glucose tolerance of rat with metabolic syndrome. The results show that strain CCFM8631 of *Lactobacillus reuteri* significantly improves oral glucose tolerance and the effect is better than that of *Lactobacillus rhamnosus* LGG, indicating that strain CCFM8631 of *Lactobacillus reuteri* can further decrease glucose level by improving glucose tolerance.

In one embodiment, the present disclosure studies effects of strain CCFM8631 of *Lactobacillus reuteri* on total cholesterol (TC) and triglyceride (TG) in serum of rat with metabolic syndrome, respectively. The results show that administration of strain CCFM8631 of *Lactobacillus reuteri* by intragastric gavage decreases levels of total cholesterol and triglyceride in serum.

Further, in one embodiment, the present disclosure studies effects of strain CCFM8631 of *Lactobacillus reuteri* on 5-HT and testosterone level in serum of rat with metabolic syndrome, respectively. The results show that administration of strain CCFM8631 of *Lactobacillus reuteri* by intragastric gavage improves 5-hydroxytryptamine (5-HT) level in rat serum, and reduces testosterone in serum back to normal level.

Therefore, the present disclosure provides use of strain CCFM8631 of *Lactobacillus reuteri* in preparing products that can improve metabolic syndrome, regulate intestinal flora or regulate brain-gut axis.

Therein, the improving metabolic syndrome is to relieve symptoms of hyperglycemia and hyperlipidemia, inflammation of liver and duodenum, and liver tissue fibrosis; the modulating intestinal flora is to normalize abnormal abundances of *Blautia* genus, *Turicibacter* genus, *Oscillospira* genus and *Bifidobacterium* genus in intestinal flora; and the modulating brain-gut axis as well as relieving anxiety and depression is to increase 5-hydroxytryptamine level in peripheral blood.

The product of the present disclosure includes but is not limited to health food or pharmaceutical preparation.

Therein, the health food includes but is not limited to microbial agent or fermented food.

Further, the present disclosure provides a microbial agent comprising the strain CCFM8631 of *Lactobacillus reuteri*.

Preferably, the viable count of the strain CCFM8631 of *Lactobacillus reuteri* in the microbial agent is more than $10^6$ CFU/g The microbial agent of the present disclosure can be prepared by routine methods.

In some embodiments, the method for preparing the microbial agent is:

inoculating the strain CCFM8631 of *Lactobacillus reuteri* to a modified MRS medium at an inoculum size of 2 to 4 wt %, culturing for 18 to 20 h at 37° C. under anaerobic conditions, collecting bacteria, resuspending the bacteria with a protectant to reach a bacterial density of $10^{10}$ CFU/mL, culturing the suspension at 37° C. for 50 to 70 minutes under anaerobic conditions, and drying the resulting culture.

Therein, the modified MRS medium (MRS) in the present disclosure is prepared by the specific method as follows: dissolving 10 g of tryptone, 10 g of beef extract, 5 g of yeast powder, 20 g of glucose, 5 g of sodium acetate, 2 g of ammonium citrate dibasic, 2 g of dipotassium hydrogen phosphate, 0.5 g of magnesium sulfate heptahydrate, 1 mL of Tween-80, and 0.25 g of manganese sulfate monohydrate in water, diluting the mixture to 1000 mL with water, modulating the pH to 6.5, and autoclaving at 119-123° C. for 15 to 25 minutes.

The protectant in the method of the present disclosure is an aqueous solution that contains 100 g/L to 150 g/L of nonfat milk powder, 100 g/L to 150 g/L of maltodextrin and 140 g/L to 160 g/L of trehalose. That is, the protectant consists of nonfat milk powder, maltodextrin, trehalose and water, wherein the concentration of nonfat milk powder is from 100 g/L to 150 g/, the concentration of maltodextrin is from 100 g/L to 150 g/L, and the concentration of trehalose is from 140 g/L to 160 g/L.

Preferably, in the method of the present disclosure, bacteria collected after culturing in the modified MRS medium are subjected to washing with phosphate buffer solution for 2 to 4 times, and pH of the phosphate buffer solution is from 6.8 to 7.2.

The drying of the method in the present disclosure can be any of the drying procedures for bacteria solution, for example vacuum freeze-drying. In some embodiments, the drying of the present disclosure is vacuum freeze-drying after pre-freezing the bacteria at −15 to −20° C. for 8 to 14 h.

The present disclosure also provides a fermented food which is produced by using the strain CCFM8631 of *Lactobacillus reuteri* as a starter culture.

The fermented food is fermented dairy products, fermented bean products or fermented fruit and vegetable products.

The fermented dairy products include but are not limited to yogurt, sour cream and cheese. The fermented bean products include but are not limited to soymilk, fermented beans and bean paste. The fruits and vegetables in the fermented fruit and vegetable products include but are not limited to cucumber, carrot, beet, celery and cabbage.

The present disclosure also provides a pharmaceutical preparation, comprising an effective amount of the strain CCFM8631 of *Lactobacillus reuteri* and a pharmaceutically acceptable adjuvant.

The pharmaceutically acceptable adjuvant is one or more selected from the group consisting of filler, adhesive, wetting agent, disintegrating agent, lubricant, and flavoring agent.

In some embodiments of the present disclosure, the pharmaceutical preparation is a granule, a capsule, a tablet, a pill or an oral liquid.

The beneficial technical effects of the present disclosure are as follows.

The strain CCFM8631 of *Lactobacillus reuteri* of the present disclosure significantly increases neurotransmitter 5-hydroxytryptamine (5-HT) level in peripheral blood of rat, regulates brain-gut axis, relieves mental illnesses related to metabolic syndrome, for example anxiety, depression and so on, recovers the hormone level, for example testosterone and so on in peripheral blood of rat caused by high-fat high-starch diet, recovers abundances of *Blautia* genus, *Turicibacter* genus, *Oscillospira* genus and *Bifidobacterium* genus in abnormal intestinal flora of rat caused by high-fat high-starch diet. In addition, strain CCFM8631 of *Lactobacillus reuteri* has pretty good tolerance to simulated gastrointestinal fluid, and quickly colonizes in intestinal, significantly alleviates pathology damages of tissues, such as liver, duodenum and so on of rat with metabolic syndrome caused by high-fat high-starch diet; significantly improves oral glucose tolerance of rat with metabolic syndrome and decreases the under curve area of glucose tolerance test; significantly increases triglyceride and total cholesterol levels in serum of rat with metabolic syndrome caused by high-fat high-starch diet. The strain CCFM8631 of *Lactobacillus reuteri* of the present disclosure can be used to prepare health foods or medicines that improve metabolic syndrome, regulates intestinal flora, relieves irritable bowel syndrome, regulates brain-gut axis and alleviates mental illness such as anxiety, depression and so on, which has a pretty wide application prospect.

DESCRIPTION OF MICROBIOLOGICAL PRESERVATION

CCFM8631, classification name: *Lactobacillus reuteri*, is deposited at China General Microbiological Culture Collection Center (CGMCC, Address: Beijing Institute of Microbiology, Chinese Academy of Sciences, No. 1, Beichen West Road, Chaoyang District, Beijing, China) on Jul. 7, 2017, with an accession number CGMCC 14394.

BRIEF DESCRIPTION OF DRAWINGS

In order to describe the technical solutions in the examples of the present disclosure or the conventional art more clearly, the accompanying drawings used in description of the embodiments or the prior art will be illustrated briefly.

DETAILED DESCRIPTION

The present disclosure discloses a *Lactobacillus reuteri* and use thereof. One of ordinary skill in the art can learn from the contents herein and improve the process parameters appropriately. In particular, it shall be noted that all the similar substitutions and modifications are apparent to one of ordinary skill in the art and are to be considered within the scope of the present invention. The method and product of the present invention have been described with preferred examples. It is apparent that one of the ordinary skill in the art can make change or modify the combination to the method and product of the present invention without departing from the spirit, scope and spirit of the invention, therefore realizing and applying the techniques of the present invention. www The strain CCFM8631 of *Lactobacillus reuteri* of the present disclosure has the following biology properties.

Figure 1:
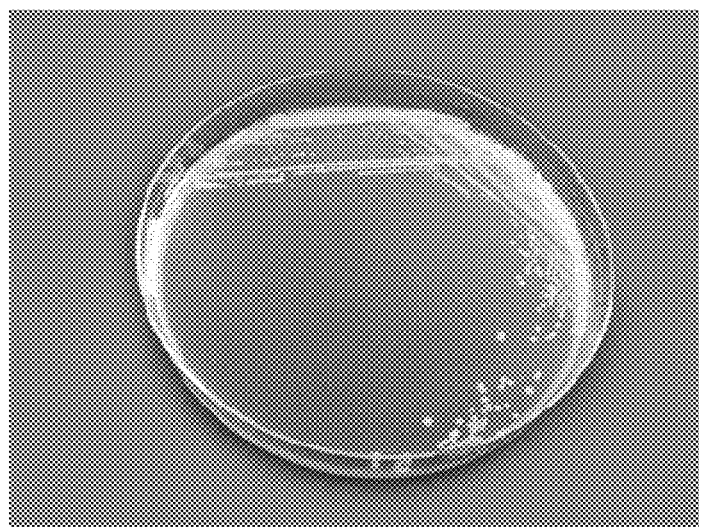
FIG. 1 shows colony morphology of strain CCFM8631 of *Lactobacillus reuteri*.

(1) Bacterium properties: Gram straining positive, slim rod-shape, no flagella, no spore (2) Colony properties: convex colonies are formed after 36-hour culture, the edge is not smooth, the color is milky and non-transparent, the surface is moist and smooth, and no pigment is produce. See FIG. 1.

(3) Growth properties: the bacteria are cultured in MRS medium for about 18 hours at constant temperature of 37° C. to reach log phase.

(4) Good tolerance to simulate gastrointestinal fluid.

(5) Significantly improve pathological tissue damages such as liver, duodenum and so on of rat with from metabolic syndrome.

(6) Significantly improve oral glucose tolerance of rat with metabolic syndrome.

(7) Decrease area under the curve in glucose tolerance test.

(8) Regulate the levels of triglyceride and total cholesterol in serum back to normal level.

(9) Increase 5-hydroxytryptamine (5-HT) level in peripheral blood and regulate testosterone to normal level.

(10) Significantly recover abundances of *Bifidobacterium* genus, *Turicibacter* genus, *Oscillospira* genus, *Blautia* genus and so on in abnormal intestinal flora caused by high-fat high-starch diet.

The strain CCFM8631 of *Lactobacillus reuteri* of the present disclosure is obtained by the following method.

I. Isolation and Screening of *Lactobacillus*

(1) 1 g of fresh feces was diluted in gradient, spreaded on *Lactobacillus* highly selected solid medium plates (0.05 g bromocresol green, 0.02 g vancomycin, 20 g agar per 1 L MRS medium, pH 5.0±0.1), and the plates were incubated at 37° C. for 48-72 hours. The feces were obtained from a 57-year-old healthy female in Changshou Village, Bama Town in Guangxi Province, China.

(2) Morphology of the colonies were observed and recorded, and single colony was picked out and purified by streaking.

(3) The bacteria were cultured at 37° C. for 24 hours in MRS medium, and the colonies obtained were subjected to Gram staining. The morphologies of the colonies were recorded.

(4) The Gram-negative strains and Gram-positive cocci were discarded, the Gram-positive bacilli were selected.

(5) The bacteria were subjected to catalase analyzing, the catalase-positive strains were discarded and catalase-negative strains were retained.

II. Molecular Biological Identification of *Lactobacillus reuteri*

(1) Genome extraction of single bacterium (according to operation procedures of TIANamp Bacteria DNA kit)

A. The *Lactobacillus* obtained in Step I was cultured overnight. 1 mL culture was put into a 1.5 mL centrifuge tube and centrifuged at 10,000 rpm (~11,500×g) for 1 minute. The supernatant was removed as much as possible.

B. 180 μL buffer (20 mg/mL lysozyme solution with 20 mM Tris (pH 8.0), 2 mM $Na_2$-EDTA, and 1.2% Triton) was added to the bacteria and incubated at 37° C. for more than 30 minutes. (The lysozyme solution should be prepared by dissolving lysozyme dry powder in the buffer, or the lysozyme would be inactive.

C. 20 μL Proteinase K solution was added to the tube and mixed well.

D. 220 μL buffer GB was added, shaken for 15 seconds, and placed at 70° C. for 10 minutes. The solution turned clean. The tube was centrifuged for a few seconds to remove water drops on inner wall of the tube.

E. 220 μL absolute alcohol was added adequately shaken for 15 seconds. Flocculent precipitates maybe appear. The tube was centrifuged for a few seconds to remove water drops on inner wall of the tube.

F. The solution and flocculent precipitate obtained in the last step were put into an adsorption column CB3 (the absorption column was disposed in a collecting tube), and subjected to centrifugation at 12,000 rpm (~13,400×g) for 30 seconds. The flow-through liquor was discarded, and the adsorption column was put back into the collecting tube.

G. 500 μL of buffer GD (check for absolute alcohol adding before use) was added to the adsorption column CB3. The column was centrifuged at 12,000 rpm (~13,400×g) for 30 seconds. The flow-through liquor was discarded, and the adsorption column was put back into the collecting tube.

H. 600 μL of washing solution PW (check for absolute alcohol adding before use) was added to the adsorption column CB3. The column was centrifuged at 12,000 rpm (~13,400×g) for 30 seconds. The flow-through liquor was discarded, and the adsorption column was put back into the collecting tube. This step was repeated once.

I. The adsorption column CB3 was put back into the collecting tube, centrifuged at 12,000 rpm (~13,400×g) for 2 minutes, and the flow-through liquor was discarded. The adsorption column CB3 was placed at room temperature for a few minutes to let the adsorption column totally dry.

J. The adsorption column CB3 was transferred to a clean centrifugal tube, and 50 to 200 μL of elution buffer TE was dropped to the middle of the adsorption film. The adsorption column was placed at room temperature for 2 to 5 minutes, and then centrifuged at 12,000 rpm (~13,400×g) for 2 minutes. The eluted solution was collected into a centrifuge tube.

(2) Whole Genome Sequencing

The extracted whole genome was sent to a professional sequencing company and a third-generation sequencer was used to sequence the whole bacterial genome. The sequencing results were subjected to similarity comparison by BLAST software among GeneBank database. The results show that the strain provided by the present disclosure is a *Lactobacillus reuteri*, but different from known *Lactobacillus reuteri*, so that it is identified as a new strain. By blastn algorithm, the genome of strain CCFM8631 of *Lactobacillus reuteri* was compared with that of standard strain DSM20016 of *Lactobacillus reuteri* (https://wwwncbi.nlm.nih.gov/genome/?term=438), 571 genes in total show differences, which are shown in Table 1.

TABLE 1

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0003 | gi\|970364679\|emb\|CUR36395.1\| | oxidoreductase, short chain dehydrogenase/reductase family [*Lactobacillus reuteri*] | 100 | 190 | 0 | 0 | 1 | 570 | 1 | 190 | 6.06E-143 | 394 |
| TBCP-1560_g_0004 | gi\|512154930\|gb\|AGN98213.1\| | short chain dehydrogenase [*Lactobacillus reuteri* I5007] | 100 | 44 | 0 | 0 | 1 | 132 | 1 | 44 | 4.35E-25 | 85.5 |
| TBCP-1560_g_0019 | gi\|970370732\|emb\|CUR40704.1\| | Transcriptional regulator, XRE family [*Lactobacillus reuteri*] | 97.059 | 34 | 1 | 0 | 1 | 102 | 1 | 34 | 1.46E-17 | 69.7 |
| TBCP-1560_g_0020 | gi\|953265103\|emb\|CUU12464.1\| | Insertion sequence IS232 putative ATP-binding protein [*Lactobacillus reuteri* AITCC 53608] | 100 | 245 | 0 | 0 | 1 | 735 | 1 | 245 | 0 | 504 |
| TBCP-1560_g_0023 | gi\|512154946\|gb\|AGN98229.1\| | hypothetical protein LRI_0020 [*Lactobacillus reuteri* I5007] | 100 | 31 | 0 | 0 | 95 | 3 | 7 | 37 | 4.49E-16 | 62 |
| TBCP-1560_g_0038 | gi\|518081627\|ref\|WP_019251835.1\| | sulfurtransferase [*Lactobacillus reuteri*] | 100 | 258 | 0 | 0 | 1 | 774 | 1 | 258 | 0 | 503 |
| TBCP-1560_g_0051 | gi\|948618334\|gb\|KRK50363.1\| | OsmC family protein [*Lactobacillus reuteri* DSM 20016] | 100 | 142 | 0 | 0 | 1 | 426 | 19 | 160 | 3.75E-105 | 296 |
| TBCP-1560_g_0052 | gi\|1017201634\|ref\|WP_063164307.1\| | lactate dehydrogenase [*Lactobacillus reuteri*] | 99.698 | 331 | 1 | 0 | 1 | 993 | 1 | 331 | 0 | 644 |
| TBCP-1560_g_0054 | gi\|489766316\|ref\|WP_003670244.1\| | hypothetical protein [*Lactobacillus reuteri*] | 100 | 73 | 0 | 0 | 1 | 219 | 1 | 73 | 3.14E-41 | 128 |
| TBCP-1560_g_0069 | gi\|489771585\|ref\|WP_003675493.1\| | GTP pyrophosphokinase [*Lactobacillus reuteri*] | 100 | 206 | 0 | 0 | 1 | 618 | 1 | 206 | 1.73E-156 | 430 |
| TBCP-1560_g_0080 | gi\|489771566\|ref\|WP_003675474.1\| | guanosine monophosphate reductase [*Lactobacillus reuteri*] | 100 | 324 | 0 | 0 | 1 | 972 | 1 | 324 | 0 | 674 |
| TBCP-1560_g_0084 | gi\|489771562\|ref\|WP_003675470.1\| | hypothetical protein [*Lactobacillus reuteri*] | 100 | 128 | 0 | 0 | 1 | 384 | 1 | 128 | 3.65E-93 | 263 |
| TBCP-1560_g_0095 | gi\|489771550\|ref\|WP_003675458.1\| | carbamoyl phosphate synthase large subunit [*Lactobacillus reuteri*] | 100 | 1056 | 0 | 0 | 1 | 3168 | 1 | 1056 | 0 | 2122 |
| TBCP-1560_g_0109 | gi\|489771532\|ref\|WP_003675440.1\| | DNA-binding response regulator [*Lactobacillus reuteri*] | 100 | 226 | 0 | 0 | 1 | 678 | 1 | 226 | 5.55E-155 | 428 |
| TBCP-1560_g_0114 | gi\|489771525\|ref\|WP_003675433.1\| | transcriptional regulator [*Lactobacillus reuteri*] | 100 | 197 | 0 | 0 | 1 | 591 | 1 | 197 | 4.60E-149 | 410 |
| TBCP-1560_g_0115 | gi\|489771524\|ref\|WP_003675432.1\| | hypothetical protein [*Lactobacillus reuteri*] | 100 | 226 | 0 | 0 | 1 | 678 | 1 | 226 | 6.77E-170 | 466 |
| TBCP-1560_g_0116 | gi\|489771523\|ref\|WP_003675431.1\| | NAD-dependent protein deacetylase [*Lactobacillus reuteri*] | 100 | 324 | 0 | 0 | 1 | 972 | 1 | 324 | 0 | 645 |
| TBCP-1560_g_0120 | gi\|512155047\|gb\|AGN98330.1\| | acetyltransferase [*Lactobacillus reuteri* I5007] | 100 | 176 | 0 | 0 | 1 | 528 | 1 | 176 | 1.40E-111 | 314 |
| TBCP-1560_g_0121 | gi\|489761202\|ref\|WP_003665145.1\| | hypothetical protein [*Lactobacillus reuteri*] | 98.507 | 67 | 1 | 0 | 1 | 201 | 1 | 67 | 1.44E-44 | 136 |
| TBCP-1560_g_0122 | gi\|489771517\|ref\|WP_003675425.1\| | cell surface protein [*Lactobacillus reuteri*] | 100 | 286 | 0 | 0 | 1 | 858 | 1 | 286 | 0 | 584 |
| TBCP-1560_g_0123 | gi\|737175530\|ref\|WP_035161724.1\| | phenolic acid decarboxylase padC [*Lactobacillus reuteri*] | 100 | 179 | 0 | 0 | 1 | 537 | 1 | 179 | 3.28E-134 | 371 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0125 | gi\|337728644\|emb\|CCC03755.1\| | putative NAD binding protein, possible epimerase/dehydratase [*Lactobacillus reuteri* ATCC 53608] | 100 | 208 | 0 | 0 | 1 | 624 | 1 | 208 | 7.71E-155 | 426 |
| TBCP-1560_g_0134 | gi\|512738680\|refWP_016496408.1\| | NADH-flavin reductase-like protein [*Lactobacillus reuteri*] | 100 | 214 | 0 | 0 | 1 | 642 | 1 | 214 | 5.25E-162 | 444 |
| TBCP-1560_g_0135 | gi\|489765480\|refWP_003669411.1\| | HesB/YadR/YfhF-family protein [*Lactobacillus reuteri*] | 100 | 120 | 0 | 0 | 1 | 360 | 4 | 123 | 1.08E-87 | 249 |
| TBCP-1560_g_0136 | gi\|489765479\|refWP_003669410.1\| | glutamine amidotransferase [*Lactobacillus reuteri*] | 100 | 223 | 0 | 0 | 1 | 669 | 1 | 223 | 5.25E-170 | 466 |
| TBCP-1560_g_0139 | gi\|489771502\|refWP_003675410.1\| | diguanylate phosphodiesterase [*Lactobacillus reuteri*] | 100 | 211 | 0 | 0 | 1 | 633 | 1 | 211 | 2.57E-158 | 436 |
| TBCP-1560_g_0148 | gi\|512738689\|refWP_016496417.1\| | hypothetical protein [*Lactobacillus reuteri*] | 95.652 | 115 | 5 | 0 | 1 | 345 | 1 | 115 | 6.55E-67 | 207 |
| TBCP-1560_g_0154 | gi\|518083879\|refWP_019254087.1\| | NAD-dependent dehydratase [*Lactobacillus reuteri*] | 100 | 48 | 0 | 0 | 1 | 144 | 1 | 48 | 6.74E-29 | 100 |
| TBCP-1560_g_0156 | gi\|489771478\|refWP_003675387.1\| | GCN5 family N-acetyltransferase [*Lactobacillus reuteri*] | 100 | 145 | 0 | 0 | 1 | 435 | 1 | 145 | 3.98E-108 | 303 |
| TBCP-1560_g_0158 | gi\|489761160\|refWP_003665104.1\| | cytochrome b5 [*Lactobacillus reuteri*] | 100 | 72 | 0 | 0 | 1 | 216 | 1 | 72 | 2.40E-47 | 143 |
| TBCP-1560_g_0159 | gi\|489771474\|refWP_003675383.1\| | cytochrome b5 [*Lactobacillus reuteri*] | 100 | 81 | 0 | 0 | 1 | 243 | 1 | 81 | 3.19E-57 | 169 |
| TBCP-1560_g_0161 | gi\|337728616\|emb\|CCC03724.1\| | hypothetical protein LRATCC53608_0972 [*Lactobacillus reuteri* ATCC 53608] | 100 | 38 | 0 | 0 | 1 | 114 | 1 | 38 | 6.70E-21 | 74.7 |
| TBCP-1560_g_0180 | gi\|489771454\|refWP_003675363.1\| | TetR family transcriptional regulator [*Lactobacillus reuteri*] | 100 | 170 | 0 | 0 | 1 | 510 | 1 | 170 | 3.30E-127 | 353 |
| TBCP-1560_g_0184 | gi\|489771446\|refWP_003675355.1\| | hypothetical protein [*Lactobacillus reuteri*] | 100 | 78 | 0 | 0 | 1 | 234 | 1 | 78 | 2.35E-55 | 164 |
| TBCP-1560_g_0190 | gi\|489771434\|refWP_003675343.1\| | hypothetical protein [*Lactobacillus reuteri*] | 100 | 206 | 0 | 0 | 1 | 618 | 1 | 206 | 5.91E-156 | 429 |
| TBCP-1560_g_0192 | gi\|489771430\|refWP_003675339.1\| | histidine--tRNA ligase [*Lactobacillus reuteri*] | 100 | 425 | 0 | 0 | 1 | 1275 | 1 | 425 | 0 | 836 |
| TBCP-1560_g_0197 | gi\|227186376\|gb\|EEI66447.1\| | hypothetical protein HMPREF0534_0218 [*Lactobacillus reuteri* CF48-3A] | 94.231 | 52 | 3 | 0 | 1 | 156 | 1 | 52 | 1.84E-30 | 99.8 |
| TBCP-1560_g_0199 | gi\|489765400\|refWP_003669331.1\| | hypothetical protein [*Lactobacillus reuteri*] | 99.541 | 218 | 1 | 0 | 1 | 654 | 1 | 218 | 1.28E-165 | 454 |
| TBCP-1560_g_0200 | gi\|526246046\|refWP_020843400.1\| | hypothetical protein [*Lactobacillus reuteri*] | 100 | 39 | 0 | 0 | 1 | 117 | 1 | 39 | 4.20E-17 | 67 |
| TBCP-1560_g_0208 | gi\|512155129\|gb\|AGN98412.1\| | C4-dicarboxylate anaerobic carrier [*Lactobacillus reuteri* I5007] | 98.592 | 71 | 1 | 0 | 1 | 213 | 1 | 71 | 2.23E-48 | 146 |
| TBCP-1560_g_0216 | gi\|489771396\|refWP_003675305.1\| | RNA pseudouridine synthase [*Lactobacillus reuteri*] | 100 | 306 | 0 | 0 | 1 | 918 | 1 | 306 | 0 | 630 |
| TBCP-1560_g_0217 | gi\|526246038\|refWP_020843392.1\| | membrane protein [*Lactobacillus reuteri*] | 99.203 | 251 | 2 | 0 | 1 | 753 | 1 | 251 | 5.51E-174 | 478 |
| TBCP-1560_g_0220 | gi\|512738724\|refWP_016496451.1\| | signal peptide [*Lactobacillus reuteri*] | 99.914 | 1166 | 1 | 0 | 1 | 3498 | 1 | 1166 | 0 | 2135 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0227 | gi\|1017201665\|ref\|WP_063164338.1\| | patatin family protein [*Lactobacillus reuteri*] | 100 | 74 | 0 | 0 | 1 | 222 | 1 | 74 | 2.62E-50 | 151 |
| TBCP-1560_g_0229 | gi\|754210084\|ref\|WP_041821572.1\| | hypothetical protein [*Lactobacillus reuteri*] | 100 | 100 | 0 | 0 | 1 | 300 | 1 | 100 | 2.00E-70 | 204 |
| TBCP-1560_g_0231 | gi\|489771374\|ref\|WP_003675283.1\| | membrane protein [*Lactobacillus reuteri*] | 99.614 | 259 | 1 | 0 | 1 | 777 | 1 | 259 | 0 | 535 |
| TBCP-1560_g_0237 | gi\|512155158\|gb\|AGN98441.1\| | hypothetical protein LRI_0232 [*Lactobacilitis reuteri* I5007] | 100 | 61 | 0 | 0 | 1 | 183 | 1 | 61 | 2.47E-41 | 127 |
| TBCP-1560_g_0240 | gi\|489761065\|ref\|WP_003665009.1\| | hypothetical protein [*Lactobacillus reuteri*] | 100 | 106 | 0 | 0 | 1 | 318 | 1 | 106 | 3.15E-76 | 219 |
| TBCP-1560_g_0241 | gi\|970363723\|emb\|CUR37285.1\| | Glutathione-regulated potassium-efflux system ancillary protein KefG [*Lactobacillus reuteri*] | 100 | 227 | 0 | 0 | 1 | 681 | 1 | 227 | 3.80E-149 | 413 |
| TBCP-1560_g_0242 | gi\|337728551\|emb\|CCC03657.1\| | hypothetical protein LRATCC53608_0905 [*Lactobacillus reuteri* AITCC 53608] | 100 | 57 | 0 | 0 | 1 | 171 | 1 | 57 | 5.59E-38 | 119 |
| TBCP-1560_g_0245 | gi\|489771350\|ref\|WP_003675259.1\| | ATPase [*Lactobacillus reuteri*] | 99.738 | 381 | 1 | 0 | 1 | 1143 | 1 | 381 | 0 | 771 |
| TBCP-1560_g_0246 | gi\|489771348\|ref\|WP_003675257.1\| | peptidase [*Lactobacillus reuteri*] | 99.535 | 430 | 2 | 0 | 1 | 1290 | 1 | 430 | 0 | 850 |
| TBCP-1560_g_0248 | gi\|489771344\|ref\|WP_003675253.1\| | peptidase M13 [*Lactobacillus reuteri*] | 99.685 | 634 | 2 | 0 | 1 | 1902 | 1 | 634 | 0 | 1298 |
| TBCP-1560_g_0249 | gi\|512738735\|ref\|WP_016496462.1\| | transcriptional regulator [*Lactobacillus reuteri*] | 99.528 | 212 | 1 | 0 | 1 | 636 | 1 | 212 | 5.98E-157 | 432 |
| TBCP-1560_g_0250 | gi\|489771340\|ref\|WP_003675249.1\| | RNase III inhibitor [*Lactobacillus reuteri*] | 99.401 | 167 | 1 | 0 | 1 | 501 | 1 | 167 | 2.83E-124 | 345 |
| TBCP-1560_g_0255 | gi\|512156691\|gb\|AGN99974.1\| | transposase [*Lactobacillus reuteri* I5007] | 96.552 | 29 | 1 | 0 | 1 | 87 | 14 | 42 | 1.86E-15 | 60.5 |
| TBCP-1560_g_0276 | gi\|970366323\|emb\|CUR42817.1\| | Proton/glutamate symport protein @ Sodium/glutamate symport protein [*Lactobacillus reuteri*] | 99.771 | 437 | 1 | 0 | 1 | 1311 | 1 | 437 | 0 | 842 |
| TBCP-1560_g_0279 | gi\|512738751\|ref\|WP_016496478.1\| | low temperature requirement protein LtrA [*Lactobacillus reuteri*] | 100 | 123 | 0 | 0 | 4 | 372 | 2 | 124 | 1.04E-86 | 247 |
| TBCP-1560_g_0280 | gi\|489765927\|ref\|WP_003669856.1\| | hypothetical protein [*Lactobacillus reuteri*] | 100 | 175 | 0 | 0 | 1 | 525 | 35 | 209 | 1.27E-113 | 320 |
| TBCP-1560_g_0291 | gi\|512738759\|ref\|WP_016496485.1\| | ABC transporter ATP-binding protein [*Lactobacillus reuteri*] | 99.303 | 287 | 2 | 0 | 1 | 861 | 1 | 287 | 0 | 586 |
| TBCP-1560_g_0292 | gi\|337728515\|emb\|CCC03619.1\| | hypothetical protein LRATCC53608_0867 [*Lactobacillus reuteri* AITCC 53608] | 99.425 | 174 | 1 | 0 | 1 | 522 | 5 | 178 | 1.84E-127 | 354 |
| TBCP-1560_g_0293 | gi\|659900074\|gb\|KEK14882.1\| | hypothetical protein LR3_04370 [*Lactobacillus reuteri*] | 100 | 193 | 0 | 0 | 1 | 579 | 1 | 193 | 1.28E-122 | 343 |
| TBCP-1560_g_0294 | gi\|489760987\|ref\|WP_003664931.1\| | MarR family transcriptional regulator [*Lactobacillus reuteri*] | 99.333 | 150 | 1 | 0 | 1 | 450 | 1 | 150 | 1.06E-107 | 302 |
| TBCP-1560_g_0295 | gi\|489765628\|ref\|WP_003669212.1\| | hypothetical protein [*Lactobacillus reuteri*] | 100 | 241 | 0 | 0 | 1 | 723 | 1 | 241 | 6.83E-175 | 479 |
| TBCP-1560_g_0298 | gi\|754210095\|ref\|WP_041821582.1\| | hypothetical protein [*Lactobacillus reuteri*] | 99.333 | 300 | 2 | 0 | 1 | 900 | 12 | 311 | 0 | 506 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0300 | gi\|489760978\|ref\|WP_003664922.1\| | glycerol transporter [*Lactobacillus reuteri*] | 100 | 235 | 0 | 0 | 1 | 705 | 1 | 235 | 2.25E-169 | 465 |
| TBCP-1560_g_0302 | gi\|512738768\|ref\|WP_016496494.1\| | ABC transporter-like protein [*Lactobacillus reuteri*] | 99.655 | 580 | 2 | 0 | 1 | 1740 | 1 | 580 | 0 | 1146 |
| TBCP-1560_g_0307 | gi\|489771190\|ref\|WP_003675099.1\| | GntR family transcriptional regulator [*Lactobacillus reuteri*] | 100 | 243 | 0 | 0 | 1 | 729 | 1 | 243 | 1.74E-179 | 491 |
| TBCP-1560_g_0308 | gi\|489771188\|ref\|WP_003675097.1\| | phosphoketolase [*Lactobacillus reuteri*] | 100 | 803 | 0 | 0 | 1 | 2409 | 1 | 803 | 0 | 1671 |
| TBCP-1560_g_0311 | gi\|489771184\|ref\|WP_003675093.1\| | alpha/beta hydrolase [*Lactobacillus reuteri*] | 100 | 248 | 0 | 0 | 1 | 744 | 1 | 248 | 0 | 509 |
| TBCP-1560_g_0313 | gi\|489771181\|ref\|WP_003675090.1\| | transcriptional regulator [*Lactobacillus reuteri*] | 100 | 300 | 0 | 0 | 1 | 900 | 1 | 300 | 0 | 595 |
| TBCP-1560_g_0316 | gi\|489771178\|ref\|WP_003675087.1\| | lipoate-protein ligase A [*Lactobacillus reuteri*] | 100 | 337 | 0 | 0 | 1 | 1011 | 1 | 337 | 0 | 699 |
| TBCP-1560_g_0318 | gi\|489765148\|ref\|WP_003669080.1\| | hypothetical protein [*Lactobacillus reuteri*] | 100 | 152 | 0 | 0 | 1 | 456 | 1 | 152 | 9.65E-111 | 310 |
| TBCP-1560_g_0320 | gi\|489771175\|ref\|WP_003675084.1\| | PTS galactitol transporter subunit IIC [*Lactobacillus reuteri*] | 100 | 470 | 0 | 0 | 1 | 1410 | 1 | 470 | 0 | 895 |
| TBCP-1560_g_0324 | gi\|737175460\|ref\|WP_035161655.1\| | alpha/beta hydrolase [*Lactobacillus reuteri*] | 99.693 | 326 | 1 | 0 | 1 | 978 | 1 | 326 | 0 | 634 |
| TBCP-1560_g_0325 | gi\|489760939\|ref\|WP_003664884.1\| | membrane protein [*Lactobacillus reuteri*] | 100 | 118 | 0 | 0 | 1 | 354 | 1 | 118 | 6.50E-68 | 199 |
| TBCP-1560_g_0334 | gi\|489771154\|ref\|WP_003675063.1\| | ferredoxin--NADP(+) reductase [*Lactobacillus reuteri*] | 100 | 332 | 0 | 0 | 1 | 996 | 1 | 332 | 0 | 681 |
| TBCP-1560_g_0346 | gi\|489765111\|ref\|WP_003669043.1\| | spermidine/putrescine ABC transporter permease [*Lactobacillus reuteri*] | 100 | 272 | 0 | 0 | 1 | 816 | 1 | 272 | 0 | 516 |
| TBCP-1560_g_0347 | gi\|489771138\|ref\|WP_003675047.1\| | spermidine/putrescine ABC transporter substrate-binding protein [*Lactobacillus reuteri*] | 100 | 357 | 0 | 0 | 1 | 1071 | 1 | 357 | 0 | 687 |
| TBCP-1560_g_0352 | gi\|489771133\|ref\|WP_003675042.1\| | guanylate kinase [*Lactobacillus reuteri*] | 100 | 190 | 0 | 0 | 1 | 570 | 1 | 190 | 4.51E-143 | 395 |
| TBCP-1560_g_0354 | gi\|489760888\|ref\|WP_003664833.1\| | hypothetical protein [*Lactobacillus reuteri*] | 99.206 | 126 | 1 | 0 | 1 | 378 | 1 | 126 | 4.36E-46 | 147 |
| TBCP-1560_g_0361 | gi\|953264637\|emb\|CUU11948.1\| | CsbD family protein [*Lactobacillus reuteri* ATCC 53608] | 100 | 61 | 0 | 0 | 1 | 183 | 1 | 61 | 1.12E-08 | 45.4 |
| TBCP-1560_g_0370 | gi\|489771105\|ref\|WP_003675014.1\| | type I pantothenate kinase [*Lactobacillus reuteri*] | 100 | 307 | 0 | 0 | 1 | 921 | 1 | 307 | 0 | 630 |
| TBCP-1560_g_0380 | gi\|337728374\|emb\|CCC03475.1\| | conserved hypothetical protein [*Lactobacillus reuteri* ATCC 53608] | 100 | 204 | 0 | 0 | 1 | 612 | 4 | 207 | 4.94E-152 | 419 |
| TBCP-1560_g_0381 | gi\|489760823\|ref\|WP_003664768.1\| | peptidase M10 [*Lactobacillus reuteri*] | 100 | 231 | 0 | 0 | 1 | 693 | 1 | 231 | 2.95E-138 | 386 |
| TBCP-1560_g_0384 | gi\|194454116\|gb\|EDX43013.1\| | hypothetical protein Lreu23DRAFT_4532 [*Lactobacillus reuteri* 100-23] | 92.683 | 41 | 3 | 0 | 1 | 123 | 1 | 41 | 2.22E-22 | 78.6 |
| TBCP-1560_g_0387 | gi\|512155310\|gb\|AGN98593.1\| | membrane protein [*Lactobacillus reuteri* I5007] | 100 | 369 | 0 | 0 | 1 | 1107 | 1 | 369 | 0 | 515 |
| TBCP-1560_g_0388 | gi\|489760812\|ref\|WP_003664757.1\| | elongation factor P [*Lactobacillus reuteri*] | 100 | 185 | 0 | 0 | 1 | 555 | 1 | 185 | 3.22E-136 | 377 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0389 | gi\|489760811\|ref\|WP_003664756.1\| | hypothetical protein [*Lactobacillus reuteri*] | 97.714 | 350 | 8 | 0 | 1 | 1050 | 1 | 350 | 0 | 573 |
| TBCP-1560_g_0394 | gi\|970366169\|emb\|CUR43008.1\| | FIG00746573: hypothetical protein [*Lactobacillus reuteri*] | 100 | 338 | 0 | 0 | 1 | 1014 | 1 | 338 | 0 | 699 |
| TBCP-1560_g_0396 | gi\|737167860\|ref\|WP_035154108.1\| | hypothetical protein [*Lactobacillus reuteri*] | 89.313 | 131 | 14 | 0 | 1 | 393 | 1 | 131 | 1.12E-84 | 242 |
| TBCP-1560_g_0399 | gi\|1016922202\|gb\|AMY14452.1\| | phosphate ABC transporter substrate-binding protein [*Lactobacillus reuteri*] | 100 | 290 | 0 | 0 | 1 | 870 | 1 | 290 | 0 | 591 |
| TBCP-1560_g_0400 | gi\|489771084\|ref\|WP_003674993.1\| | phosphate ABC transporter permease sub unit PstC [*Lactobacillus reuteri*] | 99.666 | 299 | 1 | 0 | 1 | 897 | 1 | 299 | 0 | 530 |
| TBCP-1560_g_0403 | gi\|2271844997\|gb\|EEI65068.1\| | phosphate transport system regulatory protein PhoU [*Lactobacillus reuteri* CF48-3A] | 100 | 234 | 0 | 0 | 1 | 702 | 10 | 243 | 4.44E-174 | 477 |
| TBCP-1560_g_0405 | gi\|970368823\|emb\|CUR38312.1\| | FIG00748601: hypothetical protein [*Lactobacillus reuteri*] | 100 | 287 | 0 | 0 | 1 | 861 | 1 | 287 | 0 | 578 |
| TBCP-1560_g_0406 | gi\|512155320\|gb\|AGN98603.1\| | hypothetical protein LRI_0394 [*Lactobacillus reuteri* I5007] | 100 | 48 | 0 | 0 | 1 | 144 | 1 | 48 | 3.21E-28 | 93.6 |
| TBCP-1560_g_0407 | gi\|512155322\|gb\|AGN98604.1\| | glycosyl transferase family protein [*Lactobacillus reuteri* I5007] | 100 | 227 | 0 | 0 | 1 | 681 | 1 | 227 | 1.65E-160 | 442 |
| TBCP-1560_g_0410 | gi\|512155324\|gb\|AGN98607.1\| | glycosyltransferase [*Lactobacillus reuteri* I5007] | 100 | 191 | 0 | 0 | 1 | 573 | 1 | 191 | 5.67E-120 | 337 |
| TBCP-1560_g_0411 | gi\|512738819\|ref\|WP_016496544.1\| | glycoside hydrolase [*Lactobacillus reuteri*] | 100 | 379 | 0 | 0 | 1 | 1137 | 1 | 379 | 0 | 798 |
| TBCP-1560_g_0414 | gi\|512738822\|ref\|WP_016496547.1\| | potassium uptake protein [*Lactobacillus reuteri*] | 99.776 | 447 | 1 | 0 | 1 | 1341 | 1 | 447 | 0 | 823 |
| TBCP-1560_g_0416 | gi\|970368831\|emb\|CUR38320.1\| | FIG00748017: hypothetical protein [*Lactobacillus reuteri*] | 100 | 164 | 0 | 0 | 52 | 543 | 18 | 181 | 7.57E-118 | 330 |
| TBCP-1560_g_0420 | gi\|970367179\|emb\|CUR39802.1\| | Cystathionine beta-synthase [*Lactobacillus reuteri*] | 100 | 304 | 0 | 0 | 1 | 912 | 1 | 304 | 0 | 531 |
| TBCP-1560_g_0423 | gi\|970367177\|emb\|CUR39800.1\| | Inner membrane protein [*Lactobacillus reuteri*] | 100 | 339 | 0 | 0 | 1 | 1017 | 4 | 342 | 0 | 585 |
| TBCP-1560_g_0425 | gi\|512738831\|ref\|WP_016496555.1\| | esterase [*Lactobacillus reuteri*] | 100 | 238 | 0 | 0 | 1 | 714 | 1 | 238 | 4.41E-180 | 492 |
| TBCP-1560_g_0430 | gi\|489771049\|ref\|WP_003674958.1\| | hypothetical protein [*Lactobacillus reuteri*] | 100 | 444 | 0 | 0 | 1 | 1332 | 1 | 444 | 0 | 917 |
| TBCP-1560_g_0431 | gi\|489771047\|ref\|WP_003674956.1\| | MFS transporter permease [*Lactobacillus reuteri*] | 100 | 405 | 0 | 0 | 1 | 1215 | 1 | 405 | 0 | 664 |
| TBCP-1560_g_0435 | gi\|512155348\|gb\|AGN98631.1\| | D-alanyl-D-alanine carboxypeptidase [*Lactobacillus reuteri* I5007] | 100 | 417 | 0 | 0 | 1 | 1251 | 1 | 417 | 0 | 768 |
| TBCP-1560_g_0440 | gi\|512738842\|ref\|WP_016496566.1\| | transposase [*Lactobacillus reuteri*] | 100 | 386 | 0 | 0 | 1 | 1158 | 1 | 386 | 0 | 806 |
| TBCP-1560_g_0441 | gi\|953264694\|emb\|CUU12019.1\| | hypothetical protein LRATCC53608_0483 [*Lactobacillus reuteri* ATCC 53608] | 99.643 | 561 | 2 | 0 | 1 | 1683 | 1 | 561 | 0 | 1136 |
| TBCP-1560_g_0443 | gi\|489771033\|ref\|WP_003674942.1\| | peptidyl-prolyl cis-trans isomerase [*Lactobacillus reuteri*] | 100 | 186 | 0 | 0 | 1 | 558 | 1 | 186 | 3.90E-128 | 357 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0445 | gi\|1017201710\|ref\|WP_063164383.1\| | NAD-dependent malic enzyme [*Lactobacillus reuteri*] | 100 | 542 | 0 | 0 | 1 | 1626 | 1 | 542 | 0 | 1083 |
| TBCP-1560_g_0447 | gi\|489771029\|ref\|WP_003674938.1\| | flavocytochrome c [*Lactobacillus reuteri*] | 100 | 464 | 0 | 0 | 1 | 1392 | 1 | 464 | 0 | 944 |
| TBCP-1560_g_0450 | gi\|2271185979\|gb\|EEI66050.1\| | putative sugar-binding domain protein [*Lactobacillus reuteri* CF48-3A] | 98.403 | 313 | 5 | 0 | 1 | 939 | 55 | 367 | 0 | 641 |
| TBCP-1560_g_0452 | gi\|2271185977\|gb\|EEI66048.1\| | [citrate (pro-3S)-lyase] ligase [*Lactobacillus reuteri* CF48-3A] | 99.424 | 347 | 2 | 0 | 1 | 1041 | 13 | 359 | 0 | 712 |
| TBCP-1560_g_0453 | gi\|489766774\|ref\|WP_003670701.1\| | citrate lyase ACP [*Lactobacillus reuteri*] | 100 | 97 | 0 | 0 | 1 | 291 | 1 | 97 | 3.27E-67 | 196 |
| TBCP-1560_g_0454 | gi\|489766772\|ref\|WP_003670699.1\| | citrate (pro-3S)-lyase subunit beta [*Lactobacillus reuteri*] | 100 | 301 | 0 | 0 | 1 | 903 | 1 | 301 | 0 | 598 |
| TBCP-1560_g_0456 | gi\|518082469\|ref\|WP_019252677.1\| | triphosphoribosyl-dephospho-CoA synthase [*Lactobacillus reuteri*] | 98.737 | 475 | 6 | 0 | 1 | 1425 | 1 | 475 | 0 | 966 |
| TBCP-1560_g_0457 | gi\|518082470\|ref\|WP_019252678.1\| | hydrolase [*Lactobacillus reuteri*] | 98.099 | 263 | 5 | 0 | 1 | 789 | 1 | 263 | 0 | 538 |
| TBCP-1560_g_0459 | gi\|489760694\|ref\|WP_003664640.1\| | LysR family transcriptional regulator [*Lactobacillus reuteri*] | 100 | 295 | 0 | 0 | 1 | 885 | 1 | 295 | 0 | 599 |
| TBCP-1560_g_0460 | gi\|489766772\|ref\|WP_003649171\| | membrane protein [*Lactobacillus reuteri*] | 99.341 | 455 | 3 | 0 | 1 | 1365 | 1 | 455 | 0 | 782 |
| TBCP-1560_g_0461 | gi\|737167582\|ref\|WP_035153834.1\| | uracil-DNA glycosylase [*Lactobacillus reuteri*] | 99.078 | 217 | 2 | 0 | 1 | 651 | 1 | 217 | 2.67E-161 | 443 |
| TBCP-1560_g_0463 | gi\|489771024\|ref\|WP_003674933.1\| | alpha/beta hydrolase [*Lactobacillus reuteri*] | 99.694 | 327 | 1 | 0 | 1 | 981 | 1 | 327 | 0 | 679 |
| TBCP-1560_g_0466 | gi\|336448233\|gb\|AEI56848.1\| | pseudouridine synthase, RluA family [*Lactobacillus reuteri* SD2112] | 100 | 290 | 0 | 0 | 1 | 870 | 26 | 315 | 0 | 604 |
| TBCP-1560_g_0469 | gi\|489764899\|ref\|WP_003668831.1\| | MerR family transcriptional regulator [*Lactobacillus reuteri*] | 100 | 148 | 0 | 0 | 1 | 444 | 1 | 148 | 1.45E-107 | 301 |
| TBCP-1560_g_0470 | gi\|489771016\|ref\|WP_003674926.1\| | hypothetical protein [*Lactobacillus reuteri*] | 99.13 | 115 | 1 | 0 | 1 | 345 | 1 | 115 | 1.63E-82 | 236 |
| TBCP-1560_g_0471 | gi\|489771015\|ref\|WP_003674925.1\| | RNase J family beta-CASP ribonuclease [*Lactobacillus reuteri*] | 100 | 618 | 0 | 0 | 1 | 1854 | 1 | 618 | 0 | 1281 |
| TBCP-1560_g_0472 | gi\|489764104\|emb\|CUR36934.1\| | FIG00743019: hypothetical protein [*Lactobacillus reuteri*] | 100 | 395 | 0 | 0 | 1 | 1185 | 1 | 395 | 0 | 757 |
| TBCP-1560_g_0477 | gi\|489764884\|ref\|WP_003668816.1\| | universal stress protein UspA [*Lactobacillus reuteri*] | 100 | 158 | 0 | 0 | 1 | 474 | 1 | 158 | 2.14E-115 | 322 |
| TBCP-1560_g_0479 | gi\|489771009\|ref\|WP_003674919.1\| | membrane protein [*Lactobacillus reuteri*] | 100 | 230 | 0 | 0 | 1 | 690 | 1 | 230 | 1.11E-144 | 402 |
| TBCP-1560_g_0482 | gi\|489760658\|ref\|WP_003664604.1\| | cold-shock protein [*Lactobacillus reuteri*] | 100 | 66 | 0 | 0 | 1 | 198 | 1 | 66 | 8.39E-44 | 134 |
| TBCP-1560_g_0485 | gi\|489764871\|ref\|WP_003668803.1\| | phosphatase [*Lactobacillus reuteri*] | 100 | 224 | 0 | 0 | 1 | 672 | 1 | 224 | 1.46E-159 | 439 |
| TBCP-1560_g_0486 | gi\|489771002\|ref\|WP_003674912.1\| | N-acetyltransferase GCN5 [*Lactobacillus reuteri*] | 100 | 151 | 0 | 0 | 1 | 453 | 1 | 151 | 9.53E-112 | 312 |
| TBCP-1560_g_0489 | gi\|970366045\|emb\|CUR43096.1\| | membrane protein [*Lactobacillus reuteri*] | 93.627 | 204 | 11 | 1 | 7 | 612 | 34 | 237 | 1.97E-144 | 400 |

TABLE 1-continued

Differential genes between strain CCFM8631 of *Lactobacillus reuteri* and standard strain DSM20016 of *Lactobacillus reuteri*

| Gene ID | mr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0490 | gi\|512155402\|refWP_003664576.1 | membrane protein [*Lactobacillus reuteri* I5007] | 100 | 48 | 0 | 0 | 1 | 144 | 1 | 48 | 4.28E-29 | 101 |
| TBCP-1560_g_0491 | gb\|AGN98685.1\|gi\|512155403 | membrane protein [*Lactobacillus reuteri* I5007] | 100 | 47 | 0 | 0 | 1 | 141 | 1 | 47 | 3.79E-30 | 98.6 |
| TBCP-1560_g_0493 | gb\|AGN98686.1\|gi\|227071188\|gb\|EEI09504.1 | transcriptional repressor of CtsR [*Lactobacillus reuteri* MM2-3] | 100 | 155 | 0 | 0 | 1 | 465 | 13 | 167 | 3.41E-98 | 279 |
| TBCP-1560_g_0500 | gi\|489760630\|refWP_003664576.1 | 30S ribosomal protein S12 [*Lactobacillus reuteri*] | 100 | 139 | 0 | 0 | 1 | 417 | 1 | 139 | 5.65E-88 | 251 |
| TBCP-1560_g_0501 | gi\|489764856\|refWP_003668788.1 | 30S ribosomal protein S7 [*Lactobacillus reuteri*] | 100 | 156 | 0 | 0 | 1 | 468 | 1 | 156 | 1.98E-116 | 325 |
| TBCP-1560_g_0504 | gi\|489760623\|refWP_003664569.1 | 30S ribosomal protein S10 [*Lactobacillus reuteri*] | 100 | 102 | 0 | 0 | 1 | 306 | 1 | 102 | 1.43E-70 | 204 |
| TBCP-1560_g_0505 | gi\|489760621\|refWP_003664567.1 | 50S ribosomal protein L3 [*Lactobacillus reuteri*] | 100 | 219 | 0 | 0 | 1 | 657 | 1 | 219 | 1.69E-148 | 411 |
| TBCP-1560_g_0506 | gi\|489760620\|refWP_003664566.1 | 50S ribosomal protein L4 [*Lactobacillus reuteri*] | 100 | 207 | 0 | 0 | 1 | 621 | 1 | 207 | 1.00E-140 | 390 |
| TBCP-1560_g_0507 | gi\|489760618\|refWP_003664564.1 | 50S ribosomal protein L23 [*Lactobacillus reuteri*] | 100 | 98 | 0 | 0 | 1 | 294 | 1 | 98 | 1.39E-54 | 164 |
| TBCP-1560_g_0508 | gi\|489760617\|refWP_003664563.1 | 50S ribosomal protein L2 [*Lactobacillus reuteri*] | 99.644 | 281 | 1 | 0 | 1 | 843 | 1 | 281 | 0 | 566 |
| TBCP-1560_g_0509 | gi\|489760614 | 30S ribosomal protein S19 [*Lactobacillus reuteri*] | 100 | 92 | 0 | 0 | 1 | 276 | 1 | 92 | 1.12E-64 | 189 |
| TBCP-1560_g_0510 | gi\|489770978\|refWP_003674888.1 | 50S ribosomal protein L22 [*Lactobacillus reuteri*] | 100 | 115 | 0 | 0 | 1 | 345 | 1 | 115 | 4.01E-78 | 224 |
| TBCP-1560_g_0511 | gi\|489770610\|refWP_003664556.1 | 30S ribosomal protein S3 [*Lactobacillus reuteri*] | 99.548 | 221 | 1 | 0 | 1 | 663 | 1 | 221 | 4.35E-147 | 407 |
| TBCP-1560_g_0513 | gi\|489760606\|refWP_003664552.1 | MULTISPECIES: 50S ribosomal protein L29 [*Lactobacillus*] | 100 | 68 | 0 | 0 | 1 | 204 | 1 | 68 | 3.61E-43 | 132 |
| TBCP-1560_g_0514 | gi\|489760605\|refWP_003664551.1 | 30S ribosomal protein S17 [*Lactobacillus reuteri*] | 100 | 88 | 0 | 0 | 1 | 264 | 1 | 88 | 4.82E-61 | 179 |
| TBCP-1560_g_0516 | gi\|489760603\|refWP_003664549.1 | 50S ribosomal protein L24 [*Lactobacillus reuteri*] | 100 | 102 | 0 | 0 | 1 | 306 | 1 | 102 | 3.16E-69 | 201 |
| TBCP-1560_g_0517 | gi\|489764852\|refWP_003668784.1 | 50S ribosomal protein L5 [*Lactobacillus reuteri*] | 100 | 180 | 0 | 0 | 1 | 540 | 1 | 180 | 2.58E-132 | 367 |
| TBCP-1560_g_0518 | gi\|489760600\|refWP_003664546.1 | 30S ribosomal protein S8 [*Lactobacillus reuteri*] | 100 | 132 | 0 | 0 | 1 | 396 | 1 | 132 | 3.69E-94 | 266 |
| TBCP-1560_g_0522 | gi\|489760595\|refWP_003664541.1 | 50S ribosomal protein L30 [*Lactobacillus reuteri*] | 100 | 60 | 0 | 0 | 1 | 180 | 1 | 60 | 9.81E-39 | 121 |
| TBCP-1560_g_0525 | gi\|970368280\|emb\|CUR38822.1 | Adenylate kinase [*Lactobacillus reuteri*] | 100 | 219 | 0 | 0 | 1 | 657 | 1 | 219 | 4.25E-165 | 453 |
| TBCP-1560_g_0526 | gi\|489770966\|refWP_003674876.1 | translation initiation factor IF-1 [*Lactobacillus reuteri*] | 98.611 | 72 | 1 | 0 | 1 | 216 | 1 | 72 | 6.65E-48 | 145 |
| TBCP-1560_g_0527 | gi\|489760589\|refWP_003664535.1 | 50S ribosomal protein L36 [*Lactobacillus reuteri*] | 100 | 39 | 0 | 0 | 1 | 117 | 1 | 39 | 1.68E-22 | 78.6 |
| TBCP-1560_g_0534 | gi\|489770957\|refWP_003674867.1 | cobalt ABC transporter ATP-binding protein [*Lactobacillus reuteri*] | 100 | 267 | 0 | 0 | 1 | 801 | 1 | 267 | 8.36E-167 | 461 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0535 | gi\|489770955\| ref\|WP_003674865.1\| | tRNA pseudouridine(38, 39, 40) synthase TruA [*Lactobacillus reuteri*] | 100 | 256 | 0 | 0 | 1 | 768 | 1 | 256 | 0 | 529 |
| TBCP-1560_g_0537 | gi\|489764839\| ref\|WP_003668771.1\| | 30S ribosomal protein S9 [*Lactobacillus reuteri*] | 100 | 133 | 0 | 0 | 1 | 399 | 1 | 133 | 1.04E-94 | 268 |
| TBCP-1560_g_0540 | gi\|489770952\| ref\|WP_003674862.1\| | acetoin reductase [*Lactobacillus reuteri*] | 99.611 | 257 | 1 | 0 | 1 | 771 | 1 | 257 | 0 | 515 |
| TBCP-1560_g_0542 | gi\|489770949\| ref\|WP_003674859.1\| | xanthine phosphoribosyltransferase [*Lactobacillus reuteri*] | 100 | 191 | 0 | 0 | 1 | 573 | 1 | 191 | 1.21E-129 | 361 |
| TBCP-1560_g_0543 | gi\|489770948\| ref\|WP_003674858.1\| | phosphoribosylaminoimidazole carboxylase [*Lactobacillus reuteri*] | 99.735 | 377 | 1 | 0 | 1 | 1131 | 1 | 377 | 0 | 773 |
| TBCP-1560_g_0544 | gi\|489760563\| ref\|WP_003664509.1\| | ATP-dependent DNA helicase PcrA [*Lactobacillus reuteri*] | 99.868 | 757 | 1 | 0 | 1 | 2271 | 1 | 757 | 0 | 1530 |
| TBCP-1560_g_0546 | gi\|489770944\| ref\|WP_003674854.1\| | CamS family sex pheromone protein [*Lactobacillus reuteri*] | 99.73 | 371 | 1 | 0 | 1 | 1113 | 1 | 371 | 0 | 681 |
| TBCP-1560_g_0547 | gi\|489770942\| ref\|WP_003674852.1\| | asparaginyl/glutamyl-tRNA amidotransferase subunit C [*Lactobacillus reuteri*] | 100 | 105 | 0 | 0 | 1 | 315 | 1 | 105 | 2.86E-73 | 211 |
| TBCP-1560_g_0553 | gi\|489764819\| ref\|WP_003668751.1\| | 23S rRNA (uracil-5-)-methyltransferase RumA [*Lactobacillus reuteri*] | 98.954 | 478 | 5 | 0 | 1 | 1434 | 1 | 478 | 0 | 974 |
| TBCP-1560_g_0560 | gi\|489767756\| ref\|WP_003671680.1\| | preprotein translocase subunit TatB [*Lactobacillus reuteri*] | 89.011 | 91 | 10 | 0 | 1 | 273 | 88 | 178 | 8.68E-56 | 169 |
| TBCP-1560_g_0562 | gi\|489767761\| ref\|WP_003671685.1\| | hypothetical protein [*Lactobacillus reuteri*] | 100 | 103 | 0 | 0 | 1 | 309 | 1 | 103 | 9.66E-63 | 186 |
| TBCP-1560_g_0564 | gi\|512155472\| gb\|AGN98755.1\| | hypothetical protein LRI_0546 [*Lactobacillus reuteri* I5007] | 99.213 | 127 | 1 | 0 | 1 | 381 | 1 | 127 | 3.88E-92 | 261 |
| TBCP-1560_g_0567 | gi\|970364147\| emb\|CUR36896.1\| | Lead, cadmium, zinc and mercury transporting ATPase; Copper-translocating P-type ATPase [*Lactobacillus reuteri*] | 99.21 | 633 | 5 | 0 | 1 | 1899 | 1 | 633 | 0 | 1215 |
| TBCP-1560_g_0568 | gi\|489767767\| ref\|WP_003671691.1\| | MULTISPECIES: copper-binding protein [*Lactobacillus*] | 100 | 76 | 0 | 0 | 1 | 228 | 1 | 76 | 4.09E-51 | 153 |
| TBCP-1560_g_0569 | gi\|489770925\| ref\|WP_003674835.1\| | DNA-binding protein [*Lactobacillus reuteri*] | 100 | 181 | 0 | 0 | 1 | 543 | 1 | 181 | 3.88E-132 | 366 |
| TBCP-1560_g_0570 | gi\|953264799\| emb\|CUU12130.1\| | CRP/FNR family transcriptional regulator [*Lactobacillus reuteri* ATCC 53608] | 99.052 | 211 | 2 | 0 | 1 | 633 | 4 | 214 | 8.52E-154 | 424 |
| TBCP-1560_g_0574 | gi\|512155481\| gb\|AGN98764.1\| | DNA-binding protein [*Lactobacillus reuteri* I5007] | 98.876 | 89 | 1 | 0 | 1 | 267 | 1 | 89 | 3.86E-60 | 177 |
| TBCP-1560_g_0575 | gi\|512155482\| gb\|AGN98765.1\| | DNA-binding protein [*Lactobacillus reuteri* I5007] | 100 | 39 | 0 | 0 | 76 | 192 | 1 | 39 | 3.82E-23 | 81.6 |
| TBCP-1560_g_0583 | gi\|337728224\| emb\|CCC03316.1\| | conserved hypothetical protein [*Lactobacillus reuteri* ATCC 53608] | 100 | 441 | 0 | 0 | 1 | 1323 | 1 | 441 | 0 | 904 |
| TBCP-1560_g_0584 | gi\|489770905\| ref\|WP_003674815.1\| | hypothetical protein [*Lactobacillus reuteri*] | 100 | 237 | 0 | 0 | 1 | 711 | 1 | 237 | 1.80E-179 | 491 |
| TBCP-1560_g_0586 | gi\|489770902\| ref\|WP_003674812.1\| | nitroreductase [*Lactobacillus reuteri*] | 100 | 217 | 0 | 0 | 1 | 651 | 1 | 217 | 1.28E-166 | 456 |
| TBCP-1560_g_0593 | gi\|489770891\| ref\|WP_003674801.1\| | GCN5 family N-acetyltransferase [*Lactobacillus reuteri*] | 100 | 169 | 0 | 0 | 1 | 507 | 1 | 169 | 8.64E-129 | 357 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0596 | gi\|489770885\|ref\|WP_003674795.1\| | N-acetyltransferase GCN5 [*Lactobacillus reuteri*] | 100 | 151 | 0 | 0 | 1 | 453 | 1 | 151 | 9.54E-101 | 285 |
| TBCP-1560_g_0598 | gi\|489770881\|ref\|WP_003674791.1\| | glutamate-cysteine ligase [*Lactobacillus reuteri*] | 100 | 509 | 0 | 0 | 1 | 1527 | 1 | 509 | 0 | 1053 |
| TBCP-1560_g_0600 | gi\|489770878\|ref\|WP_003674788.1\| | Rossman fold protein, TIGR00730 family [*Lactobacillus reuteri*] | 99.476 | 191 | 1 | 0 | 1 | 573 | 1 | 191 | 5.66E-144 | 397 |
| TBCP-1560_g_0604 | gi\|489770875\|ref\|WP_003674785.1\| | helicase [*Lactobacillus reuteri*] | 99.307 | 433 | 3 | 0 | 1 | 1299 | 1 | 433 | 0 | 846 |
| TBCP-1560_g_0609 | gi\|489764752\|ref\|WP_003668684.1\| | type I methionyl aminopeptidase [*Lactobacillus reuteri*] | 100 | 285 | 0 | 0 | 1 | 855 | 1 | 285 | 0 | 524 |
| TBCP-1560_g_0612 | gi\|489770861\|ref\|WP_003674771.1\| | glutamate/gamma-aminobutyrate family transporter YjeM [*Lactobacillus reuteri*] | 99.8 | 501 | 1 | 0 | 1 | 1503 | 1 | 501 | 0 | 945 |
| TBCP-1560_g_0613 | gi\|489770858\|ref\|WP_003674768.1\| | hypothetical protein [*Lactobacillus reuteri*] | 100 | 296 | 0 | 0 | 1 | 888 | 1 | 296 | 0 | 571 |
| TBCP-1560_g_0617 | gi\|489770854\|ref\|WP_003674764.1\| | exopolysaccharide biosynthesis protein [*Lactobacillus reuteri*] | 99.216 | 255 | 2 | 0 | 1 | 765 | 1 | 255 | 0 | 498 |
| TBCP-1560_g_0621 | gi\|489770847\|ref\|WP_003674757.1\| | hypothetical protein [*Lactobacillus reuteri*] | 100 | 473 | 0 | 0 | 1 | 1419 | 1 | 473 | 0 | 915 |
| TBCP-1560_g_0623 | gi\|489770844\|ref\|WP_003674754.1\| | hypothetical protein [*Lactobacillus reuteri*] | 100 | 343 | 0 | 0 | 1 | 1029 | 1 | 343 | 0 | 699 |
| TBCP-1560_g_0625 | gi\|953264848\|emb\|CUU12186.1\| | hypothetical protein predicted by prodigal [*Lactobacillus reuteri* AITCC 53608] | 100 | 41 | 0 | 0 | 1 | 123 | 1 | 41 | 4.54E-22 | 77.8 |
| TBCP-1560_g_0634 | gi\|489770828\|ref\|WP_003674738.1\| | hypothetical protein [*Lactobacillus reuteri*] | 100 | 190 | 0 | 0 | 1 | 570 | 1 | 190 | 8.04E-70 | 209 |
| TBCP-1560_g_0638 | gi\|737169510\|ref\|WP_035155744.1\| | hypothetical protein [*Lactobacillus reuteri*] | 84.314 | 51 | 8 | 0 | 1 | 153 | 351 | 401 | 4.85E-24 | 90.9 |
| TBCP-1560_g_0642 | gi\|526245865\|ref\|WP_020843219.1\| | AI-2E family transporter [*Lactobacillus reuteri*] | 99.731 | 372 | 1 | 0 | 1 | 1116 | 1 | 372 | 0 | 580 |
| TBCP-1560_g_0644 | gi\|489770813\|ref\|WP_003674724.1\| | glycosyl transferase family 2 [*Lactobacillus reuteri*] | 100 | 239 | 0 | 0 | 1 | 717 | 1 | 239 | 1.92E-163 | 450 |
| TBCP-1560_g_0658 | gi\|1017201776\|ref\|WP_063164449.1\| | hypothetical protein [*Lactobacillus reuteri*] | 96.889 | 225 | 7 | 0 | 1 | 675 | 1 | 225 | 3.13E-113 | 322 |
| TBCP-1560_g_0663 | gi\|489770795\|ref\|WP_003674706.1\| | phosphocarrier protein HPr [*Lactobacillus reuteri*] | 100 | 61 | 0 | 0 | 1 | 183 | 1 | 61 | 5.63E-41 | 126 |
| TBCP-1560_g_0664 | gi\|489760395\|ref\|WP_003664342.1\| | glycosyl transferase [*Lactobacillus reuteri*] | 100 | 88 | 0 | 0 | 1 | 264 | 1 | 88 | 2.79E-60 | 177 |
| TBCP-1560_g_0667 | gi\|512738944\|ref\|WP_016496666.1\| | hypothetical protein [*Lactobacillus reuteri*] | 99.708 | 342 | 1 | 0 | 1 | 1026 | 1 | 342 | 0 | 711 |
| TBCP-1560_g_0669 | gi\|489760389\|ref\|WP_003664336.1\| | hypothetical protein [*Lactobacillus reuteri*] | 98.78 | 82 | 1 | 0 | 1 | 246 | 1 | 82 | 3.49E-55 | 164 |
| TBCP-1560_g_0670 | gi\|970368806\|emb\|CUR38328.1\| | FIG00742798: hypothetical protein [*Lactobacillus reuteri*] | 98.913 | 184 | 2 | 0 | 1 | 552 | 1 | 184 | 1.61E-138 | 383 |
| TBCP-1560_g_0674 | gi\|512738946\|ref\|WP_016496668.1\| | anaerobic ribonucleoside triphosphate reductase [*Lactobacillus reuteri*] | 99.866 | 744 | 1 | 0 | 1 | 2232 | 1 | 744 | 0 | 1570 |
| TBCP-1560_g_0675 | gi\|489766847\|ref\|WP_003670774.1\| | anaerobic ribonucleoside-triphosphate reductase activating protein [*Lactobacillus reuteri*] | 99.479 | 192 | 1 | 0 | 1 | 576 | 1 | 192 | 1.08E-144 | 399 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0676 | gi|489771954| ref|WP_003675859.1| | hypothetical protein [*Lactobacillus reuteri*] | 100 | 296 | 0 | 0 | 1 | 888 | 1 | 296 | 0 | 615 |
| TBCP-1560_g_0678 | gi|489771950| ref|WP_003675855.1| | phosphoenolpyruvate carboxykinase [*Lactobacillus reuteri*] | 100 | 566 | 0 | 0 | 1 | 1698 | 1 | 566 | 0 | 1144 |
| TBCP-1560_g_0682 | gi|489760280| ref|WP_003664227.1| | dihydropyrimidine dehydrogenase subunit B [*Lactobacillus reuteri*] | 100 | 432 | 0 | 0 | 1 | 1296 | 1 | 432 | 0 | 900 |
| TBCP-1560_g_0686 | gi|1017201782| ref|WP_063164455.1| | hypothetical protein [*Lactobacillus reuteri*] | 100 | 147 | 0 | 0 | 1 | 441 | 1 | 147 | 1.53E-109 | 306 |
| TBCP-1560_g_0693 | gi|489771933| ref|WP_003675838.1| | 3-methyladenine DNA glycosylase [*Lactobacillus reuteri*] | 100 | 179 | 0 | 0 | 1 | 537 | 1 | 179 | 2.08E-136 | 377 |
| TBCP-1560_g_0697 | gi|512738953| ref|WP_016496675.1| | MOP superfamily multidrug/oligosaccharidyl-lipid/poly saccharide flippase transporter [*Lactobacillus reuteri*] | 100 | 549 | 0 | 0 | 1 | 1647 | 1 | 549 | 0 | 1082 |
| TBCP-1560_g_0699 | gi|970363487| emb|CUR37516.1| | Acetylornithine deacetylase/Succinyl-diaminopimelate desuccinylase and related deacylases [*Lactobacillus reuteri*] | 100 | 463 | 0 | 0 | 1 | 1389 | 5 | 467 | 0 | 949 |
| TBCP-1560_g_0703 | gi|489771917| ref|WP_003675822.1| | hypothetical protein [*Lactobacillus reuteri*] | 100 | 202 | 0 | 0 | 1 | 606 | 1 | 202 | 2.15E-152 | 419 |
| TBCP-1560_g_0704 | gi|489771915| ref|WP_003675820.1| | LacI family transcriptional regulator [*Lactobacillus reuteri*] | 100 | 338 | 0 | 0 | 1 | 1014 | 1 | 338 | 0 | 694 |
| TBCP-1560_g_0706 | gi|489764600| ref|WP_003668533.1| | hypothetical protein [*Lactobacillus reuteri*] | 100 | 81 | 0 | 0 | 1 | 243 | 1 | 81 | 4.84E-54 | 161 |
| TBCP-1560_g_0707 | gi|489771912| ref|WP_003675817.1| | abortive infection protein [*Lactobacillus reuteri*] | 100 | 225 | 0 | 0 | 1 | 675 | 1 | 225 | 1.39E-155 | 429 |
| TBCP-1560_g_0708 | gi|489760247| ref|WP_003664194.1| | hypothetical protein [*Lactobacillus reuteri*] | 100 | 92 | 0 | 0 | 1 | 276 | 1 | 92 | 3.18E-65 | 190 |
| TBCP-1560_g_0710 | gi|489771901| ref|WP_003675807.1| | 2-amino-4-hydroxy-6-hydroxymethyldihydropteridine pyrophosphokinase [*Lactobacillus reuteri*] | 100 | 170 | 0 | 0 | 1 | 510 | 1 | 170 | 3.41E-127 | 353 |
| TBCP-1560_g_0711 | gi|512738959| ref|WP_016496681.1| | GTP cyclohydrolase I FolE [*Lactobacillus reuteri*] | 100 | 192 | 0 | 0 | 1 | 576 | 1 | 192 | 2.48E-145 | 400 |
| TBCP-1560_g_0712 | gi|489771897| ref|WP_003675803.1| | bifunctional folylpolyglutamate synthase/dihydrofolate synthase [*Lactobacillus reuteri*] | 99.761 | 419 | 1 | 0 | 1 | 1257 | 1 | 419 | 0 | 828 |
| TBCP-1560_g_0713 | gi|1017201785| ref|WP_063164458.1| | non-canonical purine NTP pyrophosphatase [*Lactobacillus reuteri*] | 100 | 195 | 0 | 0 | 1 | 585 | 1 | 195 | 1.39E-145 | 401 |
| TBCP-1560_g_0716 | gi|970368862| emb|CUR38275.1| | FIG00745914: hypothetical protein [*Lactobacillus reuteri*] | 96.667 | 90 | 3 | 0 | 1 | 270 | 1 | 90 | 1.02E-48 | 148 |
| TBCP-1560_g_0724 | gi|737170764| ref|WP_035156980.1| | peptidylprolyl isomerase [*Lactobacillus reuteri*] | 99.658 | 292 | 1 | 0 | 1 | 876 | 1 | 292 | 0 | 553 |
| TBCP-1560_g_0727 | gi|489766912| ref|WP_003670839.1| | multidrug ABC transporter ATP-binding protein [*Lactobacillus reuteri*] | 100 | 245 | 0 | 0 | 1 | 735 | 1 | 245 | 0 | 502 |
| TBCP-1560_g_0729 | gi|489760201| ref|WP_003664148.1| | tRNA (guanosine(46)-N7)-methyltransferase TrmB [*Lactobacillus reuteri*] | 99.531 | 213 | 1 | 0 | 1 | 639 | 1 | 213 | 1.20E-146 | 405 |
| TBCP-1560_g_0731 | gi|512155633| gb|AGN98916.1| | YSIRK Gram-positive signal peptide [*Lactobacillus reuteri* I5007] | 100 | 97 | 0 | 0 | 1 | 291 | 1 | 97 | 9.51E-54 | 161 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0732 | gi\|512155634\|gb\|AGN98917.1\| | LPXTG-motif cell wall anchor domain protein [*Lactobacillus reuteri* I5007] | 99.038 | 104 | 1 | 0 | 1 | 312 | 1 | 104 | 6.66E-75 | 218 |
| TBCP-1560_g_0732 | gi\|512155634\|gb\|AGN98917.1\| | LPXTG-motif cell wall anchor domain protein [*Lactobacillus reuteri* I5007] | 100 | 20 | 0 | 0 | 303 | 362 | 102 | 121 | 9.85E-07 | 44.3 |
| TBCP-1560_g_0733 | gi\|337728871\|emb\|CCC03990.1\| | hypothetical protein LRATCC53608_1237 [*Lactobacillus reuteri* ATCC 53608] | 99.877 | 811 | 1 | 0 | 1 | 2433 | 1 | 811 | 0 | 1516 |
| TBCP-1560_g_0740 | ref\|WP_003675765.1\| | tRNA-binding protein [*Lactobacillus reuteri*] | 100 | 215 | 0 | 0 | 1 | 645 | 1 | 215 | 2.70E-159 | 438 |
| TBCP-1560_g_0742 | ref\|WP_003675763.1\| | prevent-host-death family protein [*Lactobacillus reuteri*] | 100 | 97 | 0 | 0 | 1 | 291 | 1 | 97 | 1.50E-67 | 196 |
| TBCP-1560_g_0746 | gi\|1017201790\|ref\|WP_063164463.1\| | DNA polymerase I [*Lactobacillus reuteri*] | 99.887 | 888 | 1 | 0 | 1 | 2664 | 1 | 888 | 0 | 1781 |
| TBCP-1560_g_0747 | gi\|489771849\|ref\|WP_003675755.1\| | DNA-formamidopyrimidine glycosylase [*Lactobacillus reuteri*] | 100 | 276 | 0 | 0 | 1 | 828 | 1 | 276 | 0 | 574 |
| TBCP-1560_g_0748 | gi\|489771847\|ref\|WP_003675753.1\| | dephospho-CoA kinase [*Lactobacillus reuteri*] | 99.497 | 199 | 1 | 0 | 1 | 597 | 1 | 199 | 5.28E-146 | 403 |
| TBCP-1560_g_0749 | gi\|489764556\|ref\|WP_003668489.1\| | NrdR family transcriptional regulator [*Lactobacillus reuteri*] | 98.701 | 154 | 2 | 0 | 1 | 462 | 1 | 154 | 9.09E-112 | 313 |
| TBCP-1560_g_0751 | gi\|489771843\|ref\|WP_003675749.1\| | primosomal protein DnaI [*Lactobacillus reuteri*] | 99.681 | 313 | 1 | 0 | 1 | 939 | 1 | 313 | 0 | 644 |
| TBCP-1560_g_0752 | gi\|489760160\|ref\|WP_003664107.1\| | translation initiation factor IF-3 [*Lactobacillus reuteri*] | 100 | 170 | 0 | 0 | 1 | 510 | 1 | 170 | 1.23E-111 | 313 |
| TBCP-1560_g_0754 | gi\|489771841\|ref\|WP_003675747.1\| | 50S ribosomal protein L20 [*Lactobacillus reuteri*] | 100 | 117 | 0 | 0 | 1 | 351 | 1 | 117 | 6.34E-81 | 232 |
| TBCP-1560_g_0755 | gi\|489771839\|ref\|WP_003675745.1\| | haloacid dehalogenase [*Lactobacillus reuteri*] | 99.432 | 176 | 1 | 0 | 1 | 528 | 1 | 176 | 1.67E-127 | 354 |
| TBCP-1560_g_0757 | gi\|489760152\|ref\|WP_003664099.1\| | RNA-binding protein [*Lactobacillus reuteri*] | 100 | 103 | 0 | 0 | 1 | 309 | 1 | 103 | 1.50E-70 | 204 |
| TBCP-1560_g_0758 | gi\|489771836\|ref\|WP_003675742.1\| | nicotinate-nicotinamide mucleotide adenylyltransferase [*Lactobacillus reuteri*] | 99.533 | 214 | 1 | 0 | 1 | 642 | 1 | 214 | 1.94E-161 | 443 |
| TBCP-1560_g_0759 | gi\|489771834\|ref\|WP_003675740.1\| | HD domain-containing protein [*Lactobacillus reuteri*] | 99.51 | 204 | 1 | 0 | 1 | 612 | 1 | 204 | 1.63E-151 | 417 |
| TBCP-1560_g_0761 | gi\|489771832\|ref\|WP_003675738.1\| | SAM-dependent methyltransferase [*Lactobacillus reuteri*] | 100 | 246 | 0 | 0 | 1 | 738 | 1 | 246 | 0 | 516 |
| TBCP-1560_g_0762 | gi\|337728844\|emb\|CCC03963.1\| | conserved hypothetical protein [*Lactobacillus reuteri* ATCC 53608] | 100 | 377 | 0 | 0 | 1 | 1131 | 1 | 385 | 0 | 732 |
| TBCP-1560_g_0763 | gi\|489760146\|ref\|WP_003664093.1\| | DNA-binding protein [*Lactobacillus reuteri*] | 99.459 | 185 | 1 | 0 | 1 | 555 | 1 | 185 | 6.15E-123 | 343 |
| TBCP-1560_g_0764 | gi\|489760145\|ref\|WP_003664092.1\| | two-component sensor histidine kinase [*Lactobacillus reuteri*] | 100 | 59 | 0 | 0 | 1 | 177 | 1 | 59 | 6.08E-30 | 99 |
| TBCP-1560_g_0767 | gi\|489771827\|ref\|WP_003675733.1\| | 50S ribosomal protein L32 [*Lactobacillus reuteri*] | 100 | 491 | 0 | 0 | 1 | 1473 | 1 | 491 | 0 | 946 |
| TBCP-1560_g_0768 | gi\|489771825\|ref\|WP_003675731.1\| | glutamate/gamma-aminobutyrate family transporter YjeM [*Lactobacillus reuteri*] | 99.799 | 497 | 1 | 0 | 1 | 1491 | 1 | 497 | 0 | 941 |
| TBCP-1560_g_0774 | gi\|489764526\|ref\|WP_003668459.1\| | hydrolase [*Lactobacillus reuteri*] | 100 | 168 | 0 | 0 | 1 | 504 | 1 | 168 | 3.12E-112 | 315 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0775 | gi|489771813| ref|WP_003675719.1| | HxlR family transcriptional regulator [*Lactobacillus reuteri*] | 100 | 112 | 0 | 0 | 1 | 336 | 1 | 112 | 7.83E-81 | 231 |
| TBCP-1560_g_0777 | gi|512738987| ref|WP_016496708.1| | phenylalanine-tRNA ligase subunit beta [*Lactobacillus reuteri*] | 100 | 805 | 0 | 0 | 1 | 2415 | 1 | 805 | 0 | 1626 |
| TBCP-1560_g_0779 | gi|489764516| ref|WP_003668449.1| | uridine kinase [*Lactobacillus reuteri*] | 100 | 218 | 0 | 0 | 1 | 654 | 1 | 218 | 9.30E-115 | 325 |
| TBCP-1560_g_0782 | gi|489771804| ref|WP_003675710.1| | heme biosynthesis protein HemY [*Lactobacillus reuteri*] | 100 | 129 | 0 | 0 | 1 | 387 | 1 | 129 | 1.27E-93 | 265 |
| TBCP-1560_g_0785 | gi|489760102| ref|WP_003664049.1| | MULTISPECIES: 50 S ribosomal protein L33 [*Lactobacillus*] | 100 | 49 | 0 | 0 | 1 | 147 | 1 | 49 | 5.01E-31 | 100 |
| TBCP-1560_g_0786 | gi|489771798| ref|WP_003675704.1| | 5-formyltetrahydrofolate cyclo-ligase [*Lactobacillus reuteri*] | 100 | 184 | 0 | 0 | 1 | 552 | 1 | 184 | 1.27E-137 | 380 |
| TBCP-1560_g_0789 | gi|489764508| ref|WP_003668441.1| | hypothetical protein [*Lactobacillus reuteri*] | 100 | 79 | 0 | 0 | 1 | 237 | 1 | 79 | 1.19E-53 | 160 |
| TBCP-1560_g_0793 | gi|512738993| ref|WP_016496714.1| | tRNA (adenosine(37)-N6)-dimethylallyltransferase MiaA [*Lactobacillus reuteri*] | 100 | 307 | 0 | 0 | 1 | 921 | 1 | 307 | 0 | 635 |
| TBCP-1560_g_0794 | gi|489771787| ref|WP_003675693.1| | type I glutamate--ammonia ligase [*Lactobacillus reuteri*] | 100 | 447 | 0 | 0 | 1 | 1341 | 1 | 447 | 0 | 934 |
| TBCP-1560_g_0797 | gi|194453641| gb|EDX42538.1| | conserved hypothetical protein [*Lactobacillus reuteri* 100-23] | 100 | 41 | 0 | 0 | 1 | 123 | 1 | 41 | 1.43E-22 | 79 |
| TBCP-1560_g_0798 | gi|512738995| ref|WP_016496716.1| | lipoprotein [*Lactobacillus reuteri*] | 99.647 | 283 | 1 | 0 | 1 | 849 | 1 | 283 | 0 | 531 |
| TBCP-1560_g_0799 | gi|489771780| ref|WP_003675686.1| | peptide-methionine (S)-S-oxide reductase [*Lactobacillus reuteri*] | 100 | 185 | 0 | 0 | 1 | 555 | 1 | 185 | 2.30E-140 | 387 |
| TBCP-1560_g_0802 | gi|512738998| ref|WP_016496719.1| | hypothetical protein [*Lactobacillus reuteri*] | 100 | 313 | 0 | 0 | 1 | 939 | 1 | 313 | 0 | 638 |
| TBCP-1560_g_0803 | gi|489771772| ref|WP_003675678.1| | hypothetical protein [*Lactobacillus reuteri*] | 100 | 168 | 0 | 0 | 1 | 504 | 1 | 168 | 1.26E-122 | 341 |
| TBCP-1560_g_0806 | gi|489771771| ref|WP_003675677.1| | TetR family transcriptional regulator [*Lactobacillus reuteri*] | 98.039 | 204 | 4 | 0 | 1 | 612 | 1 | 204 | 3.44E-148 | 409 |
| TBCP-1560_g_0808 | gi|489760062| ref|WP_003664009.1| | 50S ribosomal protein L21 [*Lactobacillus reuteri*] | 100 | 102 | 0 | 0 | 1 | 306 | 1 | 102 | 5.16E-57 | 170 |
| TBCP-1560_g_0810 | gi|489760059| ref|WP_003664006.1| | 50S ribosomal protein L27 [*Lactobacillus reuteri*] | 100 | 93 | 0 | 0 | 1 | 279 | 1 | 93 | 1.32E-64 | 189 |
| TBCP-1560_g_0816 | gi|489771761| ref|WP_003675667.1| | bifunctional 5,10-methylene-tetrahydrofolate dehydrogenase/5,10-methylene-tetrahydrofolate cyclohydrolase [*Lactobacillus reuteri*] | 99.65 | 286 | 1 | 0 | 1 | 858 | 1 | 286 | 0 | 520 |
| TBCP-1560_g_0819 | gi|489771755| ref|WP_003675661.1| | farnesyl-diphosphate synthase [*Lactobacillus reuteri*] | 100 | 290 | 0 | 0 | 1 | 870 | 1 | 290 | 0 | 556 |
| TBCP-1560_g_0820 | gi|489764469| ref|WP_003668402.1| | cell division protein FtsJ [*Lactobacillus reuteri*] | 100 | 273 | 0 | 0 | 1 | 819 | 1 | 273 | 0 | 554 |
| TBCP-1560_g_0821 | gi|489771753| ref|WP_003675659.1| | ArgR family transcriptional regulator [*Lactobacillus reuteri*] | 100 | 150 | 0 | 0 | 1 | 450 | 1 | 150 | 1.48E-111 | 312 |
| TBCP-1560_g_0822 | gi|489771751| ref|WP_003675657.1| | DNA repair protein RecN [*Lactobacillus reuteri*] | 99.821 | 559 | 1 | 0 | 1 | 1677 | 1 | 559 | 0 | 1071 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0826 | gi\|512739002\|ref\|WP_016496722.1\| | pantothenate metabolism flavoprotein [*Lactobacillus reuteri*] | 99.751 | 401 | 1 | 0 | 1 | 1203 | 1 | 401 | 0 | 786 |
| TBCP-1560_g_0829 | gi\|512739004\|ref\|WP_016496724.1\| | 16S rRNA (cytosine(967)-C(5))-methyltransferase [*Lactobacillus reuteri*] | 99.555 | 449 | 2 | 0 | 1 | 1347 | 1 | 449 | 0 | 886 |
| TBCP-1560_g_0830 | gi\|948620368\|gb\|KRK52332.1\| | protein phosphatase 2C-like protein [*Lactobacillus reuteri* DSM 20016] | 98.467 | 261 | 4 | 0 | 1 | 783 | 1 | 261 | 0 | 527 |
| TBCP-1560_g_0831 | gi\|1017201882\|ref\|WP_063164555.1\| | protein kinase [*Lactobacillus reuteri*] | 100 | 634 | 0 | 0 | 1 | 1902 | 1 | 634 | 0 | 1305 |
| TBCP-1560_g_0832 | gi\|489771738\|ref\|WP_003675644.1\| | ribosome small subunit-dependent GTPase A [*Lactobacillus reuteri*] | 99.662 | 296 | 1 | 0 | 1 | 888 | 1 | 296 | 0 | 613 |
| TBCP-1560_g_0833 | gi\|227071790\|gb\|EEI10079.1\| | ribulose-phosphate 3-epimerase [*Lactobacillus reuteri* MM2-3] | 100 | 217 | 0 | 0 | 1 | 651 | 15 | 231 | 7.04E-159 | 437 |
| TBCP-1560_g_0835 | gi\|948620363\|gb\|KRK52327.1\| | hypothetical protein FC53_GL000029 [*Lactobacillus reuteri* DSM 20016] | 100 | 61 | 0 | 0 | 1 | 183 | 22 | 82 | 8.69E-40 | 124 |
| TBCP-1560_g_0836 | gi\|2271185635\|gb\|EEI65706.1\| | hypothetical protein HMPREF0534_0958 [*Lactobacillus reuteri* CF48-3A] | 100 | 120 | 0 | 0 | 1 | 360 | 3 | 122 | 2.50E-82 | 236 |
| TBCP-1560_g_0839 | gi\|1017201886\|ref\|WP_063164559.1\| | phosphate acyltransferase [*Lactobacillus reuteri*] | 100 | 343 | 0 | 0 | 1 | 1029 | 1 | 343 | 0 | 694 |
| TBCP-1560_g_0844 | gi\|489759870\|ref\|WP_003663818.1\| | DNA-binding protein [*Lactobacillus reuteri*] | 100 | 113 | 0 | 0 | 1 | 339 | 1 | 113 | 1.34E-79 | 228 |
| TBCP-1560_g_0846 | gi\|489759868\|ref\|WP_003663816.1\| | 30S ribosomal protein S16 [*Lactobacillus reuteri*] | 98.901 | 91 | 1 | 0 | 1 | 273 | 1 | 91 | 3.03E-64 | 187 |
| TBCP-1560_g_0847 | gi\|489771725\|ref\|WP_003675631.1\| | RNA-binding protein [*Lactobacillus reuteri*] | 100 | 86 | 0 | 0 | 1 | 258 | 1 | 86 | 1.89E-58 | 172 |
| TBCP-1560_g_0848 | gi\|970363287\|emb\|CUR37646.1\| | 16S rRNA processing protein RimM [*Lactobacillus reuteri*] | 100 | 168 | 0 | 0 | 1 | 504 | 1 | 168 | 5.18E-110 | 309 |
| TBCP-1560_g_0851 | gi\|148531407\|gb\|ABQ83406.1\| | LSU ribosomal protein L19P [*Lactobacillus reuteri* DSM 20016] | 100 | 128 | 0 | 0 | 1 | 384 | 1 | 128 | 5.23E-90 | 256 |
| TBCP-1560_g_0853 | gi\|337728756\|emb\|CCC03875.1\| | hypothetical protein LRATCC53608_1122 [*Lactobacillus reuteri* ATCC 53608] | 100 | 110 | 0 | 0 | 1 | 330 | 2 | 111 | 1.99E-79 | 227 |
| TBCP-1560_g_0854 | gi\|489771712\|ref\|WP_003675618.1\| | exodeoxyribonuclease [*Lactobacillus reuteri*] | 99.636 | 275 | 1 | 0 | 1 | 825 | 1 | 275 | 0 | 573 |
| TBCP-1560_g_0857 | gi\|489771712\|ref\|WP_019253826.1\| | subtype II CRISPR-associated endonuclease Cas1 [*Lactobacillus reuteri*] | 97.682 | 302 | 7 | 0 | 1 | 906 | 1 | 302 | 0 | 610 |
| TBCP-1560_g_0858 | gi\|518083617\|ref\|WP_019253825.1\| | CRISPR-associated endonuclease Cas2 [*Lactobacillus reuteri*] | 100 | 101 | 0 | 0 | 1 | 303 | 1 | 101 | 1.28E-71 | 207 |
| TBCP-1560_g_0859 | gi\|518083616\|ref\|WP_019253824.1\| | type II-A CRISPR-associated protein Csn2 [*Lactobacillus reuteri*] | 98.206 | 223 | 4 | 0 | 1 | 669 | 1 | 223 | 2.39E-163 | 449 |
| TBCP-1560_g_0861 | gi\|489763052\|ref\|WP_003666989.1\| | PTS sugar transporter subunit IIA [*Lactobacillus reuteri*] | 99.507 | 203 | 1 | 0 | 1 | 609 | 1 | 203 | 4.87E-121 | 357 |
| TBCP-1560_g_0862 | gi\|737166902\|ref\|WP_035153222.1\| | phosphotransferase enzyme IIA component [*Lactobacillus reuteri*] | 96.078 | 408 | 16 | 0 | 1 | 1224 | 233 | 640 | 0 | 768 |
| TBCP-1560_g_0863 | gi\|970370498\|emb\|CUR40930.1\| | Beta-galactosidase [*Lactobacillus reuteri*] | 97.173 | 672 | 19 | 0 | 1 | 2016 | 1 | 672 | 0 | 1370 |
| TBCP-1560_g_0865 | gi\|512739014\|ref\|WP_016496734.1\| | 1,4-dihydroxy-2-naphthoate polyprenyltransferase [*Lactobacillus reuteri*] | 100 | 299 | 0 | 0 | 1 | 897 | 1 | 299 | 0 | 565 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0868 | gi\|489771699\|ref\|WP_003675605.1\| | metallophoesterase [*Lactobacillus reuteri*] | 100 | 279 | 0 | 0 | 40 | 876 | 14 | 292 | 0 | 583 |
| TBCP-1560_g_0869 | gi\|489763069\|ref\|WP_003667006.1\| | 30S ribosomal protein S14 [*Lactobacillus reuteri*] | 100 | 89 | 0 | 0 | 1 | 267 | 1 | 89 | 2.04E-61 | 180 |
| TBCP-1560_g_0871 | gi\|489761765\|ref\|WP_003665706.1\| | hypothetical protein [*Lactobacillus reuteri*] | 100 | 18 | 0 | 0 | 172 | 225 | 213 | 230 | 1.92E-06 | 42.4 |
| TBCP-1560_g_0872 | gi\|970364325\|emb\|CUR36723.1\| | L-serine dehydratase, beta subunit [*Lactobacillus reuteri*] | 99.091 | 220 | 2 | 0 | 1 | 660 | 1 | 220 | 1.03E-162 | 447 |
| TBCP-1560_g_0873 | gi\|489771691\|ref\|WP_003675597.1\| | L-serine dehydratase, iron-sulfur-dependent subunit alpha [*Lactobacillus reuteri*] | 100 | 293 | 0 | 0 | 1 | 879 | 1 | 293 | 1.60E-174 | 483 |
| TBCP-1560_g_0874 | gi\|489771689\|ref\|WP_003675595.1\| | peroxiredoxin [*Lactobacillus reuteri*] | 99.465 | 187 | 1 | 0 | 1 | 561 | 1 | 187 | 3.64E-140 | 387 |
| TBCP-1560_g_0876 | gi\|512155769\|gb\|AGN99052.1\| | LPXTG-motif cell wall anchor domain protein [*Lactobacillus reuteri* I5007] | 99.719 | 356 | 1 | 0 | 1 | 1068 | 1 | 356 | 0 | 632 |
| TBCP-1560_g_0881 | gi\|915327763\|ref\|WP_050764451.1\| | hypothetical protein [*Lactobacillus reuteri*] | 42.133 | 966 | 535 | 3 | 472 | 3363 | 139 | 1082 | 7.25E-151 | 502 |
| TBCP-1560_g_0881 | gi\|915327763\|ref\|WP_050764451.1\| | hypothetical protein [*Lactobacillus reuteri*] | 42.65 | 966 | 550 | 2 | 472 | 3363 | 539 | 1502 | 6.86E-150 | 499 |
| TBCP-1560_g_0881 | gi\|915327763\|ref\|WP_050764451.1\| | hypothetical protein [*Lactobacillus reuteri*] | 41.362 | 984 | 537 | 3 | 472 | 3363 | 49 | 1012 | 4.45E-149 | 496 |
| TBCP-1560_g_0881 | gi\|915327763\|ref\|WP_050764451.1\| | hypothetical protein [*Lactobacillus reuteri*] | 41.667 | 984 | 534 | 4 | 472 | 3363 | 69 | 1032 | 6.36E-149 | 496 |
| TBCP-1560_g_0881 | gi\|915327763\|ref\|WP_050764451.1\| | hypothetical protein [*Lactobacillus reuteri*] | 41.786 | 974 | 537 | 3 | 472 | 3363 | 509 | 1462 | 8.84E-149 | 496 |
| TBCP-1560_g_0881 | gi\|915327763\|ref\|WP_050764451.1\| | hypothetical protein [*Lactobacillus reuteri*] | 42.17 | 977 | 525 | 4 | 472 | 3342 | 1429 | 2385 | 1.24E-148 | 495 |
| TBCP-1560_g_0881 | gi\|915327763\|ref\|WP_050764451.1\| | hypothetical protein [*Lactobacillus reuteri*] | 42.402 | 974 | 527 | 5 | 472 | 3357 | 1159 | 2110 | 1.71E-148 | 495 |
| TBCP-1560_g_0881 | gi\|915327763\|ref\|WP_050764451.1\| | hypothetical protein [*Lactobacillus reuteri*] | 41.814 | 959 | 534 | 3 | 472 | 3342 | 419 | 1355 | 2.68E-148 | 494 |
| TBCP-1560_g_0881 | gi\|915327763\|ref\|WP_050764451.1\| | hypothetical protein [*Lactobacillus reuteri*] | 42.547 | 966 | 541 | 3 | 472 | 3363 | 1699 | 2652 | 4.67E-148 | 494 |
| TBCP-1560_g_0881 | gi\|915327763\|ref\|WP_050764451.1\| | hypothetical protein [*Lactobacillus reuteri*] | 41.159 | 984 | 539 | 3 | 472 | 3363 | 349 | 1312 | 6.86E-148 | 493 |
| TBCP-1560_g_0881 | gi\|915327763\|ref\|WP_050764451.1\| | hypothetical protein [*Lactobacillus reuteri*] | 41.615 | 966 | 540 | 3 | 472 | 3363 | 239 | 1182 | 2.26E-147 | 491 |
| TBCP-1560_g_0881 | gi\|915327763\|ref\|WP_050764451.1\| | hypothetical protein [*Lactobacillus reuteri*] | 41.684 | 974 | 538 | 3 | 472 | 3363 | 1369 | 2322 | 1.11E-146 | 489 |
| TBCP-1560_g_0881 | gi\|915327763\|ref\|WP_050764451.1\| | hypothetical protein [*Lactobacillus reuteri*] | 42.641 | 992 | 539 | 4 | 472 | 3357 | 1009 | 2000 | 1.63E-146 | 489 |
| TBCP-1560_g_0881 | gi\|915327763\|ref\|WP_050764451.1\| | hypothetical protein [*Lactobacillus reuteri*] | 41.786 | 974 | 543 | 3 | 472 | 3357 | 259 | 1220 | 1.70E-146 | 489 |
| TBCP-1560_g_0881 | gi\|915327763\|ref\|WP_050764451.1\| | hypothetical protein [*Lactobacillus reuteri*] | 42.284 | 972 | 541 | 3 | 472 | 3357 | 849 | 1810 | 1.84E-146 | 489 |
| TBCP-1560_g_0881 | gi\|915327763\|ref\|WP_050764451.1\| | hypothetical protein [*Lactobacillus reuteri*] | 41.018 | 1002 | 525 | 4 | 472 | 3363 | 1539 | 2512 | 2.50E-146 | 488 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0881 | gi\|153272763\|ref\|WP_050764451.1\| | hypothetical protein [*Lactobacillus reuteri*] | 41.519 | 1014 | 533 | 7 | 472 | 3363 | 1559 | 2562 | 2.75E-146 | 488 |
| TBCP-1560_g_0881 | gi\|153272763\|ref\|WP_050764451.1\| | hypothetical protein [*Lactobacillus reuteri*] | 42.427 | 964 | 541 | 3 | 472 | 3357 | 1269 | 2220 | 3.72E-146 | 488 |
| TBCP-1560_g_0881 | gi\|153272763\|ref\|WP_050764451.1\| | hypothetical protein [*Lactobacillus reuteri*] | 42.029 | 966 | 536 | 3 | 472 | 3363 | 829 | 1772 | 4.08E-146 | 488 |
| TBCP-1560_g_0881 | gi\|153272763\|ref\|WP_050764451.1\| | hypothetical protein [*Lactobacillus reuteri*] | 41.273 | 974 | 532 | 4 | 472 | 3363 | 2279 | 3222 | 4.44E-146 | 488 |
| TBCP-1560_g_0881 | gi\|153272763\|ref\|WP_050764451.1\| | hypothetical protein [*Lactobacillus reuteri*] | 41.718 | 966 | 539 | 3 | 472 | 3363 | 989 | 1932 | 7.66E-146 | 487 |
| TBCP-1560_g_0881 | gi\|153272763\|ref\|WP_050764451.1\| | hypothetical protein [*Lactobacillus reuteri*] | 42.186 | 979 | 542 | 2 | 472 | 3342 | 1819 | 2795 | 1.46E-145 | 486 |
| TBCP-1560_g_0881 | gi\|153272763\|ref\|WP_050764451.1\| | hypothetical protein [*Lactobacillus reuteri*] | 41.822 | 966 | 538 | 3 | 472 | 3363 | 719 | 1662 | 1.56E-145 | 486 |
| TBCP-1560_g_0881 | gi\|153272763\|ref\|WP_050764451.1\| | hypothetical protein [*Lactobacillus reuteri*] | 41.383 | 969 | 534 | 4 | 472 | 3342 | 679 | 1625 | 2.27E-145 | 485 |
| TBCP-1560_g_0881 | gi\|153272763\|ref\|WP_050764451.1\| | hypothetical protein [*Lactobacillus reuteri*] | 41.889 | 974 | 546 | 2 | 472 | 3363 | 2129 | 3092 | 3.28E-145 | 485 |
| TBCP-1560_g_0881 | gi\|153272763\|ref\|WP_050764451.1\| | hypothetical protein [*Lactobacillus reuteri*] | 41.833 | 1004 | 534 | 4 | 472 | 3363 | 1289 | 2282 | 3.50E-145 | 484 |
| TBCP-1560_g_0881 | gi\|153272763\|ref\|WP_050764451.1\| | hypothetical protein [*Lactobacillus reuteri*] | 41.273 | 974 | 538 | 3 | 472 | 3357 | 19 | 970 | 8.00E-145 | 484 |
| TBCP-1560_g_0881 | gi\|153272763\|ref\|WP_050764451.1\| | hypothetical protein [*Lactobacillus reuteri*] | 41.65 | 982 | 543 | 3 | 472 | 3357 | 1209 | 2180 | 9.04E-145 | 484 |
| TBCP-1560_g_0881 | gi\|153272763\|ref\|WP_050764451.1\| | hypothetical protein [*Lactobacillus reuteri*] | 41.925 | 966 | 537 | 3 | 472 | 3363 | 1189 | 2132 | 1.41E-144 | 483 |
| TBCP-1560_g_0881 | gi\|153272763\|ref\|WP_050764451.1\| | hypothetical protein [*Lactobacillus reuteri*] | 41.955 | 982 | 540 | 4 | 472 | 3357 | 1769 | 2740 | 1.78E-144 | 483 |
| TBCP-1560_g_0881 | gi\|153272763\|ref\|WP_050764451.1\| | hypothetical protein [*Lactobacillus reuteri*] | 41.159 | 984 | 549 | 3 | 472 | 3363 | 649 | 1622 | 3.52E-144 | 482 |
| TBCP-1560_g_0881 | gi\|153272763\|ref\|WP_050764451.1\| | hypothetical protein [*Lactobacillus reuteri*] | 40.744 | 994 | 539 | 4 | 472 | 3363 | 2079 | 3052 | 1.29E-143 | 481 |
| TBCP-1560_g_0881 | gi\|153272763\|ref\|WP_050764451.1\| | hypothetical protein [*Lactobacillus reuteri*] | 41.803 | 976 | 534 | 5 | 472 | 3363 | 1879 | 2832 | 1.72E-143 | 480 |
| TBCP-1560_g_0881 | gi\|153272763\|ref\|WP_050764451.1\| | hypothetical protein [*Lactobacillus reuteri*] | 40.895 | 961 | 534 | 3 | 511 | 3357 | 2 | 940 | 5.58E-142 | 476 |
| TBCP-1560_g_0881 | gi\|153272763\|ref\|WP_050764451.1\| | hypothetical protein [*Lactobacillus reuteri*] | 41.147 | 994 | 535 | 6 | 472 | 3363 | 2149 | 3122 | 7.97E-142 | 475 |
| TBCP-1560_g_0881 | gi\|153272763\|ref\|WP_050764451.1\| | hypothetical protein [*Lactobacillus reuteri*] | 40.335 | 1014 | 535 | 8 | 472 | 3363 | 2169 | 3162 | 2.26E-140 | 471 |
| TBCP-1560_g_0881 | gi\|153272763\|ref\|WP_050764451.1\| | hypothetical protein [*Lactobacillus reuteri*] | 42.105 | 969 | 547 | 4 | 472 | 3342 | 1969 | 2935 | 6.28E-140 | 469 |
| TBCP-1560_g_0881 | gi\|153272763\|ref\|WP_050764451.1\| | hypothetical protein [*Lactobacillus reuteri*] | 41.922 | 947 | 520 | 4 | 472 | 3252 | 2299 | 3235 | 1.19E-139 | 469 |
| TBCP-1560_g_0881 | gi\|153272763\|ref\|WP_050764451.1\| | hypothetical protein [*Lactobacillus reuteri*] | 41.287 | 901 | 489 | 2 | 781 | 3363 | 2 | 902 | 6.78E-136 | 457 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0881 | gi\|915327763\|ref\|WP_050764451.1\| | hypothetical protein [*Lactobacillus reuteri*] | 23.209 | 1103 | 749 | 9 | 203 | 3397 | 2026 | 3068 | 2.67E-66 | 246 |
| TBCP-1560_g_0881 | gi\|915327763\|ref\|WP_050764451.1\| | hypothetical protein [*Lactobacillus reuteri*] | 23.727 | 923 | 636 | 8 | 761 | 3397 | 1960 | 2858 | 6.35E-66 | 245 |
| TBCP-1560_g_0881 | gi\|915327763\|ref\|WP_050764451.1\| | hypothetical protein [*Lactobacillus reuteri*] | 23.911 | 941 | 652 | 14 | 761 | 3397 | 650 | 1588 | 1.25E-65 | 244 |
| TBCP-1560_g_0881 | gi\|915327763\|ref\|WP_050764451.1\| | hypothetical protein [*Lactobacillus reuteri*] | 23.877 | 913 | 647 | 10 | 761 | 3397 | 1090 | 1988 | 5.28E-65 | 242 |
| TBCP-1560_g_0881 | gi\|915327763\|ref\|WP_050764451.1\| | hypothetical protein [*Lactobacillus reuteri*] | 23.663 | 879 | 631 | 3 | 761 | 3397 | 1880 | 2718 | 9.74E-65 | 241 |
| TBCP-1560_g_0881 | gi\|915327763\|ref\|WP_050764451.1\| | hypothetical protein [*Lactobacillus reuteri*] | 23.793 | 891 | 635 | 7 | 761 | 3397 | 200 | 1058 | 3.06E-64 | 239 |
| TBCP-1560_g_0881 | gi\|915327763\|ref\|WP_050764451.1\| | hypothetical protein [*Lactobacillus reuteri*] | 42.126 | 508 | 284 | 1 | 472 | 1965 | 2729 | 3236 | 5.92E-64 | 239 |
| TBCP-1560_g_0881 | gi\|915327763\|ref\|WP_050764451.1\| | hypothetical protein [*Lactobacillus reuteri*] | 23.749 | 939 | 636 | 14 | 761 | 3397 | 770 | 1688 | 1.14E-63 | 238 |
| TBCP-1560_g_0881 | gi\|915327763\|ref\|WP_050764451.1\| | hypothetical protein [*Lactobacillus reuteri*] | 23.663 | 879 | 623 | 7 | 761 | 3355 | 2020 | 2864 | 1.42E-63 | 238 |
| TBCP-1560_g_0881 | gi\|915327763\|ref\|WP_050764451.1\| | hypothetical protein [*Lactobacillus reuteri*] | 23.119 | 1103 | 710 | 17 | 203 | 3397 | 1646 | 2648 | 1.96E-63 | 237 |
| TBCP-1560_g_0881 | gi\|915327763\|ref\|WP_050764451.1\| | hypothetical protein [*Lactobacillus reuteri*] | 23.619 | 923 | 647 | 11 | 761 | 3397 | 90 | 998 | 2.71E-63 | 236 |
| TBCP-1560_g_0881 | gi\|915327763\|ref\|WP_050764451.1\| | hypothetical protein [*Lactobacillus reuteri*] | 23.161 | 1101 | 742 | 15 | 203 | 3397 | 1196 | 2228 | 8.72E-63 | 235 |
| TBCP-1560_g_0881 | gi\|915327763\|ref\|WP_050764451.1\| | hypothetical protein [*Lactobacillus reuteri*] | 23.106 | 1069 | 732 | 10 | 203 | 3397 | 816 | 1798 | 1.54E-62 | 234 |
| TBCP-1560_g_0881 | gi\|915327763\|ref\|WP_050764451.1\| | hypothetical protein [*Lactobacillus reuteri*] | 23.818 | 1079 | 762 | 12 | 203 | 3397 | 1466 | 2498 | 4.48E-62 | 233 |
| TBCP-1560_g_0881 | gi\|915327763\|ref\|WP_050764451.1\| | hypothetical protein [*Lactobacillus reuteri*] | 23.432 | 909 | 666 | 5 | 761 | 3397 | 20 | 928 | 6.24E-62 | 232 |
| TBCP-1560_g_0881 | gi\|915327763\|ref\|WP_050764451.1\| | hypothetical protein [*Lactobacillus reuteri*] | 22.477 | 1090 | 757 | 9 | 212 | 3397 | 319 | 1348 | 3.68E-61 | 230 |
| TBCP-1560_g_0881 | gi\|915327763\|ref\|WP_050764451.1\| | hypothetical protein [*Lactobacillus reuteri*] | 22.341 | 1119 | 749 | 16 | 203 | 3397 | 456 | 1508 | 6.58E-61 | 229 |
| TBCP-1560_g_0881 | gi\|915327763\|ref\|WP_050764451.1\| | hypothetical protein [*Lactobacillus reuteri*] | 22.53 | 1012 | 686 | 11 | 494 | 3397 | 1371 | 2328 | 1.93E-60 | 228 |
| TBCP-1560_g_0881 | gi\|915327763\|ref\|WP_050764451.1\| | hypothetical protein [*Lactobacillus reuteri*] | 22.955 | 880 | 634 | 6 | 884 | 3397 | 1 | 878 | 3.91E-60 | 226 |
| TBCP-1560_g_0881 | gi\|915327763\|ref\|WP_050764451.1\| | hypothetical protein [*Lactobacillus reuteri*] | 23.616 | 885 | 606 | 9 | 761 | 3355 | 1010 | 1844 | 1.26E-59 | 225 |
| TBCP-1560_g_0881 | gi\|915327763\|ref\|WP_050764451.1\| | hypothetical protein [*Lactobacillus reuteri*] | 22.533 | 1074 | 710 | 11 | 266 | 3397 | 1157 | 2138 | 1.50E-59 | 224 |
| TBCP-1560_g_0881 | gi\|915327763\|ref\|WP_050764451.1\| | hypothetical protein [*Lactobacillus reuteri*] | 23.367 | 903 | 634 | 10 | 761 | 3397 | 1150 | 2018 | 3.96E-59 | 223 |
| TBCP-1560_g_0881 | gi\|915327763\|ref\|WP_050764451.1\| | hypothetical protein [*Lactobacillus reuteri*] | 21.875 | 1024 | 696 | 10 | 482 | 3397 | 647 | 1618 | 2.26E-58 | 221 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0881 | gi\|915327763\|ref\|WP_050764451.1\| | hypothetical protein [*Lactobacillus reuteri*] | 22.857 | 980 | 682 | 7 | 494 | 3397 | 201 | 1118 | 3.39E-58 | 220 |
| TBCP-1560_g_0881 | gi\|915327763\|ref\|WP_050764451.1\| | hypothetical protein [*Lactobacillus reuteri*] | 22.574 | 979 | 658 | 16 | 761 | 3397 | 270 | 1248 | 1.01E-57 | 219 |
| TBCP-1560_g_0881 | gi\|915327763\|ref\|WP_050764451.1\| | hypothetical protein [*Lactobacillus reuteri*] | 19.671 | 1154 | 813 | 32 | 3402 | 199 | 2057 | 3182 | 6.99E-52 | 200 |
| TBCP-1560_g_0881 | gi\|915327763\|ref\|WP_050764451.1\| | hypothetical protein [*Lactobacillus reuteri*] | 21.024 | 1113 | 807 | 25 | 3399 | 181 | 928 | 2008 | 1.24E-49 | 192 |
| TBCP-1560_g_0882 | gi\|917061910\|ref\|WP_051668622.1\| | hypothetical protein [*Lactobacillus reuteri*] | 60 | 30 | 12 | 0 | 19 | 108 | 9 | 38 | 1.04E-06 | 42.7 |
| TBCP-1560_g_0887 | gi\|489771675\|ref\|WP_003675581.1\| | accessory Sec system protein Asp3 [*Lactobacillus reuteri*] | 100 | 295 | 0 | 0 | 1 | 885 | 1 | 295 | 0 | 602 |
| TBCP-1560_g_0889 | gi\|489771671\|ref\|WP_003675577.1\| | accessory Sec system glycosyltransferase GtfA [*Lactobacillus reuteri*] | 100 | 512 | 0 | 0 | 1 | 1536 | 1 | 512 | 0 | 1058 |
| TBCP-1560_g_0891 | gi\|512739028\|ref\|WP_016496748.1\| | hypothetical protein [*Lactobacillus reuteri*] | 98.462 | 65 | 1 | 0 | 1 | 195 | 1 | 65 | 2.77E-17 | 67.4 |
| TBCP-1560_g_0892 | gi\|1017201897\|ref\|WP_063164570.1\| | adhesin [*Lactobacillus reuteri*] | 99.065 | 107 | 1 | 0 | 1 | 321 | 1 | 107 | 1.29E-58 | 180 |
| TBCP-1560_g_0893 | gi\|1017201898\|ref\|WP_063164571.1\| | cell wall protein [*Lactobacillus reuteri*] | 100 | 230 | 0 | 0 | 61 | 750 | 21 | 250 | 2.63E-141 | 420 |
| TBCP-1560_g_0893 | gi\|1017201898\|ref\|WP_063164571.1\| | cell wall protein [*Lactobacillus reuteri*] | 99.462 | 186 | 1 | 0 | 1174 | 1731 | 382 | 567 | 1.43E-21 | 97.8 |
| TBCP-1560_g_0894 | gi\|512155787\|ref\|WP_016496754.1\| | IstB ATP binding domain-containing protein [*Lactobacillus reuteri* IS007] | 99.519 | 208 | 1 | 0 | 1 | 624 | 1 | 208 | 2.11E-155 | 427 |
| TBCP-1560_g_0897 | gb\|AGN99070.1\| | potassium transporter [*Lactobacillus reuteri*] | 100 | 609 | 0 | 0 | 1 | 1827 | 1 | 609 | 0 | 1095 |
| TBCP-1560_g_0898 | gi\|489772852\|ref\|WP_003676754.1\| | 4-oxalocrotonate tautomerase [*Lactobacillus reuteri*] | 100 | 61 | 0 | 0 | 1 | 183 | 1 | 61 | 1.26E-39 | 123 |
| TBCP-1560_g_0899 | gi\|489795960\|ref\|WP_003663508.1\| | Glycerol kinase [*Lactobacillus reuteri*] | 98.8 | 500 | 6 | 0 | 1 | 1500 | 1 | 500 | 0 | 948 |
| TBCP-1560_g_0900 | gi\|970364616\|emb\|CUR43848.1\| | FIG00745619: hypothetical protein [*Lactobacillus reuteri*] | 100 | 167 | 0 | 0 | 1 | 501 | 1 | 167 | 5.64E-124 | 345 |
| TBCP-1560_g_0903 | gi\|489772841\|ref\|WP_003676743.1\| | exopolysaccharide biosynthesis protein [*Lactobacillus reuteri*] | 98.969 | 291 | 3 | 0 | 1 | 873 | 1 | 291 | 0 | 592 |
| TBCP-1560_g_0904 | gi\|489772839\|ref\|WP_003676741.1\| | exopolysaccharide biosynthesis protein [*Lactobacillus reuteri*] | 98.712 | 233 | 3 | 0 | 1 | 699 | 1 | 233 | 1.06E-169 | 467 |
| TBCP-1560_g_0905 | gi\|970369186\|emb\|CUR42563.1\| | Lipid carrier: UDP-N-acetylgalactosaminyltransferase [*Lactobacillus reuteri*] | 68.72 | 211 | 64 | 1 | 10 | 642 | 5 | 213 | 2.66E-108 | 309 |
| TBCP-1560_g_0906 | gi\|659902175\|gb\|KEK169447.1\| | glycosyl transferase [*Lactobacillus reuteri*] | 63.947 | 380 | 137 | 0 | 4 | 1143 | 9 | 388 | 5.68E-172 | 484 |
| TBCP-1560_g_0907 | gi\|526245771\|ref\|WP_020843125.1\| | hypothetical protein [*Lactobacillus reuteri*] | 25.714 | 420 | 266 | 13 | 10 | 1218 | 1 | 393 | 1.57E-36 | 137 |
| TBCP-1560_g_0909 | gi\|970369097\|emb\|CUR38065.1\| | capsular polysaccharide biosynthesis protein [*Lactobacillus reuteri*] | 30.952 | 294 | 190 | 8 | 136 | 999 | 57 | 343 | 2.99E-24 | 102 |
| TBCP-1560_g_0915 | gi\|489772294\|ref\|WP_003676198.1\| | ATPase AAA [*Lactobacillus reuteri*] | 100 | 245 | 0 | 0 | 1 | 735 | 1 | 245 | 0 | 506 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0918 | gi\|1017201766\|ref\|WP_063164439.1\| | dTDP-glucose 4,6-dehydratase [*Lactobacillus reuteri*] | 99.711 | 346 | 1 | 0 | 1 | 1038 | 1 | 346 | 0 | 671 |
| TBCP-1560_g_0924 | gi\|1017201899\|ref\|WP_063164572.1\| | integrase [*Lactobacillus reuteri*] | 97.778 | 315 | 7 | 0 | 10 | 954 | 66 | 380 | 0 | 644 |
| TBCP-1560_g_0925 | gi\|953265103\|emb\|CUU12464.1\| | Insertion sequence IS232 putative ATP-binding protein [*Lactobacillus reuteri* ATCC 53608] | 99.592 | 245 | 1 | 0 | 1 | 735 | 1 | 245 | 0 | 503 |
| TBCP-1560_g_0926 | gi\|1017201453\|ref\|WP_063164126.1\| | hypothetical protein [*Lactobacillus reuteri*] | 31.311 | 412 | 192 | 16 | 31 | 1137 | 5 | 368 | 3.68E-39 | 144 |
| TBCP-1560_g_0927 | gi\|518082660\|ref\|WP_019252868.1\| | hypothetical protein [*Lactobacillus reuteri*] | 34.286 | 105 | 63 | 3 | 640 | 942 | 184 | 286 | 8.05E-07 | 51.2 |
| TBCP-1560_g_0932 | gi\|970367365\|emb\|CUR39614.1\| | hypothetical protein LRLP16767_LR3C6_01581 [*Lactobacillus reuteri*] | 90.244 | 82 | 8 | 0 | 1 | 246 | 1 | 82 | 6.22E-49 | 155 |
| TBCP-1560_g_0934 | gi\|489768400\|ref\|WP_003672322.1\| | homocysteine S-methyltransferase [*Lactobacillus reuteri*] | 97.742 | 310 | 7 | 0 | 1 | 930 | 1 | 310 | 0 | 594 |
| TBCP-1560_g_0936 | gi\|489763124\|ref\|WP_003667061.1\| | hypothetical protein [*Lactobacillus reuteri*] | 98.824 | 85 | 1 | 0 | 1 | 255 | 1 | 85 | 4.19E-55 | 164 |
| TBCP-1560_g_0939 | gi\|970363280\|emb\|CUR37717.1\| | PemK family protein [*Lactobacillus reuteri*] | 98.78 | 82 | 1 | 0 | 1 | 246 | 1 | 82 | 4.87E-57 | 169 |
| TBCP-1560_g_0940 | gi\|970363279\|emb\|CUR37716.1\| | FIG00751385: hypothetical protein [*Lactobacillus reuteri*] | 98.75 | 80 | 1 | 0 | 1 | 240 | 1 | 80 | 6.00E-54 | 160 |
| TBCP-1560_g_0941 | gi\|489772795\|ref\|WP_003676697.1\| | hypothetical protein [*Lactobacillus reuteri*] | 98.374 | 615 | 10 | 0 | 1 | 1845 | 1 | 615 | 0 | 1117 |
| TBCP-1560_g_0942 | gi\|1017201365\|ref\|WP_063164038.1\| | DEAD/DEAH box helicase [*Lactobacillus reuteri*] | 99.914 | 1161 | 1 | 0 | 1 | 3483 | 1 | 1161 | 0 | 2331 |
| TBCP-1560_g_0945 | gi\|518081247\|ref\|WP_019251455.1\| | exonuclease sbcCD subunit D [*Lactobacillus reuteri*] | 98.925 | 372 | 4 | 0 | 1 | 1116 | 1 | 372 | 0 | 763 |
| TBCP-1560_g_0952 | gi\|489768426\|ref\|WP_003672348.1\| | phosphoglycerate kinase [*Lactobacillus reuteri*] | 98.561 | 278 | 4 | 0 | 1 | 834 | 1 | 278 | 0 | 544 |
| TBCP-1560_g_0955 | gi\|657710404\|ref\|WP_029507401.1\| | hypothetical protein [*Lactobacillus reuteri*] | 96.875 | 192 | 6 | 0 | 1 | 576 | 144 | 335 | 9.14E-134 | 377 |
| TBCP-1560_g_0966 | gi\|518083012\|ref\|WP_019253220.1\| | hypothetical protein [*Lactobacillus reuteri*] | 99.01 | 101 | 1 | 0 | 1 | 303 | 1 | 101 | 3.20E-69 | 201 |
| TBCP-1560_g_0967 | gi\|489770069\|ref\|WP_003673982.1\| | hypothetical protein [*Lactobacillus reuteri*] | 97.946 | 633 | 13 | 0 | 1 | 1899 | 1 | 633 | 0 | 1228 |
| TBCP-1560_g_0973 | gi\|754210193\|ref\|WP_041821667.1\| | peptide ABC transporter substrate-binding protein [*Lactobacillus reuteri*] | 100 | 317 | 0 | 0 | 1 | 951 | 15 | 331 | 0 | 544 |
| TBCP-1560_g_0978 | gi\|970362331\|emb\|CUR37781.1\| | FIG00742465: hypothetical protein [*Lactobacillus reuteri*] | 99.655 | 290 | 1 | 0 | 1 | 870 | 1 | 290 | 0 | 593 |
| TBCP-1560_g_0981 | gi\|489770084\|ref\|WP_003673997.1\| | DNA-binding response regulator [*Lactobacillus reuteri*] | 100 | 217 | 0 | 0 | 1 | 651 | 1 | 217 | 7.49E-160 | 439 |
| TBCP-1560_g_0983 | gi\|489763785\|ref\|WP_003667721.1\| | hypothetical protein [*Lactobacillus reuteri*] | 98.936 | 94 | 1 | 0 | 1 | 282 | 1 | 94 | 4.09E-51 | 154 |
| TBCP-1560_g_0984 | gi\|512739103\|ref\|WP_016496821.1\| | molybdopterin-guanine dinucleotide biosynthesis protein MobA [*Lactobacillus reuteri*] | 98.947 | 190 | 2 | 0 | 1 | 570 | 1 | 190 | 4.66E-143 | 395 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_0985 | gi\|489770088\|ref\|WP_003674001.1\| | molybdopterin-guanine dinucleotide biosynthesis protein B [*Lactobacillus reuteri*] | 99.383 | 162 | 1 | 0 | 1 | 486 | 1 | 162 | 1.55E-120 | 335 |
| TBCP-1560_g_0986 | gi\|512739104\|ref\|WP_016496822.1\| | molybdopterin molybdenumtransferase MoeA [*Lactobacillus reuteri*] | 100 | 405 | 0 | 0 | 1 | 1215 | 1 | 405 | 0 | 839 |
| TBCP-1560_g_0987 | gi\|512739105\|ref\|WP_016496823.1\| | molybdenum cofactor biosynthesis protein [*Lactobacillus reuteri*] | 100 | 165 | 0 | 0 | 1 | 495 | 1 | 165 | 1.98E-109 | 308 |
| TBCP-1560_g_0988 | gi\|512739106\|ref\|WP_016496824.1\| | molybdopterin biosynthesis protein MoeB [*Lactobacillus reuteri*] | 99.41 | 339 | 1 | 1 | 1 | 1014 | 1 | 339 | 0 | 697 |
| TBCP-1560_g_0989 | gi\|489770095\|ref\|WP_003674008.1\| | nitrate reductase subunit alpha [*Lactobacillus reuteri*] | 99.918 | 1221 | 1 | 0 | 1 | 3663 | 1 | 1221 | 0 | 2561 |
| TBCP-1560_g_0990 | gi\|489770097\|ref\|WP_003674010.1\| | nitrate reductase subunit beta [*Lactobacillus reuteri*] | 99.615 | 519 | 2 | 0 | 1 | 1557 | 1 | 519 | 0 | 1087 |
| TBCP-1560_g_0991 | gi\|489759699\|ref\|WP_003663647.1\| | nitrate reductase molybdenum cofactor assembly chaperone [*Lactobacillus reuteri*] | 99.479 | 192 | 1 | 0 | 1 | 576 | 1 | 192 | 6.83E-138 | 382 |
| TBCP-1560_g_0992 | gi\|489763803\|ref\|WP_003667738.1\| | nitrate reductase subunit gamma [*Lactobacillus reuteri*] | 100 | 213 | 0 | 0 | 1 | 639 | 1 | 213 | 2.57E-157 | 434 |
| TBCP-1560_g_0998 | gi\|948614637\|gb\|KRK46737.1\| | hypothetical protein FC53_GL001335 [*Lactobacillus reuteri* DSM 20016] | 98.246 | 57 | 1 | 0 | 1 | 171 | 1 | 57 | 1.67E-38 | 120 |
| TBCP-1560_g_1000 | gi\|489763814\|ref\|WP_003667749.1\| | beta-hydroxyacyl-ACP dehydratase [*Lactobacillus reuteri*] | 100 | 145 | 0 | 0 | 1 | 435 | 4 | 148 | 2.35E-106 | 298 |
| TBCP-1560_g_1002 | gi\|489770110\|ref\|WP_003674023.1\| | 3-oxoacyl-ACP synthase III [*Lactobacillus reuteri*] | 99.383 | 324 | 2 | 0 | 1 | 972 | 1 | 324 | 0 | 660 |
| TBCP-1560_g_1003 | gi\|148531252\|gb\|ABQ83251.1\| | phosphopantetheine-binding protein [*Lactobacillus reuteri* DSM 20016] | 100 | 82 | 0 | 0 | 1 | 246 | 1 | 82 | 2.24E-50 | 152 |
| TBCP-1560_g_1004 | gi\|489770114\|ref\|WP_003674027.1\| | ACP S-malonyltransferase [*Lactobacillus reuteri*] | 100 | 316 | 0 | 0 | 1 | 948 | 1 | 316 | 0 | 656 |
| TBCP-1560_g_1005 | gi\|489770116\|ref\|WP_003674029.1\| | beta-ketoacyl-ACP reductase [*Lactobacillus reuteri*] | 100 | 244 | 0 | 0 | 1 | 732 | 1 | 244 | 0 | 497 |
| TBCP-1560_g_1010 | gi\|489770124\|ref\|WP_003674037.1\| | acetyl-CoA carboxylase subunit beta [*Lactobacillus reuteri*] | 100 | 289 | 0 | 0 | 1 | 867 | 1 | 289 | 0 | 605 |
| TBCP-1560_g_1011 | gi\|489770126\|ref\|WP_003674039.1\| | acetyl-CoA carboxylase carboxyl transferase subunit alpha [*Lactobacillus reuteri*] | 100 | 258 | 0 | 0 | 1 | 774 | 1 | 258 | 6.73E-171 | 471 |
| TBCP-1560_g_1017 | gi\|868713964\|gb\|AKP01217.1\| | putative alpha/beta hydrolase [*Lactobacillus reuteri*] | 98.089 | 157 | 3 | 0 | 1 | 471 | 129 | 285 | 2.30E-111 | 317 |
| TBCP-1560_g_1020 | gi\|489770141\|ref\|WP_003674054.1\| | hypothetical protein [*Lactobacillus reuteri*] | 100 | 93 | 0 | 0 | 82 | 360 | 28 | 120 | 2.43E-45 | 142 |
| TBCP-1560_g_1033 | gi\|489763578\|ref\|WP_003667514.1\| | two-component system response regulator [*Lactobacillus reuteri*] | 48.921 | 278 | 141 | 1 | 1 | 831 | 1 | 278 | 5.90E-99 | 290 |
| TBCP-1560_g_1034 | gi\|659902062\|gb\|KEK16839.1\| | amino acid permease [*Lactobacillus reuteri*] | 27.489 | 462 | 324 | 3 | 79 | 1464 | 23 | 473 | 1.64E-46 | 167 |
| TBCP-1560_g_1035 | gi\|148531853\|gb\|ABQ83852.1\| | Transposase and inactivated derivatives IS30 family-like protein [*Lactobacillus reuteri* DSM 20016] | 98.75 | 160 | 2 | 0 | 1 | 480 | 1 | 160 | 4.94E-117 | 327 |
| TBCP-1560_g_1038 | gi\|970364069\|emb\|CUR37081.1\| | Phage protein [*Lactobacillus reuteri*] | 99.76 | 417 | 1 | 0 | 1 | 1251 | 1 | 417 | 0 | 833 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1042 | gi\|970364066\|emb\|CUR37078.1\| | hypothetical protein LRLP16767_LRPG3B_00870 [*Lactobacillus reuteri*] | 95.652 | 46 | 2 | 0 | 34 | 171 | 1 | 46 | 1.07E-26 | 90.1 |
| TBCP-1560_g_1043 | gi\|970364065\|emb\|CUR37077.1\| | hypothetical protein LRLP16767_LRPG3B_00869 [*Lactobacillus reuteri*] | 98.857 | 175 | 2 | 0 | 1 | 525 | 1 | 175 | 7.26E-113 | 317 |
| TBCP-1560_g_1044 | gi\|970364064\|emb\|CUR37076.1\| | hypothetical protein LRLP16767_LRPG3B_00868 [*Lactobacillus reuteri*] | 100 | 114 | 0 | 0 | 1 | 342 | 1 | 114 | 7.66E-83 | 236 |
| TBCP-1560_g_1045 | gi\|970364063\|emb\|CUR37075.1\| | Integrase [*Lactobacillus reuteri*] | 99.728 | 367 | 1 | 0 | 1 | 1101 | 1 | 367 | 0 | 721 |
| TBCP-1560_g_1055 | gi\|489759851\|ref\|WP_003663799.1\| | glyoxalase [*Lactobacillus reuteri*] | 100 | 130 | 0 | 0 | 1 | 390 | 1 | 130 | 3.04E-95 | 269 |
| TBCP-1560_g_1064 | gi\|489770177\|ref\|WP_003674090.1\| | LysR family transcriptional regulator [*Lactobacillus reuteri*] | 100 | 294 | 0 | 0 | 1 | 882 | 1 | 294 | 0 | 602 |
| TBCP-1560_g_1066 | gi\|489770178\|ref\|WP_003674091.1\| | MFS transporter [*Lactobacillus reuteri*] | 100 | 296 | 0 | 0 | 1 | 888 | 1 | 296 | 0 | 611 |
| TBCP-1560_g_1067 | gi\|489762281\|ref\|WP_003666221.1\| | hypothetical protein [*Lactobacillus reuteri*] | 100 | 34 | 0 | 0 | 1 | 102 | 1 | 34 | 1.28E-16 | 64.7 |
| TBCP-1560_g_1076 | gi\|489770192\|ref\|WP_003674105.1\| | hypothetical protein [*Lactobacillus reuteri*] | 100 | 560 | 0 | 0 | 1 | 1680 | 1 | 560 | 0 | 1070 |
| TBCP-1560_g_1082 | gi\|489770201\|ref\|WP_003674114.1\| | ribonuclease HI [*Lactobacillus reuteri*] | 100 | 131 | 0 | 0 | 1 | 393 | 1 | 131 | 1.34E-81 | 234 |
| TBCP-1560_g_1088 | gi\|489770207\|ref\|WP_003674120.1\| | penicillin-binding protein 1A [*Lactobacillus reuteri*] | 100 | 676 | 0 | 0 | 1 | 2028 | 1 | 676 | 0 | 1342 |
| TBCP-1560_g_1093 | gi\|489770214\|ref\|WP_003674127.1\| | mevalonate kinase [*Lactobacillus reuteri*] | 100 | 316 | 0 | 0 | 1 | 948 | 1 | 316 | 0 | 590 |
| TBCP-1560_g_1094 | gi\|489770215\|ref\|WP_003674128.1\| | diphosphomevalonate decarboxylase [*Lactobacillus reuteri*] | 100 | 323 | 0 | 0 | 1 | 969 | 1 | 323 | 0 | 535 |
| TBCP-1560_g_1095 | gi\|489762243\|ref\|WP_003666183.1\| | phosphomevalonate kinase [*Lactobacillus reuteri*] | 99.733 | 375 | 1 | 0 | 1 | 1125 | 1 | 375 | 0 | 728 |
| TBCP-1560_g_1096 | gi\|489770216\|ref\|WP_003674129.1\| | type 2 isopentenyl-diphosphate Delta-isomerase [*Lactobacillus reuteri*] | 100 | 348 | 0 | 0 | 1 | 1044 | 1 | 348 | 0 | 686 |
| TBCP-1560_g_1099 | gi\|489770219\|ref\|WP_003674132.1\| | LacI family transcriptional regulator [*Lactobacillus reuteri*] | 100 | 339 | 0 | 0 | 1 | 1017 | 1 | 339 | 0 | 698 |
| TBCP-1560_g_1100 | gi\|489770220\|ref\|WP_003674133.1\| | fructokinase [*Lactobacillus reuteri*] | 99.658 | 292 | 1 | 0 | 1 | 876 | 1 | 292 | 0 | 579 |
| TBCP-1560_g_1108 | gi\|194452845\|gb\|EDX41743.1\| | Cof-like hydrolase [*Lactobacillus reuteri* 100-23] | 100 | 272 | 0 | 0 | 1 | 816 | 1 | 272 | 0 | 560 |
| TBCP-1560_g_1120 | gi\|489770238\|ref\|WP_003674151.1\| | iron transporter FeoA [*Lactobacillus reuteri*] | 100 | 67 | 0 | 0 | 1 | 201 | 1 | 67 | 1.31E-47 | 144 |
| TBCP-1560_g_1121 | gi\|489770239\|ref\|WP_003674152.1\| | ferrous iron transport protein B [*Lactobacillus reuteri*] | 100 | 663 | 0 | 0 | 1 | 1989 | 1 | 663 | 0 | 1322 |
| TBCP-1560_g_1125 | gi\|489770243\|ref\|WP_003674156.1\| | thioesterase [*Lactobacillus reuteri*] | 100 | 124 | 0 | 0 | 1 | 372 | 1 | 124 | 1.99E-89 | 254 |
| TBCP-1560_g_1128 | gi\|970365298\|emb\|CUR43832.1\| | FIG00744546: hypothetical protein [*Lactobacillus reuteri*] | 100 | 962 | 0 | 0 | 1 | 2886 | 1 | 962 | 0 | 1945 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1129 | gi\|970365299\| emb\|CUR43833.1\| | Potassium voltage-gated channel subfamily KQT; possible potassium channel, VIC family [*Lactobacillus reuteri*] | 99.17 | 241 | 2 | 0 | 1 | 723 | 1 | 241 | 4.53E-154 | 427 |
| TBCP-1560_g_1139 | gi\|659901251\| gb\|KEK16045.1\| | XRE family transcriptional regulator [*Lactobacillus reuteri*] | 91.139 | 79 | 7 | 0 | 1 | 237 | 1 | 79 | 1.42E-47 | 144 |
| TBCP-1560_g_1145 | gi\|970371392\| emb\|CUR40084.1\| | hypothetical protein LRLP16767_LR202_00134 [*Lactobacillus reuteri*] | 100 | 197 | 0 | 0 | 1 | 591 | 1 | 197 | 1.83E-140 | 404 |
| TBCP-1560_g_1147 | gi\|489764038\| ref\|WP_003667972.1\| | hypothetical protein [*Lactobacillus reuteri*] | 99.387 | 163 | 1 | 0 | 1 | 489 | 1 | 163 | 3.94E-93 | 266 |
| TBCP-1560_g_1150 | gi\|489770273\| ref\|WP_003674186.1\| | hypothetical protein [*Lactobacillus reuteri*] | 100 | 103 | 0 | 0 | 1 | 309 | 1 | 103 | 1.38E-46 | 144 |
| TBCP-1560_g_1153 | gi\|970365843\| emb\|CUR43297.1\| | Gluconate permease, Bsu4004 homolog [*Lactobacillus reuteri*] | 98.913 | 276 | 3 | 0 | 55 | 882 | 19 | 294 | 0 | 544 |
| TBCP-1560_g_1154 | gi\|337727830\| emb\|CCC02917.1\| | gluconate transport protein [*Lactobacillus reuteri* ATCC 53608] | 100 | 139 | 0 | 0 | 1 | 417 | 239 | 377 | 8.32E-71 | 216 |
| TBCP-1560_g_1155 | gi\|915462619\| ref\|WP_050802152.1\| | transcriptional regulator [*Lactobacillus reuteri*] | 100 | 334 | 0 | 0 | 1 | 1002 | 6 | 339 | 0 | 688 |
| TBCP-1560_g_1159 | gi\|489762152\| ref\|WP_003666092.1\| | hypothetical protein [*Lactobacillus reuteri*] | 100 | 63 | 0 | 0 | 1 | 189 | 1 | 63 | 8.23E-27 | 91.3 |
| TBCP-1560_g_1170 | gi\|489762134\| ref\|WP_003666074.1\| | glycerol-3-phosphate acyltransferase [*Lactobacillus reuteri*] | 100 | 209 | 0 | 0 | 1 | 627 | 1 | 209 | 5.19E-149 | 411 |
| TBCP-1560_g_1180 | gi\|489762122\| ref\|WP_003666062.1\| | hemolysin III [*Lactobacillus reuteri*] | 100 | 214 | 0 | 0 | 1 | 642 | 1 | 214 | 5.90E-120 | 338 |
| TBCP-1560_g_1203 | gi\|754210243\| ref\|WP_041821711.1\| | integral membrane protein [*Lactobacillus reuteri*] | 100 | 81 | 0 | 0 | 1 | 243 | 1 | 81 | 9.49E-56 | 165 |
| TBCP-1560_g_1240 | gi\|337727907\| emb\|CCC02996.1\| | conserved hypothetical protein [*Lactobacillus reuteri* ATCC 53608] | 100 | 58 | 0 | 0 | 1 | 174 | 1 | 58 | 4.42E-37 | 116 |
| TBCP-1560_g_1270 | gi\|227070166\| gb\|EEI08541.1\| | Acyltransferase [*Lactobacillus reuteri* MM2-3] | 99.588 | 243 | 1 | 0 | 1 | 729 | 1 | 243 | 3.64E-179 | 490 |
| TBCP-1560_g_1273 | gi\|489770423\| ref\|WP_003674334.1\| | repressor LexA [*Lactobacillus reuteri*] | 100 | 208 | 0 | 0 | 1 | 624 | 1 | 208 | 4.21E-156 | 429 |
| TBCP-1560_g_1277 | gi\|489770427\| ref\|WP_003674338.1\| | adenine phosphoribosyltransferase [*Lactobacillus reuteri*] | 100 | 172 | 0 | 0 | 1 | 516 | 1 | 172 | 8.74E-123 | 342 |
| TBCP-1560_g_1293 | gi\|489762895\| ref\|WP_003666832.1\| | 30S ribosomal protein S20 [*Lactobacillus reuteri*] | 100 | 84 | 0 | 0 | 1 | 252 | 1 | 84 | 2.02E-54 | 162 |
| TBCP-1560_g_1310 | gi\|489770468\| ref\|WP_003674379.1\| | peptide deformylase [*Lactobacillus reuteri*] | 100 | 186 | 0 | 0 | 1 | 558 | 1 | 186 | 7.87E-139 | 384 |
| TBCP-1560_g_1312 | gi\|489762866\| ref\|WP_003666803.1\| | hypothetical protein [*Lactobacillus reuteri*] | 100 | 70 | 0 | 0 | 1 | 210 | 1 | 70 | 1.57E-47 | 144 |
| TBCP-1560_g_1313 | gi\|489770470\| ref\|WP_003674381.1\| | diacylglycerol kinase [*Lactobacillus reuteri*] | 100 | 315 | 0 | 0 | 1 | 945 | 1 | 315 | 0 | 654 |
| TBCP-1560_g_1320 | gi\|512739239\| ref\|WP_016496953.1\| | sugar diacid utilization regulator [*Lactobacillus reuteri*] | 99.716 | 352 | 1 | 0 | 1 | 1056 | 1 | 352 | 0 | 673 |
| TBCP-1560_g_1328 | gi\|489770493\| ref\|WP_003674404.1\| | aspartate kinase [*Lactobacillus reuteri*] | 100 | 452 | 0 | 0 | 1 | 1356 | 1 | 452 | 0 | 925 |

TABLE 1-continued

Differential genes between strain CCFM8631 of *Lactobacillus reuteri* and standard strain DSM20016 of *Lactobacillus reuteri*

| Gene ID | mr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1381 | gi|489762939| ref|WP_003666876.1| | hypothetical protein [*Lactobacillus reuteri*] | 100 | 163 | 0 | 0 | 1 | 489 | 1 | 163 | 2.48E-120 | 335 |
| TBCP-1560_g_1407 | gi|489772128| ref|WP_003676032.1| | mechanosensitive ion channel protein [*Lactobacillus reuteri*] | 100 | 291 | 0 | 0 | 1 | 873 | 1 | 291 | 0 | 544 |
| TBCP-1560_g_1455 | gi|489762694| ref|WP_003666632.1| | 30S ribosomal protein S4 [*Lactobacillus reuteri*] | 100 | 201 | 0 | 0 | 1 | 603 | 1 | 201 | 2.21E-149 | 412 |
| TBCP-1560_g_1462 | gi|489762674| ref|WP_003666612.1| | hypothetical protein [*Lactobacillus reuteri*] | 100 | 247 | 0 | 0 | 1 | 741 | 1 | 247 | 0 | 502 |
| TBCP-1560_g_1466 | gi|489772205| ref|WP_003676109.1| | recombinase RarA [*Lactobacillus reuteri*] | 100 | 434 | 0 | 0 | 1 | 1302 | 1 | 434 | 0 | 861 |
| TBCP-1560_g_1467 | gi|489762666| ref|WP_003666604.1| | hypothetical protein [*Lactobacillus reuteri*] | 100 | 86 | 0 | 0 | 37 | 294 | 13 | 98 | 2.71E-59 | 176 |
| TBCP-1560_g_1469 | gi|489772208| ref|WP_003676112.1| | GntR family transcriptional regulator [*Lactobacillus reuteri*] | 99.178 | 365 | 3 | 0 | 1 | 1095 | 1 | 365 | 0 | 750 |
| TBCP-1560_g_1512 | gi|489772257| ref|WP_003676161.1| | glutamine amidotransferase [*Lactobacillus reuteri*] | 100 | 235 | 0 | 0 | 1 | 705 | 1 | 235 | 6.12E-174 | 476 |
| TBCP-1560_g_1513 | gi|489763609| | hypothetical protein [*Lactobacillus reuteri*] | 99 | 100 | 1 | 0 | 1 | 300 | 1 | 100 | 1.60E-49 | 151 |
| TBCP-1560_g_1519 | gi|489762592| ref|WP_003667545.1| | hypothetical protein [*Lactobacillus reuteri*] | 87.94 | 199 | 24 | 0 | 1 | 597 | 1 | 199 | 7.48E-53 | 167 |
| TBCP-1560_g_1522 | gi|970363739| emb|CUR37248.1| | Protein of unknown function DUF1085 [*Lactobacillus reuteri*] | 100 | 198 | 0 | 0 | 1 | 594 | 1 | 198 | 1.54E-149 | 412 |
| TBCP-1560_g_1527 | gi|489767250| ref|WP_003671176.1| | hypothetical protein [*Lactobacillus reuteri*] | 83.607 | 61 | 10 | 0 | 1 | 183 | 1 | 61 | 7.36E-23 | 81.3 |
| TBCP-1560_g_1528 | gi|1017201547| ref|WP_063164220.1| | hypothetical protein [*Lactobacillus reuteri*] | 66.816 | 223 | 56 | 1 | 1 | 669 | 1 | 205 | 1.54E-99 | 286 |
| TBCP-1560_g_1529 | gi|970369384| emb|CUR42281.1| | hypothetical protein LRLP16767_LR202_02008 [*Lactobacillus reuteri*] | 97.802 | 91 | 2 | 0 | 1 | 273 | 1 | 91 | 7.44E-65 | 189 |
| TBCP-1560_g_1530 | gi|1017201549| ref|WP_063164222.1| | hypothetical protein [*Lactobacillus reuteri*] | 94.382 | 89 | 5 | 0 | 46 | 312 | 16 | 104 | 1.26E-59 | 177 |
| TBCP-1560_g_1531 | gi|1017201497| ref|WP_063164170.1| | hypothetical protein [*Lactobacillus reuteri*] | 98.551 | 69 | 1 | 0 | 1 | 207 | 1 | 69 | 2.53E-45 | 138 |
| TBCP-1560_g_1535 | gb|KRK45104.1| | hypothetical protein FC53_GL001662 [*Lactobacillus reuteri* DSM 20016] | 98.496 | 133 | 2 | 0 | 1 | 399 | 14 | 146 | 2.76E-97 | 275 |
| TBCP-1560_g_1537 | gi|1017201557| ref|WP_063164230.1| | hypothetical protein [*Lactobacillus reuteri*] | 84.746 | 59 | 9 | 0 | 1 | 177 | 1 | 59 | 6.44E-32 | 103 |
| TBCP-1560_g_1539 | gi|512156405| gb|AGN99688.1| | Na+/H+ antiporter [*Lactobacillus reuteri* I5007] | 99.359 | 156 | 1 | 0 | 1 | 468 | 1 | 156 | 1.40E-103 | 292 |
| TBCP-1560_g_1551 | gi|970364845| emb|CUR36302.1| | Xylose-responsive transcription regulator, ROK family [*Lactobacillus reuteri*] | 100 | 242 | 0 | 0 | 13 | 738 | 67 | 308 | 1.50E-179 | 494 |
| TBCP-1560_g_1574 | gi|489772332| ref|WP_003676235.1| | hypothetical protein [*Lactobacillus reuteri*] | 100 | 140 | 0 | 0 | 1 | 420 | 1 | 140 | 8.00E-104 | 291 |
| TBCP-1560_g_1579 | gi|489763547| ref|WP_003667483.1| | hypothetical protein [*Lactobacillus reuteri*] | 99.485 | 194 | 1 | 0 | 1 | 582 | 1 | 194 | 1.62E-143 | 396 |
| TBCP-1560_g_1589 | gi|489762497| ref|WP_003666436.1| | type I glyceraldehyde-3-phosphate dehydrogenase [*Lactobacillus reuteri*] | 100 | 335 | 0 | 0 | 1 | 1005 | 1 | 335 | 0 | 688 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1590 | gi\|737183747\|ref\|WP_035169635.1\| | hypothetical protein [*Lactobacillus reuteri*] | 100 | 39 | 0 | 0 | 7 | 123 | 24 | 62 | 1.06E-22 | 79.7 |
| TBCP-1560_g_1592 | gi\|512739358\|ref\|WP_016497054.1\| | MFS transporter [*Lactobacillus reuteri*] | 100 | 451 | 0 | 0 | 1 | 1353 | 1 | 451 | 0 | 813 |
| TBCP-1560_g_1594 | gi\|183224377\|dbj\|BAG24894.1\| | hypothetical protein [*Lactobacillus reuteri* JCM 1112] | 100 | 43 | 0 | 0 | 1 | 129 | 1 | 43 | 2.07E-24 | 84 |
| TBCP-1560_g_1595 | gi\|227071512\|gb\|EEI09811.1\| | hypothetical protein HMPREF0535_0374 [*Lactobacillus reuteri* MM2-3] | 96.429 | 56 | 2 | 0 | 1 | 168 | 1 | 56 | 1.21E-33 | 107 |
| TBCP-1560_g_1611 | gi\|953265697\|emb\|CUU13083.1\| | Lactate utilization protein A [*Lactobacillus reuteri* ATCC 53608] | 100 | 298 | 0 | 0 | 1 | 894 | 1 | 298 | 0 | 595 |
| TBCP-1560_g_1626 | gi\|512739368\|ref\|WP_016497064.1\| | YigZ family protein [*Lactobacillus reuteri*] | 100 | 210 | 0 | 0 | 1 | 630 | 1 | 210 | 5.01E-157 | 432 |
| TBCP-1560_g_1637 | gi\|489763487\|ref\|WP_003667423.1\| | hypothetical protein [*Lactobacillus reuteri*] | 100 | 59 | 0 | 0 | 1 | 177 | 1 | 59 | 1.11E-37 | 118 |
| TBCP-1560_g_1647 | gi\|512739377\|ref\|WP_016497072.1\| | pyrroline-5-carboxylate reductase [*Lactobacillus reuteri*] | 100 | 257 | 0 | 0 | 1 | 771 | 1 | 257 | 0 | 513 |
| TBCP-1560_g_1666 | gi\|183224312\|dbj\|BAG24829.1\| | putative glutaredoxin [*Lactobacillus reuteri* JCM 1112] | 99.862 | 73 | 0 | 0 | 1 | 219 | 3 | 75 | 1.64E-51 | 154 |
| TBCP-1560_g_1667 | gi\|489772428\|ref\|WP_003676331.1\| | ribonucleoside-diphosphate reductase subunit alpha [*Lactobacillus reuteri*] | 100 | 723 | 0 | 0 | 1 | 2169 | 1 | 723 | 0 | 1501 |
| TBCP-1560_g_1669 | gi\|489772430\|ref\|WP_003676333.1\| | bifunctional acetaldehyde-CoA/alcohol dehydrogenase [*Lactobacillus reuteri*] | 100 | 878 | 0 | 0 | 1 | 2634 | 1 | 878 | 0 | 1787 |
| TBCP-1560_g_1676 | gi\|489772438\|ref\|WP_003676341.1\| | hypothetical protein [*Lactobacillus reuteri*] | 98.684 | 76 | 1 | 0 | 1 | 228 | 1 | 76 | 3.34E-52 | 156 |
| TBCP-1560_g_1688 | gi\|489762353\|ref\|WP_003666293.1\| | 50S ribosomal protein L33 [*Lactobacillus reuteri*] | 100 | 49 | 0 | 0 | 1 | 147 | 1 | 49 | 4.99E-32 | 103 |
| TBCP-1560_g_1695 | gi\|337729049\|emb\|CCC04172.1\| | hypothetical protein LRATCC53608_1419 [*Lactobacillus reuteri* ATCC 53608] | 99.83 | 98 | 1 | 0 | 1 | 294 | 1 | 98 | 9.06E-70 | 202 |
| TBCP-1560_g_1704 | gi\|970363458\|emb\|CUR37571.1\| | FIG00746641: hypothetical protein [*Lactobacillus reuteri*] | 100 | 589 | 0 | 0 | 1 | 1767 | 1 | 589 | 0 | 1107 |
| TBCP-1560_g_1719 | gi\|337729072\|emb\|CCC04195.1\| | hypothetical protein LRATCC53608_1442 [*Lactobacillus reuteri* ATCC 53608] | 100 | 77 | 0 | 0 | 1 | 231 | 1 | 77 | 8.45E-52 | 155 |
| TBCP-1560_g_1721 | gi\|512156590\|gb\|AGN99873.1\| | NADH oxidase [*Lactobacillus reuteri* I5007] | 100 | 48 | 0 | 0 | 1 | 144 | 1 | 48 | 6.82E-31 | 100 |
| TBCP-1560_g_1725 | gi\|1017201595\|ref\|WP_063164268.1\| | MarR family transcriptional regulator [*Lactobacillus reuteri*] | 100 | 122 | 0 | 0 | 1 | 366 | 1 | 122 | 3.54E-89 | 253 |
| TBCP-1560_g_1727 | gi\|489772083\|ref\|WP_003675988.1\| | 2-Cys peroxiredoxin [*Lactobacillus reuteri*] | 100 | 166 | 0 | 0 | 1 | 498 | 1 | 166 | 7.45E-123 | 342 |
| TBCP-1560_g_1732 | gi\|489770765\|ref\|WP_003674676.1\| | hypothetical protein [*Lactobacillus reuteri*] | 100 | 107 | 0 | 0 | 1 | 321 | 1 | 107 | 2.08E-74 | 226 |
| TBCP-1560_g_1733 | gi\|489770765\|ref\|WP_003674676.1\| | hypothetical protein [*Lactobacillus reuteri*] | 100 | 348 | 0 | 0 | 1 | 1044 | 123 | 470 | 0 | 674 |
| TBCP-1560_g_1736 | gi\|1017201597\|ref\|WP_063164270.1\| | hypothetical protein [*Lactobacillus reuteri*] | 100 | 727 | 0 | 0 | 1 | 2181 | 22 | 748 | 0 | 1196 |
| TBCP-1560_g_1738 | gi\|737175312\|ref\|WP_035161508.1\| | hypothetical protein [*Lactobacillus reuteri*] | 100 | 62 | 0 | 0 | 1 | 186 | 1 | 62 | 7.72E-40 | 124 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1739 | gi\|512739413\|ref\|WP_016497108.1 | mucus-binding protein [*Lactobacillus reuteri*] | 88.861 | 1185 | 116 | 9 | 1 | 3543 | 1 | 1173 | 0 | 1920 |
| TBCP-1560_g_1739 | gi\|512739413\|ref\|WP_016497108.1 | mucus-binding protein [*Lactobacillus reuteri*] | 99.567 | 693 | 3 | 0 | 10978 | 13056 | 570 | 1262 | 0 | 1300 |
| TBCP-1560_g_1739 | gi\|512739413\|ref\|WP_016497108.1 | mucus-binding protein [*Lactobacillus reuteri*] | 78.734 | 616 | 115 | 9 | 2326 | 4161 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 2944 | 4779 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 3562 | 5397 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 4180 | 6015 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 4798 | 6633 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 5416 | 7251 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 6034 | 7869 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 6652 | 8487 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 7270 | 9105 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 7888 | 9723 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 8506 | 10341 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 9124 | 10959 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 9742 | 11577 | 570 | 1173 | 0 | 917 |
| TBCP-1560_g_1739 | gi\|512739413\|ref\|WP_016497108.1 | mucus-binding protein [*Lactobacillus reuteri*] | 78.734 | 616 | 115 | 9 | 10360 | 12195 | 570 | 1173 | 0 | 917 |
| TBCP-1560_g_1739 | gi\|512739413\|ref\|WP_016497108.1 | mucus-binding protein [*Lactobacillus reuteri*] | 38.164 | 207 | 112 | 9 | 12211 | 12795 | 569 | 771 | 2.66E-22 | 105 |
| TBCP-1560_g_1754 | gi\|337728141\|emb\|CCC03232.1 | conserved hypothetical protein [*Lactobacillus reuteri* ATCC 53608] | 100 | 212 | 0 | 0 | 1 | 636 | 1 | 212 | 1.63E-127 | 357 |
| TBCP-1560_g_1762 | gi\|489761688\|ref\|WP_003665629.1 | cytochrome c554 [*Lactobacillus reuteri*] | 100 | 46 | 0 | 0 | 1 | 138 | 1 | 46 | 4.72E-12 | 52.8 |
| TBCP-1560_g_1765 | gi\|489761683\|ref\|WP_003665624.1 | D-alanine-poly(phosphoribitol) ligase subunit 2 [*Lactobacillus reuteri*] | 100 | 79 | 0 | 0 | 1 | 237 | 1 | 79 | 5.13E-53 | 158 |
| TBCP-1560_g_1778 | gi\|512156647\|gb\|AGN99930.1 | phosphoenolpyruvate synthase [*Lactobacillus reuteri* I5007] | 100 | 578 | 0 | 0 | 1 | 1734 | 1 | 578 | 0 | 1214 |
| TBCP-1560_g_1787 | gi\|512739432\|ref\|WP_016497126.1 | lipoate-protein ligase A [*Lactobacillus reuteri*] | 99.635 | 274 | 1 | 0 | 1 | 822 | 1 | 274 | 0 | 533 |
| TBCP-1560_g_1804 | gi\|337728093\|emb\|CCC03183.1 | conserved hypothetical protein [*Lactobacillus reuteri* ATCC 53608] | 100 | 41 | 0 | 0 | 1 | 123 | 1 | 41 | 1.57E-24 | 84 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1810 | gi\|512739440\|ref\|WP_016497134.1\| | DNA (cytosine-5-)-methyltransferase [*Lactobacillus reuteri*] | 100 | 319 | 0 | 0 | 1 | 957 | 1 | 319 | 0 | 658 |
| TBCP-1560_g_1816 | gi\|512739446\| | endonuclease III [*Lactobacillus reuteri*] | 100 | 213 | 0 | 0 | 1 | 639 | 1 | 213 | 6.68E-162 | 444 |
| TBCP-1560_g_1817 | gi\|512739447\|ref\|WP_016497140.1\| | FMN-binding domain protein [*Lactobacillus reuteri*] | 100 | 92 | 0 | 0 | 1 | 276 | 5 | 96 | 1.59E-64 | 188 |
| TBCP-1560_g_1822 | gi\|512156691\| | transposase [*Lactobacillus reuteri* I5007] | 100 | 34 | 0 | 0 | 1 | 102 | 14 | 47 | 1.32E-19 | 71.2 |
| TBCP-1560_g_1824 | gi\|489767413\|gb\|AGN99974.1\| | ABC transporter substrate-binding protein [*Lactobacillus reuteri*] | 100 | 283 | 0 | 0 | 1 | 849 | 1 | 283 | 0 | 572 |
| TBCP-1560_g_1826 | gi\|1112944237\|ref\|WP_003671339.1\| | ABC-type metal ion transport system, permease component [*Lactobacillus reuteri*] | 100 | 229 | 0 | 0 | 1 | 687 | 1 | 229 | 7.61E-106 | 304 |
| TBCP-1560_g_1827 | gi\|489761558\|gb\|ABI26339.1\| | succinyl-diaminopimelate desuccinylase [*Lactobacillus reuteri*] | 99.738 | 381 | 1 | 0 | 1 | 1143 | 1 | 381 | 0 | 784 |
| TBCP-1560_g_1828 | gi\|970364154\|ref\|WP_003665499.1\| | hypothetical protein LRLP16767_LRPG3B_00672 [*Lactobacillus reuteri*] | 100 | 36 | 0 | 0 | 1 | 108 | 4 | 39 | 1.71E-08 | 43.1 |
| TBCP-1560_g_1852 | gi\|512739465\| | esterase [*Lactobacillus reuteri*] | 100 | 180 | 0 | 0 | 1 | 540 | 1 | 180 | 2.49E-134 | 372 |
| TBCP-1560_g_1854 | gi\|970363126\|ref\|WP_016497159.1\| | Cobalt-zinc-cadmium resistance protein [*Lactobacillus reuteri*] | 97.761 | 134 | 3 | 0 | 1 | 402 | 1 | 134 | 1.46E-96 | 273 |
| TBCP-1560_g_1855 | gi\|512156721\|emb\|CUR37858.1\| | cobalt-zinc-cadmium resistance protein [*Lactobacillus reuteri* I5007] | 99.057 | 212 | 2 | 0 | 1 | 636 | 1 | 212 | 2.81E-137 | 382 |
| TBCP-1560_g_1860 | gi\|489770581\|ref\|WP_003674492.1\| | short-chain dehydrogenase [*Lactobacillus reuteri*] | 98.707 | 232 | 3 | 0 | 43 | 738 | 15 | 246 | 8.47E-171 | 469 |
| TBCP-1560_g_1864 | gi\|489770573\| | cyclic pyranopterin monophosphate synthase accessory protein [*Lactobacillus reuteri*] | 100 | 162 | 0 | 0 | 1 | 486 | 1 | 162 | 4.27E-118 | 329 |
| TBCP-1560_g_1868 | gi\|970370004\|ref\|WP_003674484.1\| | integrase [*Lactobacillus reuteri*] | 100 | 411 | 0 | 0 | 1 | 1233 | 1 | 411 | 0 | 865 |
| TBCP-1560_g_1869 | gi\|489761612\|ref\|WP_003665553.1\| | hypothetical protein [*Lactobacillus reuteri*] | 66.667 | 60 | 20 | 0 | 1 | 180 | 1 | 60 | 4.55E-26 | 89.4 |
| TBCP-1560_g_1870 | gi\|970370006\|emb\|CUR41369.1\| | hypothetical protein LRLP16767_LR202_01424 [*Lactobacillus reuteri*] | 98.857 | 175 | 2 | 0 | 1 | 525 | 1 | 175 | 3.54E-130 | 361 |
| TBCP-1560_g_1872 | gi\|970370008\|emb\|CUR41371.1\| | hypothetical protein LRLP16767_LR202_01426 [*Lactobacillus reuteri*] | 99.582 | 958 | 4 | 0 | 1 | 2874 | 1 | 958 | 0 | 1981 |
| TBCP-1560_g_1873 | gi\|970370009\|emb\|CUR41372.1\| | hypothetical protein LRLP16767_LR202_01427 [*Lactobacillus reuteri*] | 100 | 122 | 0 | 0 | 1 | 366 | 1 | 122 | 1.50E-87 | 249 |
| TBCP-1560_g_1876 | gi\|503689749\|ref\|WP_013923825.1\| | lysozyme M1 (1,4-beta-N-acetylmuramidase) [*Lactobacillus reuteri*] | 86.047 | 129 | 18 | 0 | 187 | 573 | 1 | 129 | 6.65E-81 | 237 |
| TBCP-1560_g_1877 | gi\|489759748\|ref\|WP_003663696.1\| | spore coat protein CotH [*Lactobacillus reuteri*] | 26.557 | 305 | 188 | 9 | 10 | 888 | 1058 | 1338 | 1.70E-19 | 88.2 |
| TBCP-1560_g_1882 | gi\|970369249\|emb\|CUR42509.1\| | hypothetical protein LRLP16767_LR202_02167 [*Lactobacillus reuteri*] | 94.258 | 209 | 12 | 0 | 1 | 627 | 81 | 289 | 8.41E-120 | 340 |
| TBCP-1560_g_1883 | gi\|915462620\|ref\|WP_050802153.1\| | mobilization protein [*Lactobacillus reuteri*] | 97.512 | 402 | 10 | 0 | 1 | 1206 | 11 | 412 | 0 | 738 |
| TBCP-1560_g_1884 | gi\|489770545\|ref\|WP_003674456.1\| | hypothetical protein [*Lactobacillus reuteri*] | 95.408 | 196 | 9 | 0 | 1 | 588 | 1 | 196 | 4.22E-127 | 355 |

TABLE 1-continued

Differential genes between strain CCFM8631 of *Lactobacillus reuteri* and standard strain DSM20016 of *Lactobacillus reuteri*

| Gene ID | nr Database Article ID | Note of the Results | Similarity | Correlation Length | Mismatching | Gap | Gene Start | Gene End | Database Article Start | Database Article End | E | Score |
|---|---|---|---|---|---|---|---|---|---|---|---|---|
| TBCP-1560_g_1908 | gi\|489772006\|ref\|WP_003675911.1\| | 3,4-dihydroxy-2-butanone-4-phosphate synthase [*Lactobacillus reuteri*] | 100 | 220 | 0 | 0 | 1 | 660 | 1 | 220 | 6.96E-165 | 452 |
| TBCP-1560_g_1909 | gi\|970364398\|emb\|CUR36668.1\| | Beta-phosphoglucomutase [*Lactobacillus reuteri*] | 99.531 | 213 | 1 | 0 | 1 | 639 | 1 | 213 | 2.61E-144 | 400 |
| TBCP-1560_g_1944 | gi\|970364175\|emb\|CUR36870.1\| | hypothetical protein LRLP16767_LRPG3B_00662 [*Lactobacillus reuteri*] | 100 | 37 | 0 | 0 | 1 | 111 | 1 | 37 | 7.76E-23 | 79.3 |
| TBCP-1560_g_1953 | gi\|512739498\|ref\|WP_016497191.1\| | branched-chain amino acid transporter [*Lactobacillus reuteri*] | 100 | 107 | 0 | 0 | 1 | 321 | 1 | 107 | 2.65E-74 | 214 |
| TBCP-1560_g_1954 | gi\|490698967\|ref\|WP_004562469.1\| | branched-chain amino acid transporter AzlC [*Lactobacillus reuteri*] | 100 | 230 | 0 | 0 | 1 | 690 | 1 | 230 | 5.57E-139 | 388 |
| TBCP-1560_g_1958 | gi\|337729002\|emb\|CCC04122.1\| | hypothetical protein LRATCC53608_1370 [*Lactobacillus reuteri* ATCC 53608] | 97.826 | 46 | 1 | 0 | 1 | 138 | 1 | 46 | 1.12E-26 | 89.7 |
| TBCP-1560_g_1968 | gi\|512739505\|ref\|WP_016497198.1\| | RNA-binding protein [*Lactobacillus reuteri*] | 100 | 255 | 0 | 0 | 1 | 765 | 1 | 255 | 0 | 521 |
| TBCP-1560_g_1969 | gi\|970370437\|emb\|CUR40976.1\| | Inner membrane protein translocase component YidC, short form OxaI-like [*Lactobacillus reuteri*] | 100 | 263 | 0 | 0 | 1 | 789 | 15 | 277 | 2.91E-158 | 440 |
| TBCP-1560_g_1970 | gi\|489761281\|ref\|WP_003665224.1\| | ribonuclease P protein component [*Lactobacillus reuteri*] | 100 | 117 | 0 | 0 | 1 | 351 | 1 | 117 | 6.87E-84 | 239 |

The beneficial technical effects of the present disclosure are as follows.

The strain CCFM8631 of *Lactobacillus reuteri* of the present disclosure significantly increases neurotransmitter 5-hydroxytryptamine (5-HT) level in peripheral blood of rat, regulates brain-gut axis, relieves mental illnesses related to metabolic syndrome, for example anxiety, depression and so on, recovers the hormone level, for example testosterone and so on in peripheral blood of rat caused by high-fat high-starch diet, recovers abundances of *Bifidobacterium* genus, *Turicibacter* genus, *Oscillospira* genus and *Blautia* genus in abnormal intestinal flora of rat affected by high-fat high-starch diet. In addition, strain CCFM8631 of *Lactobacillus reuteri* has pretty good tolerance to simulated gastrointestinal fluid, and quickly colonizes in intestinal, significantly alleviates pathology damages of tissues, such as liver, duodenum and so on of rat with metabolic syndrome caused by high-fat high-starch diet; significantly improves oral glucose tolerance of rat with metabolic syndrome and decreases the under curve area of glucose tolerance test; significantly increases triglyceride and total cholesterol levels in serum of rat with metabolic syndrome caused by high-fat high-starch diet. The strain CCFM8631 of *Lactobacillus reuteri* of the present disclosure can be used to prepare health foods or medicines that improve metabolic syndrome, regulates intestinal flora, relieves irritable bowel syndrome, regulates brain-gut axis and alleviates mental illness such as anxiety, depression and so on, which has a pretty wide application prospect.

In order to understand the present disclosure further, the technical solutions in the examples of the present disclosure will be described clearly and completely herein in conjunction with the examples of the present disclosure. Apparently, the described examples are only a part of the examples of the present disclosure, rather than all examples. Based on the examples in the present disclosure, all of other examples, made by one of ordinary skill in the art without any creative efforts, fall into the protection scope of the present disclosure.

All of the reagents related to examples of the present disclosure are commercial products without special description, which can be purchased on market. All of the following examples are completed by theory and technology research group of probiotics of Research Center of Food Biotechnology in School of Food Science and Technology, Jiangnan University.

Example 1: Strain CCFM8631 of *Lactobacillus reuteri* has Good Tolerance to Simulated Gastrointestinal Fluid The cryopreserved strain CCFM8631 of *Lactobacillus reuteri* were inoculated in the MRS medium and cultured at 37° C. for 48 hours under anaerobic cultivation, followed by 2 to 3 times subculture in MRS liquid medium. The medium with strain CCFM8631 of *Lactobacillus reuteri* was taken and centrifuged for 5 minutes at a speed of 8000 g, and then resuspended (1:1) in an artificial simulated gastric juice (MRS medium containing 1% pepsin, pH 2.5), followed by anaerobic cultivation at 37° C. Sampling was carried out at 0 hour and 3 hours, and the samples were cultured on MRS medium agar plate for colony counting. The viability numbers were counted and the survival rates were calculated. The survival rate is the rate of the viable count at the desired time point to the viable count at the 0 hour, which was expressed in %.

The medium with cultured strain CCFM8631 of *Lactobacillus reuteri* was taken and centrifuged at a speed of 8000×g for 5 minutes. The bacteria were collected and resuspened (1:1) in artificial simulated intestinal fluid (MRS medium containing 0.3% bile salt from ox, 1% trypsin, pH 8.0), followed by anaerobic cultivation at 37° C. Sampling was carried out at 0 hour and 4 hours, and the samples were cultured on MRS medium agar plate for colony counting. The viability numbers were counted and the survival rates were calculated. The survival rate is the rate of the viable count at the desired time point to the viable count at the 0 hour, which was expressed in %.

The experiment results were shown in Table 2. The results showed that strain CCFM8631 of *Lactobacillus reuteri* has a relative good tolerance to simulated gastrointestinal fluid.

TABLE 2

Tolerance of strain CCFM8631 of *Lactobacillus reuteri* to simulated gastrointestinal fluid

|  | Simulated Gastric Fluid | Simulated Gastric Fluid |
| --- | --- | --- |
| Treatment Time (h) | 3 | 4 |
| Survival Rate (%) | 88.1 ± 5.3 | 67.5 ± 7.2 |

Example 2: Strain CCFM8631 of *Lactobacillus reuteri* has No Toxic and Side Effects on SD Rat The strain CCFM8631 of *Lactobacillus reuteri* bacteria were resuspended in 2% sucrose solution to give a bacterial suspension with a concentration of $3.0 \times 10^9$ CFU/mL. 8 healthy male SD rats with a weight between 180 and 200 g were chosen and acclimated for 1 week before experiments. The rats were administered with the above bacteria suspension by intragastric gavage once daily at a dose of 2 mL/day/rat. The death and weight of the rats were observed and recorded for one week. The results were shown in Table 3.

TABLE 3

Death and changes of body weight in rats

| | Time (day) | | | | | | |
| --- | --- | --- | --- | --- | --- | --- | --- |
| | 1 | 2 | 3 | 4 | 5 | 6 | 7 |
| Weight (g) | 228.2 ± 0.9 | 235.3 ± 1.1 | 241.1 ± 0.5 | 246.7 ± 0.7 | 252.0 ± 0.2 | 258.2 ± 1.3 | 264.5 ± 0.4 |
| Death | — | — | — | — | — | — | — |

Comment:
"—", no death.

The results showed that administration of strain CCFM8631 of *Lactobacillus reuteri* with a concentration of $3.0 \times 10^9$ CFU/mL did not have significant influences on rats, there was no significant change on the body weight and no death. There were no obvious pathological symptoms in the appearance of the rats.

Example 3: Strain CCFM8631 of *Lactobacillus reuteri* has Good Recovery Effect on Tissue Damages of Liver, Duodenum and so on in Rats with Metabolic Syndrome 48 healthy male SD rats with weight from 180 to 200 g were chosen and acclimated for 1 week. The rats were divided into 6 groups randomly: non-specific control group (NC), high-fat high-starch (HFHS) diet model control group, simvastatin control group (SC), rosiglitazone hydrochloride control group (RH), strain CCFM8631 of *Lactobacillus reuteri* intervention group (CCFM8631), *Lactobacillus rhamnosus* LGG control group (LGG), 8 rats per group. The rats were administered with the bacteria suspension ($3.0 \times 10^9$ CFU/mL, in 2% sucrose solution) by intragastric gavage. Grouping and treatment method were shown in Table 4.

TABLE 4

Grouping and treatment method of the experiment

| Group | Number of rats/Group | Treatment Duration | Feed | Treatment Method: administrated by intra-gastric gavage daily |
|---|---|---|---|---|
| NC | 8 | 12 Weeks | Normal feed | 2 ml of 2% sucrose solution |
| HFHS | 8 | 12 Weeks | High-fat high-starch feed | 2 ml of 2% sucrose solution |
| SC | 8 | 12 Weeks | High-fat high-starch feed | 2 ml of 2% sucrose solution containing 3 mg/kg/BW/d of simvastatin |
| RH | 8 | 12 Weeks | High-fat high-starch feed | 2 ml of 2% sucrose solution containing 10 mg/kg/BW/d of rosiglitazone hydrochloride |
| CCFM8631 | 8 | 12 Weeks | High-fat high-starch feed | 2 ml of 2% sucrose solution containing $3.0 \times 10^9$ CFU/mL of CCFM8631 |
| LGG | 8 | 12 Weeks | High-fat high-starch feed | 2 ml of 2% sucrose solution containing $3.0 \times 10^9$ CFU/mL of LGG of |

At the end of the experiment, the rats were fasted (with access to water) for 12 hours. After administering 10% chloral hydrate by peritoneal injection, the rats were anesthetized, the blood samples were collected from the hearts, and the rats were sacrificed by cervical dislocation. The blood samples were centrifuged at a speed of $3000 \times g$ at 4° C. for 10 minutes. The supernatant was collected and frozen at −80° C. for later use. Liver, duodenum and so on were collected and quickly put into ice-cold physiological saline to wash away the blood, followed by fixation in paraformaldehyde. In addition, small intestine was collected and immediately frozen in liquid nitrogen.

Intestine, duodenum and so on were taken and prepared as paraffin sections, followed by HE straining. Morphology of the tissues were observed and imaged under optical microscope for pathological evaluation. The results were shown in FIGS. 2 and 3. The HE straining was performed by the following steps.

(1) Fixation: the tissue samples were washed with physiological saline and immediately put into neutral paraformaldehyde solution (4%) for fixation, and the duration of fixation was generally within 72 hours.

(2) Washing: the tissue samples were washed with running water or immersed in water for a few hours or overnight.

(3) Dehydration: the tissue samples were dehydrated by successively immersing in ethanol solutions of 70%, 80% and 90%, each for 30 minutes, and then immersing in 95% ethanol solution once for 20 minutes, immersing in 100% ethanol solution twice, each time for 10 minutes.

(4) Transparency: the tissue samples were immersed in a mixture of ½ absolute ethanol and ½ xylene for 10 minutes, xylene I for 10 minutes, and xylene II for 10 minutes (until the samples became transparent).

(5) Waxing: the tissue samples were placed in paraffin (at 62° C.) for 2 hours.

(6) Embedding: the largest side of the sample was placed in the bottom so that the sections have the largest tissue surface.

(7) Cutting: the wax blocks were cut by a manually operating microtome into slices with a thickness of 5 μm.

(8) Floatation and adhesion of sections (slice-salvaging): a water bath was used and the water was maintained at 42° C.; sections were placed onto the water surface smoothly.

(9) Drying: slides and slide rack were put into a 55° C. drying oven for about 2 hours until the wax melted.

(10) Hydration: slides were immersed in xylene I and II for 10 minutes respectively for dewaxing, and then immersed in ethanol solutions of 100%, 95%, 90%, 80% and 70% for 5 minutes respectively, and then immersed in distilled water for 3 minutes.

(11) Primary strain: the slides were put into hematoxylin solution and strained for about 20 seconds.

(12) Washing: the slides were washed with tap water for about 15 minutes until the slices became blue. Pay attention to the water flow to avoid the sections detaching from the slide.

(13) Differentiation: the slides were put into ethanol solution with 1% hydrochloric acid for 7 seconds until the slices turned red (the color became light).

(14) Rinsing: the slides were washed with tap water for 15 to 20 minutes until the color recovered blue.

(15) Re-stain: the slides were immersed in eosin solution and immediately taken out for dehydration.

(16) Dehydration: the slides were immersed in 95% ethanol solution I, 95% ethanol solution II and 70% ethanol solution successively, followed by immersing in 80% ethanol solution for 50 seconds and absolute ethanol for 2 minutes.

(17) Transparency: the slides were immersed in ½ of absolute ethanol and ½ of xylene for 1 minute, xylene I for 2 minutes and xylene II for 2 minutes, respectively.

(18) Sealing: after the treatment of xylene, the neutral balsam was used as mounting medium, which could be diluted to appropriate consistency with xylene.

Figure 2:
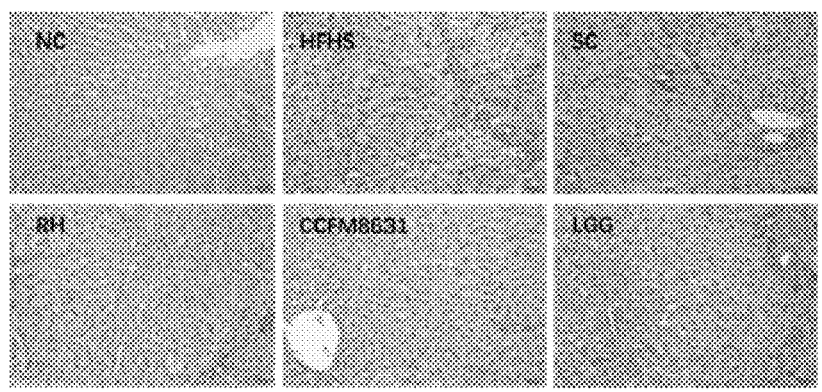
FIG. 2 shows effects of strain CCFM8631 of *Lactobacillus reuteri* on tissue structure of liver in rat with metabolic syndrome.
Figure 3:
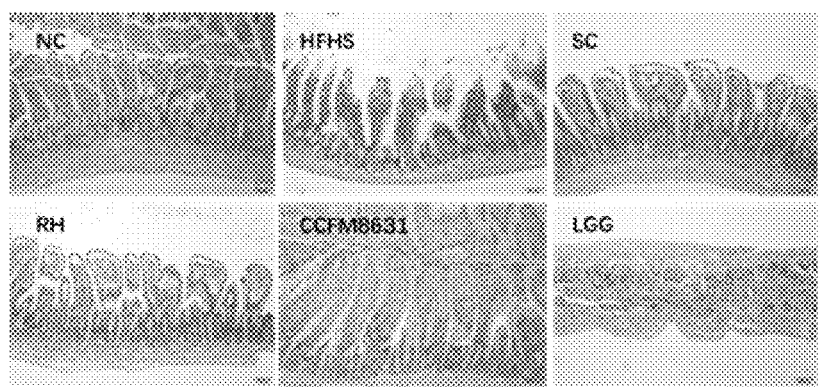
FIG. 3 shows effects of strain CCFM8631 of *Lactobacillus reuteri* on tissue structure of duodenum in rat with metabolic syndrome.

FIG. 2 showed that high-fat high-starch diet caused hepatocyte microvesicular steatosis, and a number of rats have infiltration of inflammatory cell and hyperplasia of fibrous tissue. In high-fat high-starch diet model control group (HFHS), there was significant hyperplasia of fibrous tissue in liver tissue and morphologic features of early fibrosis. In strain CCFM8631 of *Lactobacillus reuteri* intervention group (CCFM8631), administration of strain CCFM8631 of *Lactobacillus reuteri* by intragastric gavage significantly improved the lesions above, and the effects were significantly better than that of group LGG FIG. 3 showed that under optical microscope, lesions of duodenum were villi broadening, interstitial edema, increase of inflammatory cells and increase of interstitial macrophages in a few cases. In strain CCFM8631 of *Lactobacillus reuteri* intervention group (CCFM8631), administration of strain CCFM8631 of *Lactobacillus reuteri* by intragastric gavage improved the lesions above, and the effects were significantly better than that of group LGG.

Example 4: Strain CCFM8631 of *Lactobacillus reuteri* has Recovery Effect on Intestinal Flora Imbalance Caused by High-Fat High-Starch Diet Grouping, molding and treatment processes using SD rats were the same as described in Example 3. Before the end of the experiment, fresh feces of the rats were taken and metagenome samples were extracted. A second-generation sequencer was used for sequencing and the microbial community structure was analyzed.

Figure 4:
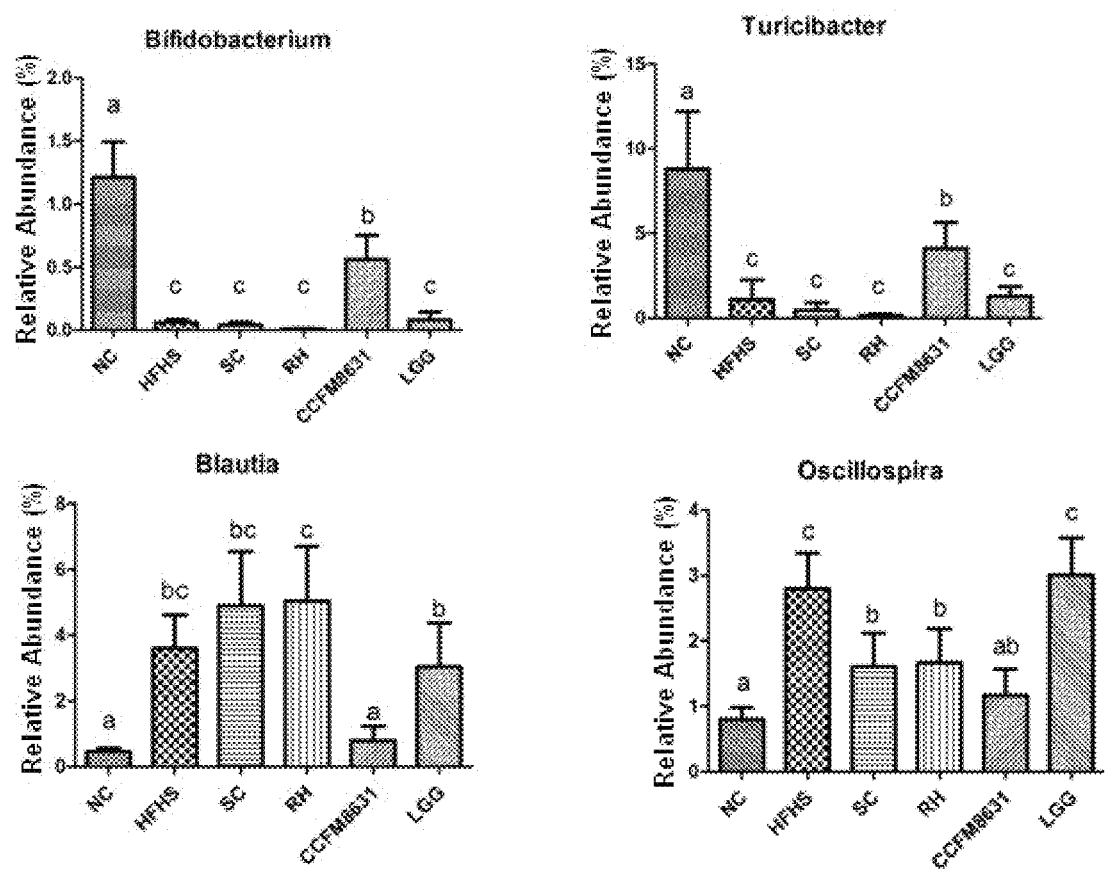
FIG. 4 shows effects of strain CCFM8631 of *Lactobacillus reuteri* on abundances of some intestinal microbes in rat with metabolic syndrome; and there are significant differences ($P<0.05$) between a, b and c groups.

The experiment results were shown in FIG. 4. In feces of high-fat high-starch diet model control group (HFHS), relative abundances of intestinal microbes *Bifidobacterium* genus and *Turicibacter* genus significantly decreased. In strain CCFM8631 of *Lactobacillus reuteri* intervention group (CCFM8631), intake of strain CCFM8631 of *Lactobacillus reuteri* leaded to a significant recovery of the relative abundances of these two genera, while drugs and LGG did not show recovery effect on the abundances of these two genera intestinal microbes. In addition, in rat feces of the high-fat high-starch diet model control group (HFHS), the relative abundance of intestinal microbes of *Oscillospira* genes and *Blautia* genus significantly increased. While in strain CCFM8631 of *Lactobacillus reuteri* intervention group (CCFM8631), intake of strain CCFM8631 of *Lactobacillus reuteri* regulated the abundance of *Blautia* genus back to normal level, and the effects were better than that of the drugs and LGG.

Example 5: Strain CCFM8631 of *Lactobacillus reuteri* Reduced (Fasting) Blood Glucose Level of Rats with Metabolic Syndrome Grouping, molding and treatment processes using SD rats were the same as described in Example 3.

Figure 5:
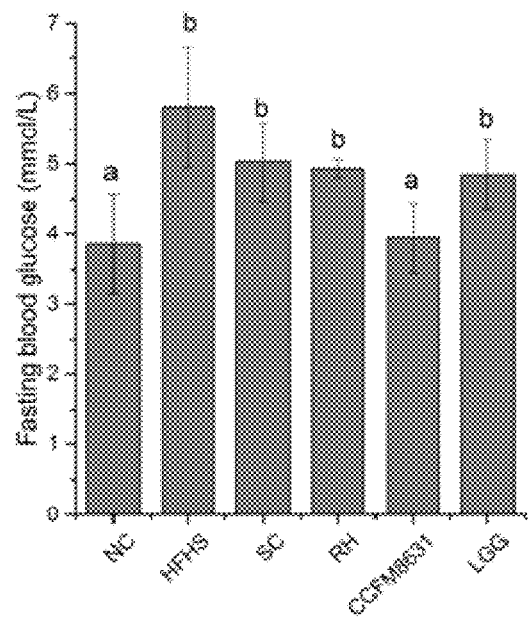
FIG. 5 shows effects of strain CCFM8631 of *Lactobacillus reuteri* on oral glucose tolerance in rat with metabolic syndrome; and there are significant differences ($P<0.05$) between a, b and c groups.

At the end of the experiment the rats were fasted (with access to water) for 12 hours and fasting blood glucose level of the rats was tested. The results were shown in FIG. 5.

In high-fat high-starch diet model control group (HFHS), fasting blood glucose level of rats significantly increased. In strain CCFM8631 of *Lactobacillus reuteri* intervention group (CCFM8631), administration of strain CCFM8631 of *Lactobacillus reuteri* by intragastric gavage significantly decreased fasting blood glucose level of model rats, approximately to non-specific control group, and its ability to decrease fasting blood glucose level of rat is better than that of rosiglitazone hydrochloride control group (RH) and *Lactobacillus rhamnosus* LGG control group (LGG).

Example 6: Strain CCFM8631 of *Lactobacillus reuteri* Increased Glucose Tolerance of Rat with Metabolic Syndrome Grouping, molding and treatment processes using SD rats were the same as described in Example 3. At the end of the experiment, the rats were fasted (with access to water) for 12 hours. Glucose solution (2 g/kg) was injected by intraperitoneal injection and the blood glucose level was measured at 0, 30, 60 and 120 minutes. The experiment results were shown in FIGS. 6 and 7.

Figure 6:
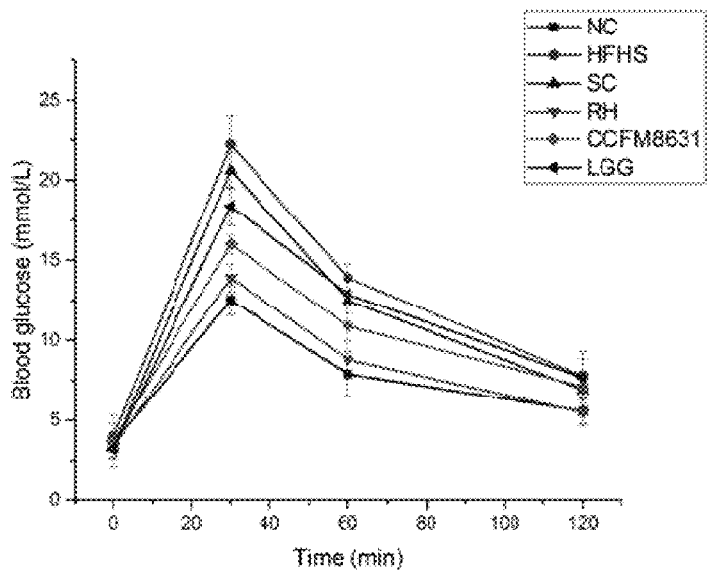
FIG. 6 is a curve showing changes of blood glucose level in oral glucose tolerance test.
Figure 7:
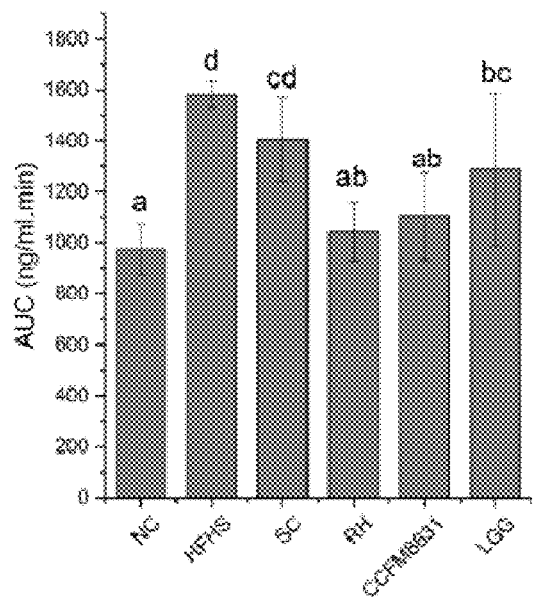
FIG. 7 shows the area under the curve ($AUC_{glucose}$) in oral glucose tolerance test.

As shown in FIG. 6, glucose tolerance of rats in high-fat high-starch diet model control group (HFHS) was poor. After administration of glucose by intragastric gavage, blood glucose level rose significantly and decreased slowly. As shown in FIG. 7, in strain CCFM8631 of *Lactobacillus reuteri* intervention group (CCFM8631), administration of strain CCFM8631 of *Lactobacillus reuteri* by intragastric gavage significantly decreased $AUC_{glucose}$ area, and there was no significant difference comparing with that of rosiglitazone hydrochloride control group (RH) and non-specific control group (NC). This indicated that strain CCFM8631 of *Lactobacillus reuteri* significantly improves oral glucose tolerance, and the effect was better than that of *Lactobacillus rhamnosus* LGG These results were consistent with that of the blood glucose indexes, indicating that strain CCFM8631 of *Lactobacillus reuteri* further decreased blood glucose level by increasing glucose tolerance.

Example 7: Strain CCFM8631 of *Lactobacillus reuteri* Decreased Total Cholesterol (TC) Level in Serum of Rat with Metabolic Syndrome Grouping, molding and treatment processes using SD rats were the same as described in Example 3. At the end of the experiment, the rats were fasted (with access to water) for 12 hours. After administering 10% chloral hydrate by peritoneal injection for anesthetizing, blood sample was collected from the heart, and the rats were sacrificed by cervical dislocation. The blood samples were centrifuged at a speed of 3000×g at 4° C. for 10 minutes, and the supernatant was collected. The total cholesterol (TC) in the blood was measured according to the protocol of the detection kit. The experiment results were shown in FIG. 8.

Figure 8:
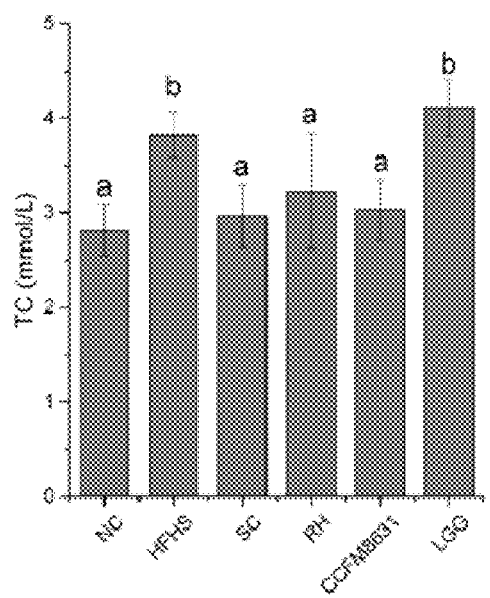
FIG. 8 shows effects of strain CCFM8631 of *Lactobacillus reuteri* on total cholesterol (TC) in serum of rat with metabolic syndrome; and there are significant differences ($P<0.05$) between a, b and c groups.

As shown in FIG. 8, total cholesterol in serum of rats in high-fat high-starch diet model control group (HFHS) significantly increased. In strain CCFM8631 of *Lactobacillus reuteri* intervention group (CCFM8631), administration of strain CCFM8631 of *Lactobacillus reuteri* by intragastric gavage decreased level of total cholesterol in serum.

Figure 9:
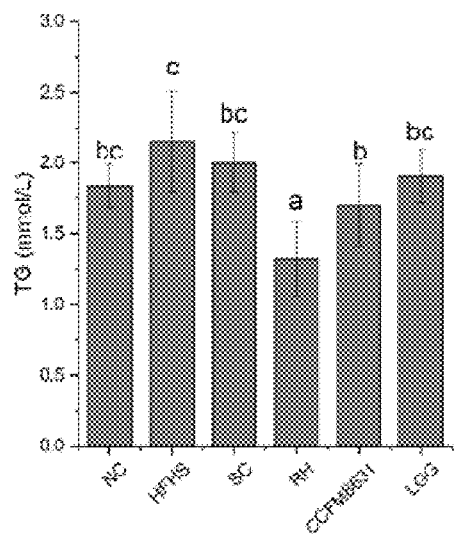
FIG. 9 shows effects of strain CCFM8631 of *Lactobacillus reuteri* on triglyceride (TG) in serum of rat with metabolic syndrome; and there are significant differences ($P<0.05$) between a, b and c groups.

Example 8: Strain CCFM8631 of *Lactobacillus reuteri* Decreased Triglyceride (TG) Level in Serum of Metabolic Syndrome Rat Grouping, molding and treatment processes using SD rats were the same as described in Example 3. At the end of the experiment, the rats were fasted (with access to water) for 12 hours. After administering 10% chloral hydrate by peritoneal injection for anesthetizing, blood sample was collected from the heart, and the rats were sacrificed by cervical dislocation. The blood samples were centrifuged at a speed of 3000×g at 4° C. for 10 minutes, and the supernatant was collected. The triglyceride (TG) level in the blood was measured according to the protocol of the detection kit. The experiment results were shown in FIG. 9.

As shown in the experiment results, comparing with non-specific control group (NC), triglyceride level in serum of rats in high-fat high-starch diet model control group significantly increased. In strain CCFM8631 of *Lactobacillus reuteri* intervention group, administration of strain CCFM8631 of *Lactobacillus reuteri* by intragastric gavage decreased triglyceride level in serum, and the effect was better than that of LGG Example 9: Strain CCFM8631 of *Lactobacillus reuteri* Affected 5-HT and Testosterone Levels in Serum of Rat with Metabolic Syndrome Grouping, molding and treatment processes using SD rats were the same as described in Example 3. At the end of the experiment, the rats were fasted (with access to water) for 12 hours. After administering 10% chloral hydrate by peritoneal injection for anesthetizing, blood sample was collected from the heart, and the rats were sacrificed by cervical dislocation. The blood samples were centrifuged at a speed of 3000×g at 4° C. for 10 minutes, and the supernatant was collected. The 5-HT and testosterone levels in the blood were measured according to the protocol of the detection kit.

Figure 10:
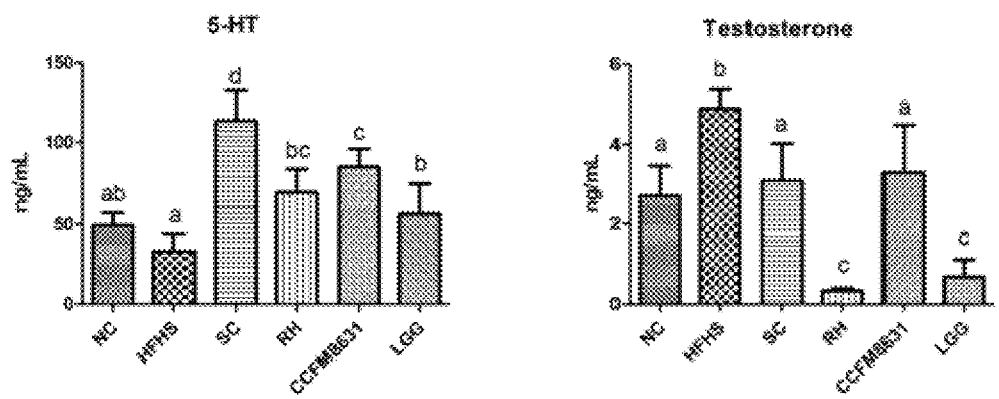
FIG. 10 shows effects of strain CCFM8631 of *Lactobacillus reuteri* on 5-hydroxytryptamine (5-HT) and testosterone levels of rat with metabolic syndrome; and there are significant differences (P<0.05) between a, b and c groups.

The experiment results were shown in FIG. 10. As shown in the experiment results, strain CCFM8631 of *Lactobacillus reuteri* significantly increased 5-HT level in serum of rats, while LGG has no significant improvement on 5-HT level. Comparing with non-specific control group (NC), testosterone level in serum of rats in high-fat high-starch diet model control group (HFHS) significantly increased. In strain CCFM8631 of *Lactobacillus reuteri* intervention group (CCFM8631), administration of strain CCFM8631 of *Lactobacillus reuteri* by intragastric gavage reduced the testosterone level in serum back to normal, and LGG can decrease the testosterone level greatly lower than normal level in model rats.

What is claimed is:

1. A method of improving metabolic syndrome, modulating intestinal flora, improving irritable bowel syndrome, modulating brain-gut axis, relieving anxiety and/or depression, comprising administering a strain CCFM8631 of *Lactobacillus reuteri* which is deposited at China General Microbiological Culture Collection Center (CGMCC) with an accession number CGMCC 14394, to a subject in need thereof.

2. The method according to claim 1, wherein the improving of metabolic syndrome is to relieve the symptoms of hyperglycemia and hyperlipidemia, inflammation of liver and duodenum, and liver fibrosis; the modulating of intestinal flora is to normalize abnormal abundances of *Blautia* genus, *Turicibacter* genus, *Oscillospira* genus and *Bifidobacterium* genus in the intestinal flora; and the modulating of brain-gut axis and the relieving of anxiety and/or depression is to increase 5-hydroxytryptamine level in peripheral blood.

3. A method for preparing a composition, comprising: inoculating the strain CCFM8631 of *Lactobacillus reuteri* to MRS medium at an inoculum size of 2 to 4 wt %, culturing for 18 to 20 h at 37° C. under anaerobic condition, collecting bacteria, resuspending the bacteria with a protectant to a bacterial density of $10^{10}$ CFU/mL, culturing the suspension at 37° C. for 50 to 70 minutes under anaerobic condition, and drying the resulting culture, wherein the strain CCFM8631 is deposited at China General Microbiological Culture Collection Center (CGMCC) with an accession number CGMCC 14394.

4. The method according to claim 3, wherein the protectant is a aqueous solution containing 100 g/L to 150 g/L of nonfat milk powder, 100 g/L to 150 g/L of maltodextrin, and 140 g/L to 160 g/L of trehalose; the drying is vacuum freeze-drying after pre-freezing at −15 to −20° C. for 8 to 14 h.

* * * * *